(12) United States Patent
Rose et al.

(10) Patent No.: US 6,986,995 B2
(45) Date of Patent: Jan. 17, 2006

(54) METHODS OF DIAGNOSING LIVER FIBROSIS

(75) Inventors: Steven L. Rose, Escondido, CA (US); Esther H. Oh, San Diego, CA (US); Michael J. Walsh, San Diego, CA (US)

(73) Assignee: Prometheus Laboratories, Inc., San Diego, CA (US)

( * ) Notice: Subject to any disclaimer, the term of this patent is extended or adjusted under 35 U.S.C. 154(b) by 262 days.

(21) Appl. No.: 10/087,188

(22) Filed: Feb. 28, 2002

(65) Prior Publication Data

US 2003/0175686 A1    Sep. 18, 2003

(51) Int. Cl.
 C12Q 1/37      (2006.01)
 G01N 33/576    (2006.01)
 G01N 33/68     (2006.01)

(52) U.S. Cl. .............................. 435/7.1; 435/4; 435/5; 435/7.21; 435/7.4; 435/23; 435/24; 436/63; 436/69; 436/71; 436/86; 436/87; 436/94; 436/518; 436/536; 436/811; 436/820; 702/19; 706/924

(58) Field of Classification Search ................... 435/4, 435/5, 7.1, 7.21, 23, 24, 7.4; 436/63, 69, 436/71, 86, 87, 94, 518, 536, 811, 820, 5.8; 702/19; 706/924
See application file for complete search history.

(56) References Cited

U.S. PATENT DOCUMENTS

| 5,019,498 | A | 5/1991 | Chichibu .................... 435/7.5 |
| 6,218,129 | B1 | 4/2001 | Walsh et al. ................ 435/7.21 |
| 6,631,330 | B1 * | 10/2003 | Poynard ...................... 702/19 |

FOREIGN PATENT DOCUMENTS

| EP | 0 911 343 | 4/1999 |
| EP | 1 150 123 | 10/2001 |
| WO | WO 01/86304 | 11/2001 |

OTHER PUBLICATIONS

Afdhal et al, Journal of Hepatology, 27, 993-1002, 1997.*
Oh et al, Current Gastroenterology Reports, 3, 12-18, 2001.*
Armstrong and Quigley, "$\alpha_2$- macroglobulin: an evolutionarily conserved arm of the innate immune system," *Develop. Compar. Immunol.* 23:375-390 (1999).
Arthur et al., "Tissue inhibitors of metalloproteinases: Role in liver fibrosis and alcoholic liver disease," *Alcohol Clin. Exp. Res.* 23:940-943 (1999).
Bodden et al., "Functional domains of human TIMP-1 (tissue inhibitor of metalloproteinases)," *J. Biol. Chem.* 269:18943-18952 (1994).
Boeker et al., "Diagnostic potential of circulating TIMP-1 and MMP-2 as markers of liver fibrosis in patients with chronic hepatitis C," *Clin Chim Acta* 316:71-81 (2002).

Böker et al., "Tissue inhibitors of metalloproteinases in liver and serum/plasma in chronic active hepatitis C and HCV-induced cirrhosis," *Hepato-Gastroenterol* 47:812-819 (2000).
Bramley et al., "Serum hyaluronate as a marker of hepatic derangement in acute liver damage," *J. Hepatol.* 13:8-13 (1991).
Brandt et al., "A convenient radiometric assay for hyaluronan," *Acta Otolaryn.* 442 (Suppl.):31-35 (1987).
Bray et al., "Early changes in lung tissue hyaluronan (hyaluronic acid) and hyaluronidase bleomycin-induced alveolitis in hamsters," *Am. Rev. Respir. Dis.* 3:284-288 (1991).
Brophy et al., "Tissue inhibitor of metallo-proteinases (TIMP) is matrix associated in aortic tissue: Report of a radioimmunoassay," *Biochem. Biophys. Res. Comm.* 167:898-903 (1990).
Castera et al., "Serum laminin and type IV collagen are accurate markers of histologically severe alcoholic hepatitis in patients with cirrhosis," *J. Hepatol.* 32:412-418 (2000).
Cawston et al., "Protein Inhibitors of Metalloproteinases" in Barrett and Salvesen (Eds), *Proteinase Inhibitors* Amsterdam Elsevier Science Publishers pp. 589-610 (1986).
Cazzolla et al., "Development of an enzyme-linked immunosorbent assay, using a monoclonal antibody against $\alpha_2$-macroglobulin, for diagnosis of systemic lupus erythematosus," *Clinical Biochemistry* 32:249-255 (1999).
Chichibu et al., "Assay of serum hyaluronic acid in clinical application," *Clin. Chim. Acta* 181:317-323 (1989).
Delpech et al., "Immunoenzymoassay of the hyaluronic acid-hyaluronectin interaction: application to the detection of hyaluronic acid in serum of normal subjects and cancer patients," *Anal. Biochem.* 149:555-565 (1985).
Docherty et al., "Sequence of human tissue inhibitor of metalloproteinases and its identity to erythroid-potentiating activity," *Nature* 318:66-69 (1985).
Emlen et al., "Measurement of serum hyaluronic acid in patients with rheumatoid arthritis: Correlation with disease activity," *J. Rheum.* 23:974-978 (1996).
Engstrom-Laurent et al., "Concentration of sodium hyaluronate in serum," *Scand. J. Clin. Lab. Invest.* 45:497-504 (1985).

(Continued)

*Primary Examiner*—David Saunders
(74) *Attorney, Agent, or Firm*—Townsend and Townsend and Crew LLP

(57) ABSTRACT

The present invention provides a method of diagnosing the presence or severity of liver fibrosis in an individual by detecting α2-macroglobulin (α2-MG) in a sample from the individual; detecting hyaluronic acid (HA) in a sample from the individual; detecting tissue inhibitor of metalloproteinases-1 (TIMP-1) in a sample from the individual; and diagnosing the presence or severity of liver fibrosis in the individual based on the presence or level of α2-MG, HA and TIMP-1.

63 Claims, 2 Drawing Sheets

OTHER PUBLICATIONS

Fink et al., "Measurement of proteins with the Behring Nephelometer. A multicentre evaluation," *J. Clin. Chem. Clin. Biochem.* 27:261-276 (1989).

Fortunato et al., "Multivariate discriminant function based on six biochemical markers in blood can predict the cirrhotic evolution of chronic hepatitis," *Clin. Chem.* 47:1696-1700 (2001).

Gabrielli et al., "Serum laminin P1 in chronic viral hepatitis: correlations with liver histological activity and diagnositic value," *Clin. Chim. Acta* 252:171-180 (1996).

Gabrielli et al., "Serum laminin and type III procollagen in chronic hepatitis C. Diagnositic value in the assessment of disease activity and fibrosis," *Clin. Chem. Acta* 265:21-31 (1997).

Ganrot, "Determination of $\alpha_2$-macroglobin as trypsin-protein esterase," *Clin. Chim. Acta* 14:493-501 (1966).

Goldberg et al., "Elevated plasma levels of hyaluronate in patients with osteoarthritis and rheumatoid arthritis," *Arthritis Rheum.* 34:799-807 (1991).

Goldberg, "Enzyme-linked immunosorbent assay for hyaluronan using cartilage proteoglycan and an antibody to keratan sulfate," *Anal. Biochem.* 174:448-458 (1988).

Groft et al., "Differential expression and localization of TIMP-1 and TIMP-4 in human gliomas," *Br. J. Cancer* 85:55-63 (2001).

Guechot et al., "Diagnositc accuracy of hyaluronan and type III procollagen amino-terminal peptide serum assays as markers of liver fibrosis in chronic viral hepatitis C evaluated by ROC curve analysis," *Clin. Chem.* 42:558-563 (1996).

Hakala et al., "Human cartilage gp-39, a major secretory product of articular chondrocytes and synovial cells, is a mammalian member of a chitinase protein family," *J. Biol. Chem.* 268:25803-25810 (1993).

Hall and Roberts, "Physical and chemical properties of human plasma $\alpha_2$-macroglobin," *Biochem. J.* 171:27-38 (1978).

Hayasaka and Saisho, "Serum markers as tools to monitor liver fibrosis," *Digestion* 59:381-384 (1998).

Imber and Pizzo, "Clearance and binding of two electrophoretic "fast" forms of human $\alpha_2$-macroglobin," *J. Biol. Chem.* 256:8134-8139 (1981).

Imbert-Bismut et al., "Biochemical markers of liver fibrosis in patients with hepatitis C virus infection: a prospective study," *Lancet* 357:1069-1075 (2001).

Janowska-Wieczorek et al., "Differential MMP and TIMP production by human marrow and peripheral blood CD34'cells in response to chemokines," *Exp. Hematol.* 28:1274-1285 (2000).

Jeffers et al., "Procollagen-III peptide and chronic viral C hepatitis," *Am. J. Gastroenterol.* 90:1437-1440 (1995).

Johansen et al., "Plasma YKL-40: a new potential marker of fibrosis in patients with alcoholic cirrhosis?," *Scand. J. Gastroenterol.* 32:582-590 (1997).

Johansen et al., "A new biochemical marker for joint injury. Analysis of YKL-40 in serum and synovial fluid," *Br. J. Rheumatology* 32:949-955 (1993).

Johansen et al., "Serum YKL-40 is increased in patients with hepatic fibrosis" *J. Hepatol.* 323:911-920 (2000).

Johansen et al., "Indentification of proteins secreted by human osteoblastic cells in culture," *J. Bone Miner. Res.* 7:501-511 (1992).

Kasahara et al., "Circulating matrix metalloproteinase-2 and tissue inhibitor of metalloproteinase-1 as serum markers of fibrosis in patients with chronic hepatitis C," *J Hepatol* 26:574-583 (1997).

Knodell et al., "Formulation and application of a numerical scoring system for assessing historical activity in asymptomatic chronic active hepatitis," *Hepatology* 1:431-435 (1981).

Kodama et al. "Rapid one-step sandwich enzyme immunoassay for tissue inhibitor of metalloproteinases," *J. Immunol. Methods* 127:103-108 (1990).

Konttinen et al., "Serum baseline hyaluronate and disease activity in rheumatoid arthritis" *Clin. Chimica Acta* 193:39-47 (1990).

Kossakowska et al., "Altered balance between matrix metalloproteinases ans their inhibitors in experimental biliary fibrosis," *Amer. J. Patholody* 153:1895-1902 (1998).

Kropf et al., "Efficacy of serum laminin measurement for diagnosis of fibrotic liver diseases," *Clin. Chem.* 34:2026-2030 (1988).

Laurent and Tengblad, "Determination of hyaluronate in biological samples by a specific radioassay technique," *Anal. Biol Chem* 108:386-394 (1980).

Li et al., "Accumulation of hyaluronate in human lung carcinoma as measured by a new hyaluronate ELISA," *Conn. Tissue Res.* 19:243-253 (1989).

Lindqvist et al., "Seven different assays of hyaluronan compared for clinical utitlity," *Clin. Chem.* 38:127-132 (1992).

Maingonnat and Delpech, "Enzyme immunoassay of hyaluronic acid in serum and pleural fluid using sheep brain hyaluronectin," *Ann. Clin. Biochem.* 28:305-306 (1991).

McHutchison et al., "Measurement of serum hyaluronic acid in patients with chronic hepatitis C and its relationship to liver histology," *J. Gastroenterol. Hepatol.* 15:945-951 (2000).

Murawaki et al., "Serum tissue inhibitor of metalloproteinases in patients with chronic liver disease and with hepatocellular carcinoma," *Clin Chim Acta* 218:47-58 (1993).

Murawaki et al. "Diagnostic value of serum markers of connective tissue turnover for predicting histological staging and grading in patients with chronic hepatitis C," *J Gastroenterol* 36:399-406 (2001).

Murphy et al., "An inhibitor of collagenase from human anmiotic fluid. Purification, characterization and action on metalloproteinases," *Biochem. J.* 195:167-170 (1981).

Murphy et al., "Inhibition of apoptosis of activated hepatic stellate cells by tissue inhibitor of metalloproteinase-1 is mediated via effects on matrix metalloproteinase inhibition," *J Biol Chem* 277(13):11069-11076 (2002).

Naveau et al., "Alpha-2-macroglobulin and hepatic fibrosis" *Dig Dis Sci* 39:2426-2432 (1994).

Nyirkos and Golds, "Human synovial cells secrete a 39kDa protein similar to a bovine mammary protein expressed during the non-lactating period," *Biochem. J.* 268:265-268 (1990).

Oberti et al., "Noninvasive diagnosis of hepatic fibrosis or cirrhosis," *Gastroenterol.* 113:1609-1616 (1997).

Ortego et al. "Gene expression of proteases and protease inhibitors in the human ciliary epithelium and ODM-2 cells," *Exp. Eye Res.* 65:289-299 (1997).

Paramo et al., "Fibrinolysis/proteolysis balance in stable angina pectoris in relation to angiographic findings," *Thromb. Haemost.* 86:636-639 (2001).

Parra et al., "Tissue inhibitor of metalloproteinase-1 is increased in the saphenofemoral junction of patients with varices in the leg," *J. Vasc. Surg.* 28:669-675 (1998).

Payan et al., "Assay of synovial fluid hyaluronic acid using high-performance liquid chromatography of hyaluronidase digests," *J. Chromatogr.* 566:9-18 (1991).

Pilette et al., "Histopathological evaluation of liver fibrosis: quantitative image anaylsis vs. semi-quantitative scores," *J. Hepatol.* 28:439-446 (1998).

Pitsillides et al. "Circulating and synovial fluid hyaluronan levels," *Arth. Rheum.* 37:1030-1038 (1994).

Poole et al., "Rabbit antibodies to degraded and intact glycosaminoglycans which are naturally occurring and present in arthritic rabbits," *J. Biol. Chem.* 260:6020-6025 (1985).

Poole et al., "Inflammation and cartilage metabolism in rheumatoid arthritis," *Arth. Rheum.* 33:790-799 (1990).

Poynard et al., "A simple biological index for detection of alcohol in liver disease in drinkers," *Gastroenterol.* 100: 1397-1402 (1991).

Poynard et al., "Biochemichal markers of liver fibrosis in patients infected by hepatitis C virus: longitudinal validation in a randomized trial," *J. Viral Hepatitis* 9:128-133 (2002).

Renkema et al., "Chitotriosidase, a chitinase, and the 39-kDa human cartilage glycoprotein, a chitin-binding lectin, are homologues of family 18 glycosyl hydrolases secreted by human macrophages," *Eur. J. Biochem.* 251:504-509 (1998).

Rosenberg et al., "Serum markers predict liver fibrosis," *Hepatol.* 34:396A, Abstract No. 895 (2001).

Saadeh et al., "The role of liver biopsy in chronic hepatitis C," *Hepatology* 33:196-200 (2001).

Sacco et al., "Transforming growth factor β1 and soluble Fas serum levels in hepatocellular carcinoma," *Cytokine* 12:811-814 (2000).

Simon et al., "Identification of differentially expressed messenger RNAs in human melanocytes and melanoma cells," *Cancer Res.* 56:3112-3117 (1996).

Sottrup-Jensen, "α2-Macroglobulin and Related Thiol Ester Plasma Proteins," in Putnam (Ed.) *The Plasma Proteins: Structure, Functional and Genetic Control* Second edition, Orlando: Academic Press pp. 191-291 (1987).

Stricklin and Welgus, "Human skin fibroblast collagenase inhibitor. Purification and biochemical characterization," *J. Biol. Chem.* 258:12252-12258 (1983).

Teare et al., "Comparison of serum procollagen III peptide concentrations and PGA index for assessment of hepatic fibrosis," *Lancet* 342:895-898 (1993).

The French Metavir Cooperative Study Group, "Intraobserver and interobserver variations in liver biopsy interpretation in patients with chronic hepatitis C," *Hepatol.* 20:15-20 (1994).

Ueno et al., "Serum hyaluronate reflects hepatic sinusoidal capillarization," *Gastroenterol.* 105:475-481 (1993).

Verheijden et al., "Human cartilage glycoprotein-39 as a candidate autoantigen in rheumatoid arthritis," *Arthritis Rheum.* 40:1115-1125 (1997).

Volck et al., "YKL-40, a mammalian member of the chitinase family, is a matrix protein of specific granules in human neutrophils," *Proc. Assoc. Am. Physicians* 110:351-360 (1998).

Walsh et al., "Plasma levels of matrix metalloproteinase-2 (MMP-2) and tissue inhibitors of metalloproteinases-1 and -2 (TIMP-1 and TIMP-2) as noninvasive markers of liver disease in chronic hepatitis C," *Dig Dis Sci* 44:624-630 (1999).

Walsh et al., "Basement membrane peptides as markers of liver disease in chronic hepatitis C," *J. Hepatol.* 32:325-330 (2000).

Xuhuai et al., "Clinical significance of serum 7S collagen and type VI collagen levels for the diagnosis of hepatic fibrosis," *Chinese Medical Journal* 110:198-201 (1997).

Yoshiji et al., "Enhanced RNA expression of tissue inhibitor of metalloproteinases-1 (TIMP-1) in human breast cancer," *Int. J. Cancer* 69:131-134 (1996).

* cited by examiner

A
```
   1 cccgccttcc tagctgtccc agtggagaag gaacaagcgc ctcactgcat ctgtgcaaac
  61 gggcggcaaa ctgtgtcctg ggcagtaacc ccaaagtcat taggaaatgt gaatttcact
 121 gtgagcgcag aggcactaga gtctcaagag ctgtgtggga ctgaggtgcc ttcagttcct
 181 gaacacggaa ggaaagacac agtcatcaag cctctgttgg ttgaacctga aggactagag
 241 aaggaaacaa cattcaactc cctactttgt ccatcaggtg gtgaggtttc tgaagaatta
 301 tccctgaaac tgccaccaaa tgtggtagaa gaatctgccc gagcttctgt ctcagttttg
 361 ggagacatat taggctctgc catgcaaaac acacaaaatc ttctccagat gccctatggc
 421 tgtggagagc agaatatggt cctctttgct cctaacatct atgtactgga ttatctaaat
 481 gaaacacagc agcttactcc agagatcaag tccaaggcca ttggctatct caacactggt
 541 taccagagac agttgaacta caaacactat gatggctcct acagcacctt tggggagcga
 601 tatggcagga accagggcaa cacctggctc acagcctttg ttctgaagac ttttgcccaa
 661 gctcgagcct acatcttcat cgatgaagca cacattaccc aagccctcat atggctctcc
 721 cagaggcaga aggacaatgg ctgtttcagg agctctgggt cactgctcaa caatgccata
 781 aagggaggag tagaagatga agtgaccctc tccgcctata tcaccatcgc ccttctggag
 841 attcctctca cagtcactca ccctgttgtc cgcaatgccc tgttttgcct ggagtcagcc
 901 tggaagacag cacaagaagg ggaccatggc agccatgtat ataccaaaga cctgctggcc
 961 tatgcttttg ccctggcagg taaccaggac aagaggaagg aagtactcaa gtcacttaat
1021 gaggaagctg tgaagaaaga caactctgtc cattgggagc gccctcagaa acccaaggca
1081 ccagtggggg attttacga accccaggct ccctctgctg aggtggagat gacatcctat
1141 gtgctcctcg cttatctcac ggcccagcca gccccaacct cggaggacct gacctctgca
1201 accaacatcg tgaagtggat cacgaagcag cagaatgccc agggcggttt ctcctccacc
1261 caggacacag tggtggctct ccatgctctg tccaaatatg gagcagccac atttaccagg
1321 actgggaagg ctgcacaggt gactatccag tcttcaggga catttccag caaattccaa
1381 gtggacaaca caaccgcct gttactgcag caggtctcat gccagagct gcctggggaa
1441 tacagcatga agtgacagg agaaggatgt gtctacctcc agacatcctt gaaatacaat
1501 attctcccag aaaaggaaga gttcccctt gctttaggag tgcagactct gcctcaaact
1561 tgtgatgaac ccaaagccca caccagcttc caaatctccc taagtgtcag ttacacaggg
1621 agccgctctg cctccaacat ggcgatcgtt gatgtgaaga tggtctctgg cttcattccc
1681 ctgaagccaa cagtgaaaat gcttgaaaga tctaaccatg tgagccggac agaagtcagc
1741 agcaaccatg tcttgattta ccttgataag gtgtcaaatc agacactgag cttgttcttc
1801 acggttctgc aagatgtccc agtaagagat ctgaaaccag ccatagtgaa agtctatgat
1861 tactacgaga cggatgagtt tgcaattgct gagtacaatg ctccttgcag caaagatctt
1921 ggaaatgctt gaagaccaca aggctgaaaa gtgctttgct ggagtcctgt tctcagagct
1981 ccacagaaga cacgtgtttt tgtatcttta aagacttgat gaataaacac tttttctggt
2041 c
```

B PAFLAVPVEKEQAPHCICANGRQTVSWAVTPKSLGNVNFTVSAEALESQELCGTEVPSVPEHGRKDTVIKPL
LVEPEGLEKETTFNSLLCPSGGEVSEELSLKLPPNVVEESARASVSVLGDILGSAMQNTQNLLQMPYGCGEQ
NMVLFAPNIYVLDYLNETQQLTPEIKSKAIGYLNTGYQRQLNYKHYDGSYSTFGERYGRNQGNTWLTAFVLK
TFAQARAYIFIDEAHITQALIWLSQRQKDNGCFRSSGSLLNNAIKGGVEDEVTLSAYITIALLEIPLTVTHP
VVRNALFCLESAWKTAQEGDHGSHVYTKDLLAYAFALAGNQDKRKEVLKSLNEEAVKKDNSVHWERPQKPKA
PVGDFYEPQAPSAEVEMTSYVLLAYLTAQPAPTSEDLTSATNIVKWITKQQNAQGGFSSTQDTVVALHALSK
YGAATFTRTGKAAQVTIQSSGTFSSKFQVDNNNRLLLQQVSLPELPGEYSMKVTGEGCVYLQTSLKYNILPE
KEEFPFALGVQTLPQTCDEPKAHTSFQISLSVSYTGSRSASNMAIVDVKMVSGFIPLKPTVKMLERSNHVSR
TEVSSNHVLIYLDKVSNQTLSLFFTVLQDVPVRDLKPAIVKVYDYYETDEFAIAEYNAPCSKDLGNA

FIGURE 1

A
```
  1 aggggcctta gcgtgccgca tcgccgagat ccagcgccca gagagacacc agagaaccca
 61 ccatggcccc ctttgagccc ctggcttctg gcatcctgtt gttgctgtgg ctgatagccc
121 ccagcagggc ctgcacctgt gtcccacccc acccacagac ggccttctgc aattccgacc
181 tcgtcatcag ggccaagttc gtggggacac cagaagtcaa ccagaccacc ttataccagc
241 gttatgagat caagatgacc aagatgtata aagggttcca agccttaggg gatgccgctg
301 acatccggtt cgtctacacc cccgccatgg agagtgtctg cggatacttc cacaggtccc
361 acaaccgcag cgaggagttt ctcattgctg gaaaactgca ggatggactc ttgcacatca
421 ctacctgcag tttcgtggct ccctggaaca gcctgagctt agctcagcgc cggggcttca
481 ccaagaccta cactgttggc tgtgaggaat gcacagtgtt tccctgttta tccatcccct
541 gcaaactgca gagtggcact cattgcttgt ggacggacca gctcctccaa ggctctgaaa
601 agggcttcca gtcccgtcac cttgcctgcc tgcctcggga gccagggctg tgcacctggc
661 agtccctgcg gtcccagata gcctgaatcc tgcccggagt ggaactgaag cctgcacagt
721 gtccaccctg ttcccactcc catctttctt ccggacaatg aaataaagag ttaccaccca
781 gc
```

B
MAPFEPLASGILLLLWLIAPSRACTCVPPHPQTAFCNSDLVIRAKFVGTPEVNQTTLYQRYEIKMTKMYKG
FQALGDAADIRFVYTPAMESVCGYFHRSHNRSEEFLIAGKLQDGLLHITTCSFVAPWNSLSLAQRRGFTKT
YTVGCEECTVFPCLSIPCKLQSGTHCLWTDQLLQGSEKGFQSRHLACLPREPGLCTWQSLRSQIA

FIGURE 2

METHODS OF DIAGNOSING LIVER FIBROSIS

BACKGROUND OF THE INVENTION

1. Field of the Invention

The present invention relates generally to the fields of hepatology and fibrosis and, more specifically, to a panel of serological markers which together are diagnostic of liver fibrosis.

2. Background Information

Progressive fibrosis of the liver, kidney, lungs and other organs frequently results in organ failure that leads to organ transplantation or death, affecting millions in the United States and worldwide. Hepatic fibrosis, for example, is the leading non-malignant gastrointestinal cause of death in the United States, and the progression of fibrosis is the single most important determinant of morbidity and mortality in patients with chronic liver disease. Furthermore, the process of fibrosis is common to liver diseases of many etiologies, including chronic viral hepatitis B and C, autoimmune liver disease such as autoimmune hepatitis, alcoholic liver disease, fatty liver disease; primary biliary cirrhosis; and drug-induced liver disease. The fibrosis seen in these disorders results from chronic insults to the liver such as viral infection, alcohol or drugs.

Hepatitis C, for example, is one of the leading causes of chronic liver disease in the United States, where an estimated 3.9 million people are chronically infected with hepatitis C virus (HCV) and approximately 30,000 new cases of acute HCV occur each year (Alter, *Semin. Liver Dis.* 15:5–14 (1995)). The prevalence of hepatitis C is estimated to be 1.8% in the United States, with up to 10,000 deaths per year likely resulting from chronic hepatitis C infection (Alter, supra, 1995).

While hepatic fibrosis is a reversible process resulting in the accumulation of extracellular matrix, liver cirrhosis is an irreversible process characterized by thick bands of matrix which completely encircle the parenchyma to form nodules. Untreated, fibrosis of the liver leads to cirrhosis and eventually end-stage liver disease or cancer. Cirrhosis of the liver is a common condition that frequently goes undetected. For example, in a large sample of the general Danish population, the prevalence of liver cirrhosis was 4.5%, of which one-third were undiagnosed at the time of death (Graudal, *J. Intern. Med.* 230:165–171 (1991)).

Timely and accurate diagnosis of liver fibrosis is important to effective medical treatment. As an example, patients with hepatitis C and cirrhosis are less likely to respond to treatment with α-interferon compared to patients with less advanced disease (Davis, *Hepatology* 26(Supp. 1):122–127S). Similarly, treatments for chronic HCV infection can be contra-indicated in patients with histologically advanced and decompensated disease (NIH Consensus Development Conference Panel Statement, *Hepatology* 26 (Suppl. 1):25–105S (1997)). The importance of early diagnosis is further emphasized by the serious early complications such as variceal rupture that are associated with cirrhosis; these complications can be prevented by early detection of cirrhosis (Calés and Pasqual, *Gastroenterol. Clin. Biol.* 12:245–254 (1988)).

Diagnosis of the presence or severity of fibrotic liver disease is difficult, with liver biopsy currently the most reliable method available. Unfortunately, liver biopsy has several limitations: pain in about 30% of patients; the risk of severe complications such as hemorrhage or infection; a death rate of 3 in 10,000; and the cost of hospitalization (Nord, *Gastrointest. Endosc.* 28:102–104 (1982); Cadranel et al., *Hepatology* 32:47–481 (2000); and Poynard et al., *Can. J. Gastroenterol.* 14:543–548 (2000)). Furthermore, slowly progressive diseases such as hepatitis C require repeated biopsies for continual assessment of disease progression, thus compounding the risks and costs of the procedure. Finally, biopsy can fail to detect disease because of the heterogeneous distribution of pathological changes in the liver; it is not surprising, then, that false negatives are seen in a significant percentage of cases biopsied (Nord, supra, 1982).

For years there has been a search for biochemical or serological markers which reflect fibrotic processes in liver disease and which can serve as a surrogate for liver biopsy. However, the performance of any single marker has not been good enough to substitute for the biopsy procedure in detecting or staging fibrosis. Thus, there is a need for a non-invasive method of diagnosing the presence or severity of liver fibrosis. The present invention satisfies this need by providing a convenient and reliable method for detection of liver fibrosis that is suitable for serial testing. Related advantages are provided as well.

SUMMARY OF THE INVENTION

The present invention provides a method of diagnosing the presence or severity of liver fibrosis in an individual by detecting α2-macroglobulin (α2-MG) in a sample from the individual; detecting hyaluronic acid (HA) in a sample from the individual; detecting tissue inhibitor of metalloproteinases-1 (TIMP-1) in a sample from the individual; and diagnosing the presence or severity of liver fibrosis in the individual based on the presence or level of α2-MG, HA and TIMP-1. A method of the invention can be useful, for example, for differentiating no or mild (F0–F1) liver fibrosis from moderate to severe (F2–F4) liver fibrosis.

The methods of the invention for diagnosing the presence or severity of liver fibrosis can be useful in a variety of patient populations including, but not limited to, those with viral hepatitis, autoimmune liver disease such as autoimmune hepatitis, alcoholic liver disease, fatty liver disease and drug-induced liver disease. In one embodiment, a method of the invention is used to diagnose the presence or severity of liver fibrosis in an individual infected with hepatitis C virus.

A variety of means can be useful for detecting α2-MG, HA and TIMP-1 in a sample. In one embodiment, the invention is practiced by determining the level of α2-MG protein in a sample from the individual to be diagnosed using, for example, one or more α2-MG-specific binding agents such as anti-α2-MG antibodies. In another embodiment, a method of the invention is practiced by determining the level of α2-MG activity in a sample from the individual.

A variety of means also can be used in a method of the invention to detect hyaluronic acid in a sample. In one embodiment, the invention is practiced by determining the level of HA in a sample, for example, using one or more HA-specific binding agents such as HA-binding proteins (HABPs) or anti-HA antibodies.

Similarly, a variety of means can be used in a method of the invention to detect TIMP-1 in a sample. In one embodiment, the invention is practiced by determining the level of TIMP-1 protein in a sample from the individual to be diagnosed. The level of TIMP-1 protein can be determined, for example, using one or more TIMP-1-specific binding agents such as anti-TIMP-1 antibodies. In another embodiment, the invention is practiced by assaying for TIMP-1 activity in a sample from the individual to be diagnosed.

The invention provides, for example, a method of diagnosing the presence or severity of liver fibrosis in an individual by determining the level of α2-MG protein in a sample from the individual; determining the level of HA in a sample from the individual; and determining the level of TIMP-1 protein in a sample from the individual; and diagnosing the presence or severity of liver fibrosis in the individual based on the levels of α2-MG protein, HA and TIMP-1 protein. If desired, the level of α2-MG protein, HA and TIMP-1 protein each can be determined using an enzyme-linked assay.

A variety of samples can be useful in practicing the methods of the invention including, for example, blood, serum, plasma, urine, saliva and liver tissue. In one embodiment, a single sample is obtained from the individual to be diagnosed. Such a sample can be, for example, a serum sample. Such a sample also can be, for example, a tissue sample, for example, a liver biopsy sample.

The present invention further provides a method of differentiating no or mild liver fibrosis from moderate to severe liver fibrosis in an individual. The method includes the steps of contacting an appropriate dilution of a sample from the individual with anti-α2-MG antibody under conditions suitable to form a first complex of α2-MG and anti-α2-MG antibody; washing the first complex to remove unbound molecules; determining the amount of α2-MG-containing first complex; contacting an appropriate dilution of a sample from the individual with a HA-binding protein under conditions suitable to form a second complex of HA and HA-binding protein; washing the second complex to remove unbound molecules; determining the amount of HA-containing second complex; contacting an appropriate dilution of a sample from the individual with anti-TIMP-1 antibody under conditions suitable to form a third complex of TIMP-1 and anti-TIMP-1 antibody; washing the third complex to remove unbound molecules; determining the amount of TIMP-1-containing third complex; and differentiating no or mild liver fibrosis from moderate to severe liver fibrosis in the individual based on the amounts of α2-MG, HA and TIMP-1-containing complexes.

The methods of the invention can be practiced by detecting the three markers α2-MG, HA and TIMP-1, without detecting additional serological markers, or can be combined with a detection method for one or more additional markers. Thus, in one embodiment, the invention is practiced by detecting α2-MG, HA and TIMP-1 and also detecting at least one of the following markers of fibrosis: N-terminal procollagen III propeptide (PIIINP), laminin, tenascin, collagen type IV, collagen type VI, YKL-40, MMP-3, MMP-2, MMP-9/TIMP-1 complex, sFas ligand, TGF-β1, IL-10, apoA1, apoA2 or apoB. In a further embodiment, the presence or severity of liver fibrosis is diagnosed by detecting α2-MG, HA, TIMP-1 and YKL-40 in a sample from an individual.

The present invention also provides a method of monitoring the efficacy of anti-fibrotic therapy in a patient by detecting α2-macroglobulin in a sample from a patient administered an anti-fibrotic therapy; detecting hyaluronic acid (HA) in a sample from the patient; detecting tissue inhibitor of metalloproteinases-1 (TIMP-1) in a sample from the patient; and determining the presence or severity of liver fibrosis in the patient based on the presence or level of α2-MG, HA and TIMP-1, thereby monitoring the efficacy of anti-fibrotic therapy. Such a method can further include, if desired, comparing the presence or severity of liver fibrosis determined in step (d) to the presence or severity of liver fibrosis in the patient at an earlier time. The methods of the invention can be used to monitor, for example, the progression or regression of fibrosis over time in a patient treated with one or more anti-fibrotic therapies, or to compare, for example, the efficacies of two or more anti-fibrotic therapies.

In one embodiment, at most three markers of fibrosis are detected. In another embodiment, the method includes the step of detecting in a sample from the patient at least one marker selected from the group consisting of: PIIINP, laminin, tenascin, collagen type IV, collagen type VI, YKL-40, MMP-3, MMP-2, MMP-9/TIMP-1 complex, sFas ligand, TGF-β1, IL-10, apoA1, apoA2, and apoB.

A variety of means can be useful for detecting α2-MG, HA and TIMP-1 in a method of the invention. Step (a) can be practiced, for example, by determining the level of α2-MG protein in the sample. In one embodiment, the level of α2-MG protein is determined using one or more anti-α2-MG antibodies. Step (b) can be practiced, for example, by determining the level of HA in the sample. In one embodiment, the level of HA is determined using one or more HA-binding proteins. Step (c) can be practiced, for example, by determining the level of TIMP-1 protein in said sample. In one embodiment, the level of TIMP-1 protein is determined using one or more anti-TIMP-1 antibodies.

Further provided herein is a method of differentiating no or mild liver fibrosis from moderate to severe liver fibrosis in an individual by determining an α2-MG level in a sample from the individual; determining a HA level in a sample from the individual; determining a TIMP-1 level in a sample from the individual; and diagnosing the individual as having no or mild liver fibrosis when the α2-MG level is below an α2-MG cut-off value X1, the HA level is below a HA cut-off value Y1 or the TIMP-1 level is below a TIMP-1 cut-off value Z1; diagnosing the individual as having moderate to severe liver fibrosis when the α2-MG level is above an α2-MG cut-off value X2, the HA level is above a HA cut-off value Y2 and the TIMP-1 level is above a TIMP-1 cut-off value Z2; and diagnosing remaining individuals as having an indeterminate status.

The methods of the invention based on dual cut-off values for the levels of the α2-MG, HA and TIMP-1 markers can be useful in differentiating no or mild liver fibrosis from moderate to severe liver fibrosis in a variety of patient populations. The methods of the invention can be useful, for example, in diagnosing an individual having a liver disease such as viral hepatitis, autoimmune liver disease such as autoimmune hepatitis, alcoholic liver disease, fatty liver disease or drug-induced liver disease. In one embodiment, the methods of the invention are used to differentiate no or mild liver fibrosis from moderate to severe liver fibrosis in an individual infected with hepatitis C virus. Samples useful in the methods of the invention include, but are not limited to, blood, serum, plasma, urine, saliva and liver tissue. In one embodiment, a method of the invention is practiced by determining the α2-MG level, HA level and TIMP-1 level in one or more serum samples from the individual to be diagnosed.

Thus, the present invention provides, for example, a method of differentiating no or mild liver fibrosis from moderate to severe liver fibrosis in an individual in which the differentiation is based on an X1 cut-off value between 1.8 and 2.2 mg/ml; a Y1 cut-off value between 31 and 39 ng/ml; a Z1 cut-off value between 900 and 1100 ng/ml; an X2 cut-off value between 1.8 and 2.2 mg/ml; a Y2 cut-off value between 54 and 66 ng/ml; and a Z2 cut-off value between 1415 and 1735 ng/ml. In a particular embodiment, the differentiation is based on an X1 cut-off value of 2.0 mg/ml; a Y1 cut-off value of 35 ng/ml; a Z1 cut-off value of 1000 ng/ml; an X2 cut-off value of 2.0 mg/ml; a Y2 cut-off value of 60 ng/ml; and a Z2 cut-off value of 1575 ng/ml. In another embodiment, the differentiation is based on an X1 cut-off value of 2.0 mg/ml; a Y1 cut-off value of 37 ng/ml; a Z1 cut-off value of 1100 ng/ml; an X2 cut-off value of 2.0 mg/ml; a Y2 cut-off value of 60 ng/ml; and a Z2 cut-off value of 1575 ng/ml. In a further embodiment, X1, Y1, Z1, X2, Y2 and Z2 are selected such that, in a population having up to 30% liver fibrosis prevalence, at least 65% of individuals in the population are diagnosed as having no/mild fibrosis or moderate/severe fibrosis with an accuracy of at least 90%. In another embodiment, X1, Y1, Z1, X2, Y2 and Z2 are selected such that, in a population having up to 30% liver fibrosis prevalence, at least 65% of individuals in said population are diagnosed as having no/mild fibrosis or moderate/severe fibrosis with a positive predictive value of at least 90% and a negative predictive value of at least 90%. In yet a further embodiment, X1, Y1, Z1, X2, Y2 and Z2 are selected such that, in a population having up to 10% fibrosis prevalence, at least 70% of individuals in the population are diagnosed as having no/mild fibrosis or moderate/severe fibrosis with an accuracy of at least 90%.

The present invention also provides a method of diagnosing the presence or severity of liver fibrosis in an individual by comparing a level of a first fibrotic marker X in the individual to a cut-off value X1 to determine whether the individual is positive for the first fibrotic marker X; comparing a level of a second fibrotic marker Y in the individual to a cut-off value Y1 to determine whether the individual is positive for the second fibrotic marker Y; and diagnosing the presence or severity of liver fibrosis in the individual based on positivity or negativity for X and Y, where, in a population with up to 40% fibrosis prevalence, at least 65% of individuals in the population are diagnosed with an accuracy of at least 90%.

A method of the invention can include, if desired, comparing a level of a third fibrotic marker Z in the individual to a cut-off value Z1 to determine whether the individual is positive for the third fibrotic marker Z and diagnosing the presence or severity of liver fibrosis in the individual based on positivity or negativity for X, Y and Z. In one embodiment, the first fibrotic marker is $\alpha$2-MG, the second fibrotic marker is HA, and the third fibrotic marker is TIMP-1.

In another embodiment, the levels of at least three fibrotic markers are compared, and, in a further embodiment, the levels of exactly three fibrotic markers are compared. In additional embodiments, the levels of at least four or at least five fibrotic markers are compared. A method of the invention can be useful, for example, to differentiate no or mild liver fibrosis from moderate to severe liver fibrosis.

In a specific embodiment, a method of the invention serves to diagnose at least 65% of individuals in a population with up to 30% fibrosis prevalence with an accuracy of at least 93%. In a further embodiment, a method of the invention serves to diagnose at least 70% of individuals in a population with up to 20% fibrosis prevalence with an accuracy of at least 94%. In yet a further embodiment, a method of the invention serves to diagnose at least 70% of individuals in a population with up to 10% fibrosis prevalence with an accuracy of at least 96%.

The present invention further provides a method of diagnosing the presence or severity of liver fibrosis in an individual by comparing a level of a first fibrotic marker X in the individual to a cut-off value X1 to determine whether the individual is positive for the first fibrotic marker X; comparing a level of a second fibrotic marker Y in the individual to a cut-off value Y1 to determine whether the individual is positive for the second fibrotic marker Y; and diagnosing the presence or severity of liver fibrosis in the individual based on positivity or negativity for X and Y, where the cut-off values X1 and Y1 are optimized individually to give a desired performance characteristic.

If desired, a method of the invention can include the steps of comparing a level of a third fibrotic marker Z in the individual to a cut-off value Z1 to determine whether the individual is positive for the third fibrotic marker Z and diagnosing the presence or severity of liver fibrosis in the individual based on positivity or negativity for X, Y and Z, where the cut-off values X1, Y1 and Z1 are optimized individually to give a desired performance characteristic. In one embodiment, levels of $\alpha$2-MG, HA and TIMP-1 are compared. In another embodiment, the cut-off values are optimized using design of experiments (DOE) analysis. In further embodiments, the levels of exactly three, at least three, at least four, or at least five fibrotic markers are compared. A method of the invention can be useful, for example, in differentiating no or mild liver fibrosis from moderate to severe liver fibrosis.

Further provided by the invention is a method of diagnosing the presence or severity of liver fibrosis in an individual by comparing a level of a first fibrotic marker X in the individual to two cut-off values X1 and X2 to determine whether the individual is positive for the first fibrotic marker X; comparing a level of a second fibrotic marker Y in the individual to two cut-off values Y1 and Y2 to determine whether the individual is positive for the second fibrotic marker Y; and diagnosing the presence or severity of liver fibrosis in the individual based on positivity or negativity for X and Y, where the cut-off values X1, Y1, X2 and Y2 are optimized individually to give a desired performance characteristic. A method of the invention can further include the steps of comparing a level of a third fibrotic marker Z in the individual to two cut-off values Z1 and Z1 to determine whether the individual is positive for the third fibrotic marker Z; and diagnosing the presence or severity of liver fibrosis in the individual based on positivity or negativity for X, Y and Z, where the cut-off values X1, Y1, Z1, X2, Y2 and Z2 are optimized individually to give a desired performance characteristic. Cut-off values can be conveniently optimized, for example, using DOE analysis.

BRIEF DESCRIPTION OF THE DRAWINGS

FIG. 1 shows the nucleic acid sequence (SEQ ID NO: 1) and corresponding amino acid sequence (SEQ ID NO: 2) for mature human $\alpha$2-macroglobulin available from Genbank accession M36501.

FIG. 2 shows the nucleic acid sequence (SEQ ID NO: 3) and corresponding amino acid sequence (SEQ ID NO: 4) for human tissue inhibitor of metalloproteinases-1 (TIMP-1) available from Genbank accession NM_003254.

DETAILED DESCRIPTION OF THE INVENTION

As disclosed herein, the serum levels of a number of biochemical markers were analyzed in a patient population with confirmed hepatitis C and having a known Metavir stage (fibrosis score) of F0 to F4, where F0 represents very low or no fibrosis; F1, F2 and F3 represent intermediate fibrosis stages; and F4 represents severe fibrosis (Knodell et al., *Hepatology* 1:431–435 (1981)). See Tables 2 and 3.

Using Design of Experiments (DOE) analysis for simultaneous variation of multiple cut-off values, a four-marker panel made up of hyaluronic acid (HA), PIIINP, collagen type IV and α2-macroglobulin (α2-MG) was identified which was capable of differentiating F0–F1 (no or mild) fibrosis from F2–F4 (moderate to severe) fibrosis with an accuracy of about 77% in a patient population with a fibrosis prevalence of 60%.

As further disclosed herein in Example I, two three-marker panels, α2-MG/HA/TIMP-1 and α2-MG/HA/YKL-40, also performed well in differentiating F0–F1 fibrosis from F2–F4 fibrosis when cut-offs were optimized using DOE analysis. In particular, the α2-MG/HA/TIMP-1 and α2-MG/HA/YKL-40 panels each performed better than the four-marker panel and were capable of differentiating F0–F1 from F2–F4 fibrosis with about 80% accuracy in the study population. As can be seen in Table 6, line 15, for example, the α2-MG/HA/TIMP-1 panel performed with a sensitivity of 83.48% and a specificity of 75.95% in the study population having 60% fibrosis prevalence. These results demonstrate that the α2-MG/HA/TIMP-1 three-marker panel can be useful for differentiating no or mild fibrosis from moderate to severe fibrosis.

Based on these findings, the present invention provides a method of diagnosing the presence or severity of liver fibrosis in an individual by detecting α2-MG in a sample from an individual; detecting HA in a sample from the individual; detecting TIMP-1 in a sample from the individual; and diagnosing the presence or severity of liver fibrosis in the individual based on the presence or levels of α2-MG, HA and TIMP-1. A method of the invention can be useful, for example, for differentiating no or mild (F0–F1) liver fibrosis from moderate to severe (F2–F4) liver fibrosis.

Liver and Other Fibrotic Disorders

The methods of the invention can be useful for diagnosing the presence or severity of liver fibrosis in a variety of individuals including those at risk for, or having one or more symptoms of, a liver disorder characterized by fibrosis. The methods of the invention can be used to diagnose liver fibrosis in an individual having, for example, viral hepatitis such as hepatitis A, B or C virus or a human immunodeficiency virus (HIV) such as HIV-1; chronic persistent hepatitis or chronic active hepatitis; autoimmune liver disease such as autoimmune hepatitis; alcoholic liver disease; fatty liver disease; primary biliary cirrhosis; primary sclerosing cholangitis, biliary atresia; liver disease resulting from medical treatment (drug-induced liver disease); or a congenital liver disease. The methods of the invention can be extremely useful, for example, in alleviating concerns of potential liver damage due to methotrexate treatment. Periodic monitoring of liver fibrosis in individuals treated with methotrexate or other drugs associated with risk of liver damage can be conveniently performed using the non-invasive methods of the invention, without the risks associated with liver biopsy.

In one embodiment, the methods of the invention are useful for differentiating individuals having a Metavir score of F0 or F1 from individuals having a Metavir score of F2, F3 or F4. Metavir scoring is a well accepted system for grading liver biopsy specimens and is described in Knodell, supra, 1981. F0 is equivalent to the absence of fibrosis; F1 signifies portal fibrosis without septa. F2 signifies portal fibrosis with a few septa. F3 signifies numerous septa without cirrhosis. F4 signifies cirrhosis.

It is understood that the methods of the invention are useful for diagnosing the presence or severity of fibrosis associated with a variety of fibrotic disorders, including but not limited to liver fibrosis, pulmonary fibrosis, kidney fibrosis, prostate fibrosis and breast fibrosis. The methods of the invention can be applied, without limitation, to diagnosing the presence or severity of pulmonary fibrosis, for example, idiopathic pulmonary fibrosis or emphysema; kidney fibrosis; bladder fibrosis; periureteric fibrosis or retroperitoneal fibrosis; endomyocardial fibrosis, aortic aneurysm disease; rheumatoid diseases such as rheumatoid arthritis or systemic lupus erythematosus; or another fibrotic disorder such as Alzheimer's disease. It is understood that a α2-MG/HA/TIMP-1 , α2-MG/HA/YKL-40 or α2-MG/HA/TIMP-1/YKL-40 panel or other combination of markers disclosed herein as useful for diagnosing the presence or severity of liver fibrosis also can be used to diagnose the presence or severity of fibrosis in another disorder.

It is understood that the diagnostic methods of the invention are applicable to a variety of individuals including individuals with chronic or active disease, individuals with one or more symptoms of fibrotic disease, asymptomatic or healthy individuals and individuals at risk for one or more fibrotic diseases. It further is clear to the skilled person that the methods of the invention can be useful, for example, to corroborate an initial diagnosis of disease or to gauge the progression of fibrosis in an individual with a previous definitive diagnosis of fibrotic disease. The methods of the invention can be used to monitor the status of fibrotic disease over a period of time and further can be used, if desired, to monitor the efficacy of therapeutic treatment. If desired, the results obtained from a sample from an individual undergoing therapy can be compared, for example, to the individual's baseline results prior to treatment, to results earlier during treatment, or to a historic or reference value.

Samples

A variety of samples can be useful in practicing the methods of the invention including, for example, blood, serum, plasma, urine, saliva and liver tissue. In one embodiment, a single sample is obtained from the individual to be diagnosed. Such a sample can be, for example, a serum sample.

As used herein, the term "sample" means a biological specimen that contains one or more fibrotic markers such as α2-MG, HA or TIMP-1. A sample can be, for example, a fluid sample such as whole blood, plasma, saliva, urine, synovial fluid or other bodily fluid, or a tissue sample such as a lung, liver, kidney, prostate or breast tissue sample. One skilled in the art understands that fluid samples can be diluted, if desired, prior to analysis.

One skilled in the art understands that a single sample can be obtained from the individual to be diagnosed and can be subdivided prior to detecting α2-MG-, HA- and TIMP-1. One skilled in the art also understands that, if desired, two or more samples can be obtained from the individual to be diagnosed and that the samples can be of the same or a different type. In one embodiment, α2-MG-, HA- and TIMP-1 each are detected in serum samples. In another embodiment, a single serum sample is obtained from an individual and subdivided prior to detecting α2-MG-, HA- and TIMP-1.

α2-Macroglobulin

The methods of the invention rely, in part, on detecting α2-macroglobulin in a sample. α2-MG is a conserved, highly abundant component of plasma that functions as a broad spectrum protease-binding protein to clear active proteases from tissue fluids. Unlike active site protease inhibitors, members of the α2-macroglobulin family do not inactivate the catalytic activity of their protease substrates but act by physical entrapment of the target protease within the folds of the α2-MG family member. α2-MG is itself cleaved by target proteases; reorganization of the α2-MG molecule results in sequestering of the target protease within an internal pocket of the α2-MG molecule (Starkey et al., *Biochem. J.* 131:823–831 (1973)). While an α2-MG entrapped protease is sterically prevented from interacting with macromolecular substrates such as proteins, it remains active against low molecular mass substrates, such as amide and ester compounds, able to diffuse into the α2-MG cage to access the enzymatic site. Thus, α2-MG activity is characterized, in part, by the ability to inhibit proteolytic activity but not amidolytic activity of a protease substrate. α2-MG also is characterized by the ability to shield entrapped proteases from antibodies and high molecular mass active site inhibitors. For example, trypsin bound by α2-MG is protected from inhibition by soybean trypsin inhibitor (STI).

In contrast to the restricted specificity of active-site protease inhibitors, α2-MG acts on a broad spectrum of proteases with diverse substrate specificity and catalytic activity. Such target proteases include trypsin, subtilisin, chymotrypsin, plasmin, elastase, thermolysin and papain. Substrate diversity is determined, in part, by the α2-MG "bait" region, a highly flexible and solvent-exposed sequence of 30–40 residues that contains at least one site sensitive to cleavage by each of the major classes of proteolytic enzyme.

As used herein, the term "α2-macroglobulin" is synonymous with "α2-MG" and means a protein with significant structural homology to human α2-MG (SEQ ID NO: 2) and having broad spectrum protease inhibitory activity. α2-MG contains a unique thiol ester bond that is inactivated by small primary amines such as methylamine. Thus, α2-MG activity can be characterized, in part, by methylamine-sensitive protease inhibitory activity. α2-MG can be distinguished, if desired, from other members of the α2-macroglobulin family such as related protease-binding proteins and C3, C4 and C5 of the complement system (Sottrup-Jensen, "α2-Macroglobulin and Related Thiol Ester Plasma Proteins," in Putnam (Ed.), *The Plasma Proteins: Structure, Function and Genetic Control* Second edition, Orlando: Academic Press (1987), pages 191–291. It is understood that an assay for detecting α2-MG can be specific for α2-MG or can additionally detect one or more other members of the α2-macroglobulin family.

The methods of the invention rely, in part, on detecting α2-macroglobulin in a sample. As used herein, the phrase "detecting α2-MG" means any quantitative or qualitative assay for determining the presence of α2-MG. As used herein, the phrase "determining the level of α2-MG" means any direct or indirect quantitative assay for α2-MG.

Similarly, detecting any specified fibrotic marker in a sample means determining whether the marker is present in the sample, said fibrotic marker having a positive or negative correlation with liver fibrosis or with another fibrotic disorder such as are described herein above. It is understood that detection can refer to non-quantitative analysis, for example, the presence or absence of a particular trait, variable or biochemical or serological substance.

Diagnosis is based on analyzing the sample for the presence or level of the fibrotic marker or other characteristic and comparing it to a reference value, where the reference value serves to assist in differentiating those with a fibrotic disorder from other individuals. Where the fibrotic marker is a biochemical or serological marker, determining a "level" in a sample means quantifying the fibrotic marker by determining, for example, the relative or absolute amount of RNA, protein or activity of the fibrotic marker. Thus, determining a level in a sample encompasses, without limitation, analysis of relative and absolute RNA, protein and activity levels as well as other direct and indirect measurements of the fibrotic marker as discussed further below. It is understood that any assay useful for determining a "level" of a fibrotic marker also is useful for "detecting" the marker.

A variety of assays for detecting α2-MG are known in the art and include direct and indirect assays for α2-MG RNA, α2-MG protein and α2-MG activity. α2-MG can be detected, or an α2-MG level can be determined, for example, by analysis of α2-MG mRNA levels using routine techniques such as Northern analysis or RT-PCR, or other methods based on hybridization to a nucleic acid sequence that is complementary to a portion of the α2-MG coding sequence. For example, conditions and probes for Northern analysis and RNA slot blot hybridization of α2-MG RNA in human samples are described in Ortego et al., *Exp. Eye Res.* 65:289–299 (1997), and Simon et al., *Cancer Res.* 56:3112–3117 (1996), respectively.

α2-MG also can be detected, or an α2-MG level can be determined, by assaying for α2-MG protein by a variety of methods. Immunoassays, including radioimmunoassays, enzyme-linked immunoassays and two-antibody sandwich assays as described further below, are useful in the methods of the invention. For example, in nephelometry assays, complexes of α2-MG and anti-α2-MG antibody result in increased light scatter that is converted to a peak rate signal, which is a function of the sample α2-MG concentration. α2-MG also can be detected, for example, by laser immunonephelometry using a Behring Nephelometer Analyzer (Fink et al., *J. Clin. Chem. Clin. Biol. Chem.* 27:261–276 (1989)) and rabbit anti-human α2-MG antiserum as described in Naveau et al., *Dig. Diseases Sci.* 39:2426–2432 (1994), or using the nephelometry assay commercially available from Beckman Coulter (Brea, Calif.; kit #449430). Furthermore, monoclonal and polyclonal anti-α2-MG antibodies useful in immunoassays can be readily obtained from a variety of sources. As examples, affinity purified goat anti-human α2-MG and peroxidase-labeled goat anti-human α2-MG antibodies suitable for immunoassays such as ELISA assays and western blotting are available from Cedarlane Laboratories Limited (Ontario, Canada; CL20010AP and CL20010APHP) and Affinity Biologicals Incorporated (Ontario, Canada; GAA2M-AP and GAA2M-APHRP). Levels of α2-MG protein also can be determined by quantifying the amount of purified α2-MG protein. Purification of α2-macroglobulin can be achieved, for example, by HPLC, alone or in combination with mass spectrophotometry, or as described, for example, in Hall and Roberts, *Biochem. J.* 171:27–38 (1978) or Imber and Pezzo, *J. Biol. Chem.* 256:8134–8139 (1981)). Quantitation can be determined by well known methods including Bradford assays, Coomassie blue staining and assays for radiolabeled protein.

A variety of assays for α2-MG activity also can be useful for detecting α2-MG or determining a level of α2-MG in a sample according to a method of the invention. α2-MG can be detected or a level of α2-MG can be determined indirectly, for example, as a function of inhibition of target protease activity, without a corresponding inhibition of amidolytic activity. As discussed above, α2-MG-bound proteases retain the ability to hydrolyze amide and ester bonds of small substrates, even while high molecular mass substrates such as proteins cannot be hydrolyzed (see, for example, Armstrong et al., *Develop. Compar. Immunol.* 23:375–390 (1999)). As an example, α2-MG can be detected or the level of α2-MG can be determined by assaying for inhibition of trypsin, subtilisin, chymotrypsin, plasmin, elastase, thermolysin, or papain activity without inhibition of amidolytic activity. Convenient substrates to be analyzed include $^{14}$C-labeled casein and $^{125}$I-fibrin.

The characteristic of broad protease substrate specificity distinguishes α2-MG from inhibitors of protease active sites. Based on this characteristic, α2-MG can be detected or the level of α2-MG can be determined by assaying for inhibition of the activity of two or more proteases with different active site specificities. α2-MG can be detected or the level of α2-MG in a sample can be determined, for example, by analyzing the reduction in protease activity of two or more target proteases such as two or more of the following proteases: trypsin, subtilisin, chymotrypsin, plasmin, elastase, thermolysin and papain. Labeled protease substrates such as $^{14}$C-casein or $^{125}$I-fibrin can be useful in such methods (Armstrong et al., supra, 1999).

α2-MG also can be detected or the level of α2-MG determined based on the ability of α2-MG to shield a bound protease from an antibody or a high molecular weight inhibitor. A target protease such as trypsin, subtilisin, chymotrypsin, plasmin, elastase, thermolysin, or papain can be added to a plasma sample. Following removal of unbound protease, for example, by immunoprecipitation with anti-protease antibody, the amount of protease bound by α2-MG can be determined using a low molecular mass amide or ester substrate. The amount of hydrolyzed low molecular mass substrate is an indicator of the amount of protected, α2-MG-bound, protease and, therefore, of the concentration of α2-MG. Similarly, a sample can be reacted first with a protease such as trypsin and subsequently with excess protease inhibitor such as soybean trypsin inhibitor before assaying residual trypsin activity with a low molecular mass substrate, such as the amide BApNA (N$^\alpha$-benzoyl-DL-arginine p-nitroanilide (Ganrot, *Clin. Chem. Acta* 14:493–501 (1966); Armstrong et al., *J. Exp. Zool.* 236:1–9 (1985)). Trypsin not sequestered by α2-MG is inactivated by the trypsin inhibitor, with only α2-MG-protected trypsin remaining capable of substrate hydrolysis. Thus, a positive reaction in a soybean trypsin inhibitor assay detects α2-MG and is a quantitative measure of the amount of α2-MG (Armstrong et al., supra, 1999). One skilled in the art understands that the presence of low molecular mass protease inhibitors capable of inactivating α2-MG-bound enzyme can affect the results obtained with such an assay. It is further understood that these and other routine assays for α2-MG activity, as well as α2-MG RNA or protein levels, can be useful for detecting α2-MG or determining a level of α2-MG in a method of the invention.

Hyaluronic Acid

The methods of the invention further rely, in part, on detecting hyaluronic acid or determining a level of hyaluronic acid in a sample. Hyaluronic acid, also known as hyaluronate or hyaluronan, is a high molecular weight polysaccharide with an unbranched backbone made up of alternating glucuronic acid and β(1,3)-N-acetylglucosamine moieties linked by β-1,4 linkages. Hyaluronic acid can have a length of a few to more than 1,000 dimeric units, with each dimeric unit having a molecular weight of about 450 D. Hyaluronic acid, which is produced principally by fibroblasts and other specialized connective tissue cells, plays a structural role in the connective tissue matrix. Furthermore, hyaluronic acid is widely distributed throughout the body and can be found as a free molecule in, for example, plasma, synovial fluid and urine. In plasma, hyaluronic acid has a relatively short half-life.

Serum HA levels can be elevated in liver diseases including cirrhosis (Bramley et al., *J. Hepatol.* 13:8–13 (1991); Ueno et al., *Gastroenterol.* 105:475–481 (1993); Oberti et al., *Gastroenterol.* 113:1609–1616 (1997); and McHutchison et al., *J. Gastroenterol. Hepatol.* 15:945–951 (2000)). Serum HA levels also can be elevated during synovial inflammation and cartilage destruction seen in rheumatoid arthritis; these levels have been found to correlate with disease activity and degree of synovial involvement (Konttinen et al., *Clin. Chimica Acta* 193:39–48 (1990); Poole et al., *Arthritis Rheum.* 37:1030–1038 (1994); Goldberg et al., *Arthritis Rheum.* 34: 799–807 (1991); and Emlem et al., *J. Rheum.* 23:974–978 (1996)). Elevated serum levels of HA also can be present, for example, in patients with osteoarthritis (OA), progressive systemic sclerosis (PSS) and systemic lupus erythematosus (SLE).

As used herein, the term "hyaluronic acid" is synonymous with "HA" and means a polymer of two or more dimeric units of alternating glucuronic acid and β(1,3)-N-acetylglucosamine moieties linked by β-1,4 linkages. As used herein, the phrase "detecting HA" means any quantitative or qualitative assay for determining the presence of HA, and the phrase "determining the level of HA" means any direct or indirect quantitative assay for HA. In view of the above, it is understood that the phrase "detecting HA" encompasses "determining the level of HA."

HA can be detected or a level of HA can be determined using one of a variety of well known assays based on HA-binding proteins or anti-HA antibodies, or by quantitation of purified HA. HA-binding proteins, for example, can be useful in detecting HA; a radiometric assay for HA based on $^{125}$I-labelled HA-binding protein is available from Pharmacia (Guechot et al., *Clin. Chem.* 42:558–563 (1996). Other commercial assays based on HA-binding proteins are available, for example, from Corgenix (Westminster, Conn.; kit 029001). In addition, HA can be detected or a level of HA can be determined using hyaluronectin as described in Maingonnat and Delpech, *Ann. Clin. Biochem.* 28:305–306 (1991), or using the kit available from Nalgenunc International (Rochester, N.Y.; Delpech and Bertrand, *Anal. Biochem.* 149:555–565 (1985)). Assays for detecting HA or determining a level of HA include a variety of competitive and non-competitive binding assays, for example, competitive binding assays using $^{125}$I-labeled HA binding protein; competitive binding assays based on alkaline phosphatase labeled-hyaluronectin (HN); and non-competitive binding assays based on peroxidase-labeled proteoglycan or peroxidase-labeled HA-binding protein, among others (Lindquist et al., *Clin. Chem.* 38:127–132 (1992)). See, also, Delpech and Bertrand, supra, 1985; Engstrom-Laurent et al., *Scand. J. Clin. Lab. Invest.* 45:497–504 (1985); Brandt et al., *Acta Otolaryn.* 442 (Suppl.):31–35 (1987); Goldberg, *Anal. Biochem.* 174:448–458 (1988); Chichibu et al., *Clin. Chim. Acta* 181:317–324 (1989); Li et al., *Conn. Tissue Res.* 19:243–254 (1989); Poole et al., *Arth. Rheum.* 33:790–799 (1990); Poole et al., *J. Biol. Chem.* 260:6020–6025 (1985); and Laurent and Tengblad, *Anal. Biochem.* 109:386–394 (1980)). Assays for detecting HA or determining a level of HA in a sample can be performed using a variety of immunoassay formats, including radioimmunoassays and enzyme-linked immunoassays. Anti-HA antiserum useful in immunoassays can be, for example, affinity purified sheep anti-HA antiserum available from Biotrend (Cologne, Germany; #5029-9990).

A level of HA also can be determined by purifying HA from a sample, and quantifying the amount of purified polysaccharide. High performance liquid chromatography can be used alone or in conjunction with mass spectrophotometry. As an example, HPLC can be used to determine HA levels after digestion of samples containing an internal standard with hyaluronidase, separation by a reversed phase octadecylsilyl column and elution with 0.01 M tetrabutylammonium phosphate-acetonitrile (83:17, v/v) at pH 7.35 (Payan et al., *J. Chromatogr.* 566:9–18 (1991)).

HA levels have been shown to correlate with hyaluronidase levels (Bray et al., *Am. Rev. Respir. Dis.* 3:284–288 (1991)). Thus, HA can be detected or a level of HA can be determined indirectly by assaying for hyaluronidase activity. Assays for hyaluronidase activity are known in the art, as described in Bray et al., supra, 1991. One skilled in the art understands that these and other routine assays for determining hyaluonidase or HA levels are encompassed by the phrases "detecting HA" and "determining the level of HA" and can be useful in diagnosing the presence or severity of liver fibrosis according to a method of the invention.

TIMP-1

The methods of the invention also are based on detecting TIMP-1 in a sample and, in particular embodiments, on determining a level of TIMP-1 in a sample. Tissue inhibitors of metalloproteinases (TIMPs) regulate the activity of the matrix metalloproteinases (MMPs), which are an important group of ECM-degradative enzymes that include gelatinase A (MMP-2) and gelatinase B (MMP-9). In normal liver, matrix components such as collagens, fibronectin, laminin, tenascin, undulin and entactin are constantly remodeled by matrix degrading enzymes to control deposition of extracellular matrix. Elevation of TIMP levels results in inhibition of MMP activity and favors the accumulation of extracellular matrix. The TIMPs, which include TIMP-1, TIMP-2, TIMP-3 and TIMP-4, interact with the matrix metalloproteinases with a 1:1 stoichiometry and inhibit metalloprotease activity through reversible non-covalent binding. TIMP-1, TIMP-2 and TIMP-3 have similar MMP-inhibitory activities, inhibiting the proteolytic activity of collagenase, gelatinase, stromelysin, proteoglycanase and metalloelastases although their localization and regulation differ (Cawston et al., "Protein Inhibitors of Metalloproteinases" in Barrett and Salvesen (Eds), *Proteinase Inhibitors* Amsterdam Elsevier pages 589–610 (1986)).

Human TIMP-1 is a 184 amino acid sialoglycoprotein with a molecular weight of 28.5 kDa (Murphy et al., *Biochem. J.* 195:167–170 (1981); Dockerty et al., *Nature* 318:66–69 (1985); and Bodden et al., *J. Biol. Chem.* 269: 18943–18952 (1994)). TIMP-1 inhibits all active metalloproteinases, for example, interstitial collagenase MMP-1 as well as stromelysin and gelatinase B (MMP-9). The nucleic acid sequence (SEQ ID NO: 3) and corresponding amino acid sequence (SEQ ID NO: 4) of human TIMP-1 are shown in FIG. 2.

As used herein, the term "tissue inhibitor of metalloproteinase-1" is synonymous with "TIMP-1" and means a protein with significant structural homology to human TIMP-1 (SEQ ID NO: 4) that inhibits the proteolytic activity of metalloproteinases with a specificity similar to human TIMP-1. The presence of human TIMP-1 can be conveniently detected by the presence of epitopes reactive with a known specific anti-TIMP-1 antibody such as 7-6Cl or 7-23G9.

As used herein, the phrase "detecting TIMP-1" means any quantitative or qualitative assay for determining the presence of TIMP-1, and the phrase "determining the level of TIMP-1" means any direct or indirect quantitative assay for TIMP-1. In view of the above, it is understood that the phrase "detecting TIMP-1" encompasses "determining the level of TIMP-1."

Assays for detecting TIMP-1 and for determining a level of TIMP-1 include well known assays for TIMP-1 RNA, protein and enzymatic activity. Methods of determining TIMP-1 RNA levels by Northern analysis or RT-PCR are well known in the art (Yoshiji et al., *Int. J. Cancer* 69:131–134 (1996); Janowska-Wieczorek et al., *Exp. Hematol.* 28:1274–1285 (2000); and Groft et al., *Br. J. Cancer* 85:55–63 (2001)) as described further below. TIMP-1 protein can be detected or the level of TIMP-1 protein can be conveniently determined, for example, by radioimmunoassay as described in Brophy et al., *Biochem. Biophys. Res. Comm.* 167:898–903 (1990) or by two-antibody sandwich assay as described in Murawaki et al., *Clinica Chimica Acta* 218:47–58 (1993). Plasma concentrations of TIMP-1 protein can be assayed by ELISA with a kit commercially available from Amersham Pharmacia (see, also Example III). Levels of TIMP-1 protein also can be determined by quantifying the amount of purified TIMP-1 protein. Purification of TIMP-1 can be achieved, for example, by HPLC, alone or in combination with mass spectrophotometry, or as described, for example, in Murphy et al., *Biochem. J.* 195:167–170 (1981), or Stricklin and Welgus, *J. Biol. Chem.* 258:12252–12258 (1983). TIMP-1 also can be detected or a level of TIMP-1 determined by assaying for inhibition of the activity of one or more metalloproteases, for example, using reverse gelatin zymography as described in Kossakowska et al., *Amer. J. Pathology* 153:1895–1902 (1998). Assays for TIMP-1 RNA, protein or activity are described further hereinbelow, and one skilled in the art understands that these and other routine assays for detecting TIMP-1 are encompassed by the methods of the invention.

Rule-In/Rule-Out Analysis

As disclosed herein, two sets of cut-off values can be used to increase the accuracy of an assay based on the α2-MG/HA/TIMP-1 three-marker panel. As set forth in Example II, a first set of cut-off values for α2-MG, HA and TIMP-1 were selected based on optimization for sensitivity in order to first rule out fibrosis, followed by analysis of the "positive" population using a second set of cut-off values optimized for specificity to determine the presence of significant fibrosis. Table 7 shows the results of the dual optimization strategy on the 194 HCV patient study population. The primary cut-offs were set at 2.0 mg/ml, 35 ng/ml and 1000 ng/ml for α2-MG, HA and TIMP-1, respectively, to achieve a high sensitivity in the primary analysis. Any samples with all three of α2-MG, HA and TIMP-1 levels above the primary cut-off values were tentatively indicated to be positive for F2–F4 fibrosis and were further evaluated using a second set of cut-off values of 2.0 mg/ml, 60 ng/ml and 1575 ng/ml for α2-MG, HA and TIMP-1, respectively, which were obtained by optimizing for specificity.

Using the second set of cut-off values optimized for high specificity, 54 of the 122 patients initially designated as positive for F2–F4 fibrosis were confirmed positive, only one of which was a false positive. In sum, of the 194 HCV patients in the study population, 72 were classified as negative (having F0–F1 fibrosis) and 54 were classified as positive (having F2–F4 fibrosis), while 68 samples had indeterminate results and were not classified. When the indeterminate samples were excluded, the α2-MG/HA/TIMP-1 panel performed with a positive predictive value of about 98% and a negative predictive value of about 79%. Furthermore, in a more typical patient population having 30% fibrosis prevalence, the same panel performs with positive and negative predictive values of close to 93%. These results indicate that the use of primary and secondary cut-off levels, whereby sensitivity is initially optimized followed by optimization for specificity, can increase the overall accuracy of a three-marker test, resulting in a panel test with about 93% accuracy for non-indeterminate samples, which make up about 70% of the samples tested.

Thus, the present invention provides a method of differentiating no or mild liver fibrosis from moderate to severe liver fibrosis in an individual by determining an α2-MG level in a sample from the individual; determining a HA level in a sample from the individual; determining a TIMP-1 level in a sample from the individual; and diagnosing the individual as having no or mild liver fibrosis when the α2-MG level is below an α2-MG cut-off value X1, the HA level is below a HA cut-off value Y1 or the TIMP-1 level is below a TIMP-1 cut-off value Z1; diagnosing the individual as having moderate to severe liver fibrosis when the α2-MG level is above an α2-MG cut-off value X2, the HA level is above a HA cut-off value Y2 and the TIMP-1 level is above a TIMP-1 cut-off value Z2; and diagnosing remaining individuals as having an indeterminate status.

The methods of the invention based on dual cut-off values for the levels of the α2-MG, HA and TIMP-1 markers can be useful in differentiating no or mild liver fibrosis from moderate to severe liver fibrosis in a variety of patient populations. Such methods can be useful, for example, in diagnosing an individual having a liver disease such as viral hepatitis, autoimmune liver disease such as autoimmune hepatitis, alcoholic liver disease, fatty liver disease or drug-induced liver disease. In one embodiment, a method of the invention is used to differentiate no or mild liver fibrosis from moderate to severe liver fibrosis in an individual infected with hepatitis C virus. Samples useful in a method of the invention based on dual cut-off values include, but are not limited to, blood, serum, plasma, urine, saliva and liver tissue. In one embodiment, a method of the invention is practiced by determining the α2-MG level, HA level and TIMP-1 level in one or more serum samples.

In a further embodiment, the present invention provides a method of differentiating no or mild liver fibrosis from moderate to severe liver fibrosis in an individual, where the differentiation is based on an X1 cut-off value between 1.8 and 2.2 mg/ml; a Y1 cut-off value between 31 and 39 ng/ml; a Z1 cut-off value between 900 and 1100 ng/ml; an X2 cut-off value between 1.8 and 2.2 mg/ml; a Y2 cut-off value between 54 and 66 ng/ml; and a Z2 cut-off value between 1415 and 1735 ng/ml. In another embodiment, the differentiation is based on an X1 cut-off value of 2.0 mg/ml; a Y1 cut-off value of 35 ng/ml; a Z1 cut-off value of 1000 ng/ml; an X2 cut-off value of 2.0 mg/ml; a Y2 cut-off value of 60 ng/ml; and a Z2 cut-off value of 1575 ng/ml. In yet another embodiment, the differentiation is based on an X1 cut-off value of 2.0 mg/ml; a Y1 cut-off value of 37 ng/ml; a Z1 cut-off value of 1100 ng/ml; an X2 cut-off value of 2.0 mg/ml; a Y2 cut-off value of 60 ng/ml; and a Z2 cut-off value of 1575 ng/ml. In a further embodiment, X1, Y1, Z1, X2, Y2 and Z2 are selected such that, in a population having up to 30% liver fibrosis prevalence, at least 65% of individuals in the population are diagnosed as having no or mild fibrosis or moderate to severe fibrosis with an accuracy of at least 90%. In yet a further embodiment, X1, Y1, Z1, X2, Y2 and Z2 are selected such that, in a population having up to 10% liver fibrosis prevalence, at least 70% of individuals in the population are diagnosed as having no or mild fibrosis or moderate to severe fibrosis with an accuracy of at least 90%.

As set forth above, the methods of the invention are highly accurate for determining the presence or severity of fibrosis in a subgroup of the entire patient population assayed. For example, as shown in Table 7, the methods of the invention perform with more than 93% accuracy in determining the F0–F1 or F2–F4 fibrosis status in about 70% of a patient population having a liver fibrosis prevalence of 30%. The remaining 30% of the patient population are indicated to have an indeterminate status. As used herein, the term "indeterminate status" means that the individual cannot be confidently diagnosed with sufficient predictive value.

As used herein, the term "X1" or "X2" refers to an α2-MG cut-off value, against which an experimental α2-MG sample level is compared. Similarly, as used herein, the term "Y1" or "Y2" refers to an HA cut-off value, against which an experimental HA level is compared. The term "Z1" or "Z2," as used herein, refers to a TIMP-1 cut-off value against which an experimental TIMP-1 level is compared. X1, Y1 and Z1 cut-offs are combined to determine the presence or severity of fibrosis in a sample. Similarly, X2, Y2 and Z2 cut-off values are combined to determine the presence or severity of fibrosis in a sample. A sample having an α2-MG level less than X1, an HA level less than Y1, or a TIMP-1 level less than Z1 is classified as having F0–F1 fibrosis. A sample having an α2-MG level above X1, an HA level above Y1, and a TIMP-1 level above Z1 is possibly positive for F2–F4 fibrosis and warrants further analysis. Furthermore, a sample having an α2-MG level above X2, an HA level above Y2, and a TIMP-1 level above Z2 is classified as having F2–F4 fibrosis. A sample having an α2-MG level above X1, an HA level above Y1, and a TIMP-1 level above Z1 but one or more levels below X2, Y2 or Z2 is classified as having an "indeterminate status." It is understood that X2 generally is equal to or greater than X1; Y2 generally is equal to or greater than Y1; and Z2 generally is equal to or greater than Z1.

One skilled in the art can select α2-MG, HA and TIMP-1 cut-offs X1, Y1, Z1, X2, Y2 and Z2 to achieve one or more clinically useful parameters, such as a desired sensitivity or specificity, or a desired negative predictive value, positive predictive value or accuracy for a patient population having a particular fibrosis prevalence. Factorial Design Optimization, also known as Design of Experiments, methodology can be used, for example, to select the appropriate cut-off values. As disclosed herein in Example II, optimization software (DOE Keep It Simple Statistically from Air Academy Associates (Colorado Springs, Colo.) was used in a central composite design experiment to simultaneously vary the three cut-offs X1, Y1 and Z1, and then to simultaneously vary the three cut-offs X2, Y2 and Z2. In particular, the α2-MG cut-off was varied from 2.0 to 5.0 mg/ml; the HA cut-off was varied from 25–75 ng/ml; and the TIMP-1 cut-off was varied from 1000–1700 ng/ml. By comparing the test results determined for the 194 patients in the database (see Table 4) with the assigned X1, Y1 and Z1 cut-offs, each of the 194 samples were determined to be a true positive, true negative, false positive or false negative, and the clinical parameters of sensitivity, specificity, negative predictive value, positive predictive value and accuracy were determined for the study patient population. Although determination of the α2-MG, HA and TIMP-1 cut-off values is illustrated herein using the DOE KISS program, one skilled in the art understands that other computer programs for identifying cooperative interactions among multiple variables and for performing simultaneous equation calculations also can be used. For example, ECHIP optimization software, available from ECHIP, Incorporated (Hockessin, Del.), or Statgraphics optimization software, available from STSC, Incorporated (Rockville, Md.), also can be useful in determining α2-MG, HA and TIMP-1 cut-off values useful in the methods of the invention.

The clinical parameters of sensitivity, specificity, negative predictive value, positive predictive value and accuracy are calculated using true positives, false positives, true negatives and false negatives. A "true positive" sample is a sample positive for the indicated stage of fibrosis according to clinical biopsy, which is also diagnosed positive according to a method of the invention. A "false positive" sample is a sample negative for the indicated stage of fibrosis by biopsy, which is diagnosed positive according to a method of the invention. Similarly, a "false negative" is a sample positive for the indicated stage of fibrosis by biopsy, which is diagnosed negative according to a method of the invention. A "true negative" is a sample negative for the indicated stage of fibrosis by biopsy, and also negative for fibrosis according to a method of the invention. See, for example, Motulsky (Ed.), *Intuitive Biostatistics* New York: Oxford University Press (1995).

As used herein, the term "sensitivity" means the probability that a diagnostic method of the invention gives a positive result when the sample is positive, for example, fibrotic with a Metavir score of F2–F4. Sensitivity is calculated as the number of true positive results divided by the sum of the true positives and false negatives. Sensitivity essentially is a measure of how well a method correctly identifies those with fibrotic disease. In a method of the invention, the X1, Y1, Z1, X2, Y2 and Z2 values can be selected such that the sensitivity of diagnosing an individual is at least about 70%, and can be, for example, at least 75%, 80%, 85%, 90% or 95% in at least 60% of the patient population assayed, or in at least 65%, 70%, 75% or 80% of the patient population assayed.

As used herein, the term "specificity" means the probability that a diagnostic method of the invention gives a negative result when the sample is not positive, for example, not of Metavir fibrosis stage F2–F4. Specificity is calculated as the number of true negative results divided by the sum of the true negatives and false positives. Specificity essentially is a measure of how well a method excludes those who do not have fibrosis. In a method of the invention, the cut-off values X1, Y1, Z1, X2, Y2 and Z2 can be selected such that, when the sensitivity is at least about 70%, the specificity of diagnosing an individual is in the range of 70–100%, for example, at least 75%, 80%, 85%, 90% or 95% in at least 60% of the patient population assayed, or in at least 65%, 70%, 75% or 80% of the patient population assayed. As illustrated in Example II, a specificity of greater than 98% and a sensitivity of about 77% were achieved in the non-indeterminate patient population, which was about 70% of the patient population having a fibrosis prevalence of 30%.

The term "negative predictive value," as used herein, is synonymous with "NPV" and means the probability that an individual diagnosed as not having fibrosis actually does not have the disease. Negative predictive value can be calculated as the number of true negatives divided by the sum of the true negatives and false negatives. Negative predictive value is determined by the characteristics of the diagnostic method as well as the prevalence of fibrosis in the population analyzed. In a method of the invention, the α2-MG, HA and TIMP-1 cut-off values can be selected such that the negative predictive value in a population having a liver fibrosis prevalence of up to 10% is in the range of 75–99% and can be, for example, at least 80%, at least 85%, at least 90%, or at least 95%, in at least 60% of the patient population assayed, for example, in at least 65%, 70%, 75% or 80% of the patient population assayed. The α2-MG, HA and TIMP-1 cut-off values also can be selected such that the negative predictive value in a population having a liver fibrosis prevalence of up to 20% is in the range of 75–99% and can be, for example, at least 80%, at least 85%, at least 90%, or at least 95%, in at least 60% of the patient population assayed, for example, in at least 65%, 70%, 75% or 80% of the patient population assayed. In addition, α2-MG, HA and TIMP-1 cut-off values can be selected such that the negative predictive value in a population having a liver fibrosis prevalence of up to 30% is in the range of 75–99% and can be, for example, at least 80%, at least 85%, at least 90%, or at least 95%, in at least 60% of the patient population assayed, for example, in at least 65%, 70%, 75% or 80% of the patient population assayed.

The term "positive predictive value," as used herein, is synonymous with "PPV" and means the probability that an individual diagnosed as having fibrosis actually has the condition. Positive predictive value can be calculated as the number of true positives divided by the sum of the true positives and false positives. Positive predictive value is determined by the characteristics of the diagnostic method as well as the prevalence of fibrosis in the population analyzed. In a method of the invention, the α2-MG, HA and TIMP-1 cut-off values can be selected such that, in a patient population having up to 10% liver fibrosis prevalence, the positive predictive value of the method is at least about 75%, and can be at least 80%, at least 85%, at least 90% or at least 95% in at least 60% of the patient population assayed, for example, in at least 65%, 70%, 75% or 80% of the patient population assayed. The α2-MG, HA and TIMP-1 cut-off values also can be selected such that, in a patient population having up to 20% liver fibrosis prevalence, the positive predictive value of the method is at least about 75%, and can be at least 80%, at least 85%, at least 90% or at least 95% in at least 60% of the patient population assayed, for example, in at least 65%, 70%, 75% or 80% of the patient population assayed. Similarly, the α2-MG, HA and TIMP-1 cut-off values can be selected such that, in a patient population having up to 30% liver fibrosis prevalence, the positive predictive value of the method is at least about 75%, and can be at least 80%, at least 85%, at least 90% or at least 95% in at least 60% of the patient population assayed, for example, in at least 65%, 70%, 75% or 80% of the patient population assayed.

Predictive values, including negative and positive predictive values, are influenced by the prevalence of the disease in the population analyzed. In the methods of the invention, the cut-off values X1, Y1, Z1, X2, Y2 and Z2 can be selected to produce a desired clinical parameter for a clinical population with a particular liver fibrosis prevalence. For example, cut-off values can be selected for a liver fibrosis prevalence of up to 10%, 12%, 15%, 18%, 20%, 25% or 30% which can be seen, for example, in a hepatologist's office. Cut-off values also can be selected for a liver fibrosis prevalence of up to 1%, 2%, 3%, 4%, 5%, 6%, 7% or 8%, which can be representative of the fibrosis prevalence seen in a general practitioner's office.

As used herein, the term "accuracy" means the overall agreement between the diagnostic method and the disease state. Accuracy is calculated as the sum of the true positives and true negatives divided by the total number of sample results and is affected by the prevalence of fibrosis in the population analyzed. The α2-MG, HA and TIMP-1 cut-off values can be selected such that the accuracy of a method of the invention in a patient population having a liver fibrosis prevalence of up to 10% is at least about 80% and can be, for example, at least 85%, 90%, 91%, 92%, 93%, 94%, 95%, 96%, 97%, 98%, or 99% in at least 60% of the patient population assayed, for example, in at least 65%, 70%, 75% or 80% of the patient population assayed. The α2-MG, HA and TIMP-1 cut-off values also can be selected such that the accuracy of a method of the invention in a patient population having a liver fibrosis prevalence of up to 20% is at least about 80% and can be, for example, at least 85%, 90%, 91%, 92%, 93%, 94%, 95%, 96%, 97%, 98%, or 99% in at least 60% of the patient population assayed, for example, in at least 65%, 70%, 75% or 80% of the patient population assayed. Similarly, the α2-MG, HA and TIMP-1 cut-off values can be selected such that the accuracy of a method of the invention in a patient population having a liver fibrosis prevalence of up to 30% is at least about 80% and can be, for example, at least 85%, 90%, 91%, 92%, 93%, 94%, 95%, 96%, 97%, 98%, or 99% in at least 60% of the patient population assayed, for example, in at least 65%, 70%, 75% or 80% of the patient population assayed.

Methods Not Limited to Specific Markers

The present invention also provides a method of diagnosing the presence or severity of liver fibrosis in an individual by comparing a level of a first fibrotic marker X in the individual to a cut-off value X1 to determine whether the individual is positive for the first fibrotic marker X; comparing a level of a second fibrotic marker Y in the individual to a cut-off value Y1 to determine whether the individual is positive for the second fibrotic marker Y; and diagnosing the presence or severity of liver fibrosis in the individual based on positivity or negativity for X and Y, where, in a population with up to 40% fibrosis prevalence, at least 65% of individuals in the population are diagnosed with an accuracy of at least 90%.

A method of the invention can include, if desired, comparing a level of a third fibrotic marker Z in the individual to a cut-off value Z1 to determine whether the individual is positive for the third fibrotic marker Z and diagnosing the presence or severity of liver fibrosis in the individual based on positivity or negativity for X, Y and Z. In one embodiment, the first fibrotic marker is α2-MG, the second fibrotic marker is HA, and the third fibrotic marker is TIMP-1.

In another embodiment, the levels of at least three fibrotic markers are compared, and, in a further embodiment, the levels of exactly three fibrotic markers are compared to their respective cut-off values. In additional embodiments, the levels of at least four or at least five fibrotic markers are compared. A method of the invention can be useful, for example, to differentiate no or mild liver fibrosis from moderate to severe liver fibrosis.

In a specific embodiment, a method of the invention serves to diagnose at least 65% of individuals in a population with up to 30% fibrosis prevalence with an accuracy of at least 93%. In a further embodiment, a method of the invention serves to diagnose at least 70% of individuals in a population with up to 20% fibrosis prevalence with an accuracy of at least 94%. In yet a further embodiment, a method of the invention serves to diagnose at least 70% of individuals in a population with up to 10% fibrosis prevalence with an accuracy of at least 96%.

The methods of the invention provide unparalleled performance in diagnosing the presence or severity of liver fibrosis. While not all patients are provided with a diagnosis, the majority are diagnosed with extremely good accuracy.

As an example, in a patient population with about 40% fibrosis prevalence, almost 70% of the population are diagnosed with more than 91% accuracy and with a positive predictive value of more than 96% and a negative predictive value of more than 89%. This excellent performance contrasts with alternative methods such as the method of Imbert-Bismut et al., Lancet 357:1069 (2001). Using the method of Imbert-Bismut et al. based on analysis of the six markers α2-MG, α2-globulin, total bilirubin, γ-globulin, apoA1 and GGT, only about 50% of a population having about 40% fibrosis prevalence are diagnosed, and only with an accuracy of about 89% (see Table 8). Thus, the methods of the invention provide an improvement, in that a significantly greater percentage of a patient population (about 70% as compared to about 50%) are diagnosed, and with an accuracy of more than 91% as compared to an accuracy of around 89% (see Table 8). Due to the novel performance characteristics of a method of the invention, biopsy is typically unnecessary in at least 65% of a patient population, and the patients diagnosed can have confidence in a diagnosis that is more than 90% accurate.

Like other methods of the invention, a method of the invention based on comparison of at least two fibrotic markers can be used to diagnose the presence or severity of liver fibrosis in an individual having or suspected of having any liver disorder, including viral hepatitis, autoimmune liver disease such as autoimmune hepatitis, alcoholic liver disease, fatty liver disease or drug-induced liver disease, or any of the other liver diseases described herein above. Similarly a method of the invention based on comparison of at least two fibrotic markers can be used to diagnose the presence or severity of fibrotic disorders including pulmonary fibrosis, kidney fibrosis, prostate fibrosis, breast fibrosis or a rheumatoid disease, or another fibrotic disorder described herein or known in the art.

A method of the invention relies on comparison of the level of a fibrotic marker to a predetermined cut-off value. For markers that positively correlate with fibrosis, positivity is indicated by a level that is greater than the predetermined cut-off value. For markers that negatively correlate with fibrosis, positivity is indicated by a level that is less than the predetermined cut-off value. Cut-off values useful in the methods of the invention can be determined as described herein, for example, using design of experiments (DOE) analysis.

As for the other diagnostic methods of the invention, these methods can be practiced using a variety of fibrotic markers known in the art or described herein. Such fibrotic markers include, without limitation, α2-MG, HA, TIMP-1, PIIINP, laminin, tenascin, collagen type IV, collagen type VI, YKL-40, MMP-3, MMP-2, MMP-9/TIMP-1 complex, sFas ligand, TGF-β1, IL-10, apoA1, apoA2 or ApoB. Additional serological, biochemical, clinical and echographic fibrotic markers are described herein above or are known in the art and can be included in any combination in a method of the invention. Furthermore, it is understood that comparison of the first and second fibrotic markers and any additional fibrotic markers can be performed simultaneously or in any order and using any combination of assay formats.

As described above, the "level" of a fibrotic marker can be a relative or absolute amount of, for example, RNA, protein or activity and can be a direct or indirect measurement of the fibrotic marker. In addition, the value of the level can be obtained from a secondary source, such as a physician or diagnostic laboratory or can be determined using any convenient sample and assay, including but not limited to those described herein above. Methods useful in determining the level of a fibrotic marker in order to perform the comparisons included in the methods of the invention encompass, for example, hybridization methods such as RT-PCR and RNA blot analysis, immunoassays including enzyme-linked immunosorbent assays (ELISAs) and radio-immunoassays (RIAs), sandwich immunoassays, quantitative western blotting and other standard assays for determining protein levels, and, where applicable, assays for the activity of the fibrotic marker. Such assays are routine in the art and described herein above.

The present invention further provides a method of diagnosing the presence or severity of liver fibrosis in an individual by comparing a level of a first fibrotic marker X in the individual to a cut-off value X1 to determine whether the individual is positive for the first fibrotic marker X; comparing a level of a second fibrotic marker Y in the individual to a cut-off value Y1 to determine whether the individual is positive for the second fibrotic marker Y; and diagnosing the presence or severity of liver fibrosis in the individual based on positivity or negativity for X and Y, where the cut-off values X1 and Y1 are optimized individually to give a desired performance characteristic.

If desired, a method of the invention can include the steps of comparing a level of a third fibrotic marker Z in the individual to a cut-off value Z1 to determine whether the individual is positive for the third fibrotic marker Z and diagnosing the presence or severity of liver fibrosis in the individual based on positivity or negativity for X, Y and Z, where the cut-off values X1, Y1 and Z1 are optimized individually to give a desired performance characteristic. In one embodiment, levels of α2-MG, HA and TIMP-1 are compared. In other embodiments, the levels of exactly three, at least three, at least four, or at least five fibrotic markers are compared. A method of the invention can be useful, for example, in differentiating no or mild liver fibrosis from moderate to severe liver fibrosis. Cut-off values can be optimized as described herein, for example, using DOE analysis.

Further provided by the invention is a method of diagnosing the presence or severity of liver fibrosis in an individual by comparing a level of a first fibrotic marker X in the individual to two cut-off values X1 and X2 to determine whether the individual is positive for the first fibrotic marker X; comparing a level of a second fibrotic marker Y in the individual to two cut-off values Y1 and Y2 to determine whether the individual is positive for the second fibrotic marker Y; and diagnosing the presence or severity of liver fibrosis in the individual based on positivity or negativity for X and Y, where the cut-off values X1, Y1, X2 and Y2 are optimized individually to give a desired performance characteristic. Such performance characteristics include particular sensitivities, specificities, PPVs, NPVs and accuracies, as described herein above.

A method of the invention can further include the steps of comparing a level of a third fibrotic marker Z in the individual to two cut-off values Z1 and Z1 to determine whether the individual is positive for the third fibrotic marker Z; and diagnosing the presence or severity of liver fibrosis in the individual based on positivity or negativity for X, Y and Z, where the cut-off values X1, Y1, Z1, X2, Y2 and Z2 are optimized individually to give a desired performance characteristic. In a method of the invention, cut-off values can be conveniently optimized, for example, using DOE analysis.

Methodology

A variety of means can be useful for detecting α2-MG, HA and TIMP-1 and for determining a level of α2-MG, HA and TIMP in a sample. In one embodiment, the invention is practiced by determining the level of α2-MG protein in a sample from the individual to be diagnosed using, for example, one or more α2-MG-specific binding agents such as anti-α2-MG antibodies. In another embodiment, a method of the invention is practiced by assaying for α2-MG activity in a sample from the individual.

A variety of means also can be used in a method of the invention to detect HA or determine a level of HA in a sample. In one embodiment, the invention is practiced by determining the level of HA in a sample using one or more HA-specific binding agents such as HA-binding proteins or anti-HA antibodies.

Similarly, a variety of means can be used in a method of the invention to detect TIMP-1 or determine a level of TIMP-1 in a sample. In one embodiment, the invention is practiced by determining the level of TIMP-1 protein in a sample from the individual to be diagnosed. The level of TIMP-1 protein can be determined, for example, using one or more TIMP-1-specific binding agents such as anti-TIMP-1 antibodies. In another embodiment, the invention is practiced by assaying for TIMP-1 activity in a sample from the individual to be diagnosed.

In a particular embodiment, the invention provides a method of diagnosing the presence or severity of liver fibrosis in an individual by determining the level of α2-MG protein in a sample from the individual; determining the level of HA in a sample from the individual; and determining the level of TIMP-1 protein in a sample from the individual; and diagnosing the presence or severity of liver fibrosis in the individual based on the levels of α2-MG protein, HA and TIMP-1 protein. If desired, the level of α2-MG protein, HA and TIMP-1 protein each can be determined using an enzyme-linked assay.

In a further embodiment, the present invention provides a method of differentiating no or mild liver fibrosis from moderate to severe liver fibrosis in an individual by contacting an appropriate dilution of a sample from the individual with anti-α2-MG antibody under conditions suitable to form a first complex of α2-MG and anti-α2-MG antibody; washing the first complex to remove unbound molecules; determining the amount of α2-MG-containing first complex; contacting an appropriate dilution of a sample from the individual with a HA-binding protein under conditions suitable to form a second complex of HA and HA-binding protein; washing the second complex to remove unbound molecules; determining the amount of HA-containing second complex; contacting an appropriate dilution of a sample from the individual with anti-TIMP-1 antibody under conditions suitable to form a third complex of TIMP-1 and anti-TIMP-1 antibody; washing the third complex to remove unbound molecules; determining the amount of TIMP-1-containing third complex; and differentiating no or mild liver fibrosis from moderate to severe liver fibrosis in the individual based on the amounts of α2-MG, HA and TIMP-1-containing complexes.

It is understood that detecting α2-MG, HA and TIMP-1, or detecting α2-MG, HA and YKL-40, as discussed further below, can be accomplished by assaying for the amount of protein or polysaccharide directly, or, in the case of α2-MG and TIMP-1, can be determined by assaying for RNA levels or enzyme activity of a protease regulated by α2-MG or TIMP-1. Similarly, where one or more additional fibrotic markers is detected in a method of the invention, the marker can be assayed directly, or a precursor such as RNA, or a breakdown or proteolytic product, or an activity correlated with levels of the marker can be assayed. It is understood that determining a level of α2-MG, HA, TIMP-1 and YKL-40, or a level of any additional marker of fibrosis, can be performed using absolute values, for example, for RNA or protein levels or enzyme activity, or can be determined as relative values in comparison to one or more reference values.

It further is understood that each of the three fibrotic marker assays (α2-MG/HA/TIMP-1 or α2-MG/HA/YKL-40), as well as any additional assays, is performed independently of the others, in any order, and that any combination of assay formats is encompassed by the invention. As an example, a level of α2-MG and HA can be determined by assaying for the concentration of α2-MG and HA while a level of TIMP-1 is determined by assaying for TIMP-1 enzyme activity. As another example, a level of α2-MG can be determined using a radioimmunoassay, while levels of HA and TIMP-1 are determined using enzyme-linked assays. One skilled in the art understands that detection of the three fibrotic markers (α2-MG/HA/TIMP-1 or α2-MG/HA/YKL-40) and detection of any additional markers can be performed simultaneously or in any order. Furthermore, a single sample such as a serum sample can be obtained from an individual and subdivided into three portions for detecting α2-MG, HA and TIMP-1 or α2-MG, HA and TIMP-1, or the markers can be detected using different samples, which can be of the same or a different type and can be undiluted or diluted to the same or different extents. Where two or more samples are used, the samples are usually obtained from the individual within a relatively short time frame, for example, several days to several weeks.

RNA Methods

Hybridization methods can be used to detect α2-MG or TIMP-1 mRNA or determine the level of α2-MG or TIMP-1 mRNA or the mRNA of another fibrotic marker useful in the invention such as YKL-40. Numerous methods are well known in the art for determining mRNA levels by specific or selective hybridization with a complementary nucleic acid probe. Such methods include solution hybridization procedures as well as solid-phase hybridization procedures in which the probe or sample is immobilized on a solid support. Specific examples of useful methods include amplification methods such as target and signal amplification methods and include PCR (polymerase chain reaction) and reverse-transcriptase-PCR (RT-PCR); transcription mediated amplification (Gen-Probe Incorporated; San Diego, Calif.); branched chain DNA (bDNA) amplification (Bayer Diagnostics; Emeryville, Calif.); strand displacement amplification (SDA; Becton Dickinson; Franklin Lakes, N.J.); and ligase chain reaction (LCR) amplification (Abbott Laboratories; Abbott Park, Ill.). Additional methods useful in the invention include RNase protection; Northern analysis or other RNA blot, dot blot or membrane-based technology; dip stick; pin; and two-dimensional array immobilized onto a chip. Conditions are well known in the art for quantitative determination of mRNA levels using both solution and solid phase hybridization procedures as described, for example, in Ausubel et al., *Current Protocols in Molecular Biology* (Supplement 47), John Wiley & Sons, New York (1999).

The polymerase chain reaction (PCR) RT-PCR can be useful in the methods of the invention. PCR or RT-PCR can be performed with isolated RNA or crude or partially fractionated samples, for example, cells pelleted from a whole blood sample. PCR methods are well known in the art as described, for example, in Dieffenbach and Dveksler, *PCR Primer: A Laboratory Manual*, Cold Spring Harbor Press, Plainview, N.Y. (1995). Multisample formats such as two-dimensional arrays offer the advantage of analyzing numerous different samples in a single assay. Solid-phase dip stick-based methods also can be useful in the invention and offer the advantage of being able to rapidly analyze a fluid sample and obtain an immediate result.

Probes for detecting α2-MG and TIMP-1 mRNA or for determining α2-MG and TIMP-1 mRNA levels are well known in the art. One skilled in the art can use, for example, a probe corresponding to some or all of the human α2-MG nucleic acid sequence shown in FIG. 1 (SEQ ID NO: 1) or some or all of the human TIMP-1 nucleic acid sequence shown in FIG. 3, respectively. Appropriate conditions for various assay formats for detecting α2-MG and TIMP-1 mRNA or for determining α2-MG and TIMP-1 mRNA levels are well known in the art or can be established using routine methods. As an example, conditions and probes for Northern analysis of α2-MG RNA in human samples are described, for example, in Ortego et al., supra, 1997. As another example, conditions and probes for RNA slot blot hybridization to determine α2-MG RNA expression in human samples are described in Simon et al., supra, 1996. Similarly, Northern analysis of TIMP-1 RNA in human samples can be performed as described, for example, in Yoshiji et al., supra, 1996; RT-PCR assays for TIMP-1 in human samples also are well known in the art as described, for example, in Janowska-Wieczorek et al., supra, 2000, and Groft et al., supra, 2001. The skilled person understands that these and other assays can be useful for detecting α2-MG, TIMP-1 or YKL-40 RNA or for determining α2-MG, TIMP-1 or YKL-40 RNA levels or the levels of other fibrotic markers useful in the methods of the invention.

Immunoassays

A variety of immunoassay formats, including competitive and non-competitive immunoassay formats, antigen capture assays and two-antibody sandwich assays also are useful the methods of the invention (Self and Cook, *Curr. Opin. Biotechnol.* 7:60–65 (1996)). In one embodiment, a method of the invention relies on one or more antigen capture assays. In an antigen capture assay, antibody is bound to a solid phase, and sample is added such that α2-MG, HA, TIMP-1, YKL-40 or another fibrotic marker antigen is bound by the antibody. After unbound proteins are removed by washing, the amount of bound antigen can be quantitated, if desired, using, for example, a radioassay (Harlow and Lane, *Antibodies A Laboratory Manual* Cold Spring Harbor Laboratory: New York, 1988)). One skilled in the art understands that immunoassays useful in the invention are performed under conditions of antibody excess, or as antigen competitions, to quantitate the amount of antigen and, thus, determine a level of α2-MG, HA, TIMP-1 or YKL-40.

Enzyme-linked immunosorbent assays (ELISAs) can be useful in the methods of the invention. An enzyme such as horseradish peroxidase (HRP), alkaline phosphatase (AP), β-galactosidase or urease can be linked, for example, to an anti-α2-MG, anti-HA, anti-TIMP-1 or anti-YKL-40 antibody or to a secondary antibody for use in a method of the invention. A horseradish-peroxidase detection system can be used, for example, with the chromogenic substrate tetramethylbenzidine (TMB), which yields a soluble product in the presence of hydrogen peroxide that is detectable at 450 nm. Other convenient enzyme-linked systems include, for example, the alkaline phosphatase detection system, which can be used with the chromogenic substrate p-nitrophenyl phosphate to yield a soluble product readily detectable at 405 nm. Similarly, a β-galactosidase detection system can be used with the chromogenic substrate o-nitrophenyl-β-D-galactopyranoside (ONPG) to yield a soluble product detectable at 410 nm, or a urease detection system can be used with a substrate such as urea-bromocresol purple (Sigma Immunochemicals, St. Louis, Mo.). Useful enzyme-linked primary and secondary antibodies can be obtained from a number of commercial sources such as Jackson Immuno-Research (West Grove, Pa.) as described further below.

Chemiluminescent detection also can be useful for detecting α2-MG, HA, TIMP-1 or YKL-40 or for determining a level of α2-MG, HA, TIMP-1 or YKL-40 or another fibrotic marker according to a method of the invention. Chemiluminescent secondary antibodies can be obtained commercially from various sources such as Amersham.

Fluorescent detection also can be useful for detecting α2-MG, HA, TIMP-1 or YKL-40 or for determining a level of α2-MG, HA, TIMP-1 or YKL-40 or another fibrotic marker in a method of the invention. Useful fluorochromes include, without limitation, DAPI, fluorescein, Hoechst 33258, R-phycocyanin, B-phycoerythrin, R-phycoerythrin, rhodamine, Texas red and lissamine. Fluorescein or rhodamine labeled α2-MG-, HA-, TIMP-1- or YKL-40-specific binding agents such as anti-α2-MG, anti-HA, anti-TIMP-1, or anti-YKL-40 antibodies, or fluorescein- or rhodamine-labeled secondary antibodies can be useful in the invention. Useful fluorescent antibodies can be obtained commercially, for example, from Tago Immunologicals (Burlingame, Calif.) as described further below.

Radioimmunoassays (RIAs) also can be useful in the methods of the invention. Such assays are well known in the art. For example, Brophy et al., *Biochem. Biophys. Res. Comm.* 167:898–903 (1990)), describes a radioimmunoassay for detection of TIMP-1, and Pharmacia makes a radiometric assay for quantitation of HA using an $^{125}$I-labelled HA-binding protein (Guechot et al., *Clin. Chem.* 42:558–563 (1996). Radioimmunoassays can be performed, for example, with $^{125}$I-labeled primary or secondary antibody (Harlow and Lane, supra, 1988).

A signal from a detectable reagent can be analyzed, for example, using a spectrophotometer to detect color from a chromogenic substrate; a radiation counter to detect radiation, such as a gamma counter for detection of $^{125}$I; or a fluorometer to detect fluorescence in the presence of light of a certain wavelength. Where an enzyme-linked assay is used, quantitative analysis of the amount of α2-MG, HA, TIMP-1 or YKL-40 or another fibrotic marker can be performed using a spectrophotometer such as an EMAX Microplate Reader (Molecular Devices; Menlo Park, Calif.) in accordance with the manufacturer's instructions. It is understood that the assays of the invention can be automated or performed robotically, if desired, and that the signal from multiple samples can be detected simultaneously.

The methods of the invention also encompass the use of capillary electrophoresis based immunoassays (CEIA), which can be automated, if desired. Immunoassays also can be used in conjunction with laser-induced fluorescence as described, for example, in Schmalzing and Nashabeh, *Electrophoresis* 18:2184–93 (1997), and Bao, *J. Chromatogr. B. Biomed. Sci.* 699:463–80 (1997). Liposome immunoassays, such as flow-injection liposome immunoassays and liposome immunosensors, also can be used to detect α2-MG, HA, TIMP-1 or YKL-40 or to determine a level of α2-MG, HA, TIMP-1 or YKL-40 or another fibrotic marker according to a method of the invention (Rongen et al., *J. Immunol. Methods* 204:105–133 (1997)).

Sandwich enzyme immunoassays also can be useful in the methods of the invention. In a two-antibody sandwich assay, a first antibody is bound to a solid support, and the antigen is allowed to bind to the first antibody. The amount of α2-MG, HA, TIMP-1, YKL-40 or another fibrotic marker antigen is quantitated by measuring the amount of a second antibody that binds the fibrotic marker.

As an example, a two-antibody sandwich immunoassay can be useful to determine a level of TIMP-1 as described in Murawaki et al., supra, 1993. Briefly, serum (25 µl) is diluted 41-fold with 10 mM sodium phosphate buffer, pH 7.0 (1.0 ml). The diluted sample (20 µl) is mixed with 0.3 ml of 10 mM sodium phosphate buffer, pH 7.0, containing 50 ng/ml monoclonal antibody (Fab of clone 7-6C1) labeled with horseradish peroxidase, 1% bovine serum albumin, 0.1% Tween 20, 0.1 M NaCl and 0.005% thimerosal. A 0.1 ml aliquot of the mixed solution is transferred to each microplate well previously coated with a second monoclonal antibody (clone 7-23G9) having a different epitope specificity, and the plate incubated for 30 minutes at room temperature without shaking. The plate is washed three times with 0.3 ml 10 mM sodium phosphate buffer, pH 7.0, containing 0.1% Tween 20 and 0.1 M NaCl. Peroxidase activity bound to the plate is assayed by a 15 minute incubation at room temperature with 0.1 ml 0.15 M citric acid sodium phosphate buffer, pH 4.9, containing 0.5 mg/ml o-phenylenediamine and 0.02% $H_2O_2$. After stopping the reaction by addition of 0.1 ml 2 N $H_2SO_4$, the absorbance at 492 nm is measured in a microplate reader using a standard of human serum TIMP-1. Linearity between the amount of TIMP-1 and absorbance at 492 nm is demonstrated by graphing with logarithmic scales and yields an assay range of about 1.5 to 300 µg/well.

Quantitative western blotting also can be used to detect α2-MG, HA, TIMP-1 or YKL-40 or to determine a level of α2-MG, HA, TIMP-1 or YKL-40 or a level of another fibrotic marker antigen in a method of the invention. Western blots can be quantitated by well known methods such as scanning densitometry. As an example, protein samples are electrophoresed on 10% SDS-PAGE Laemmli gels. Primary murine monoclonal antibodies, for example, against human α2-MG, HA, TIMP-1 or YKL-40 are reacted with the blot, and antibody binding confirmed to be linear using a preliminary slot blot experiment. Goat anti-mouse horseradish peroxidase-coupled antibodies (BioRad) are used as the secondary antibody, and signal detection performed using chemiluminescence, for example, with the Renaissance chemiluminescence kit (New England Nuclear; Boston, Mass.) according to the manufacturer's instructions. Autoradiographs of the blots are analyzed using a scanning densitometer (Molecular Dynamics; Sunnyvale, Calif.) and normalized to a positive control. Values are reported, for example, as a ratio between the actual value to the positive control (densitometric index). Such methods are well known in the art as described, for example, in Parra et al., *J. Vasc. Surg.* 28:669–675 (1998).

Sources for Antibodies

As described herein above, immunoassays including but not limited to enzyme-linked immunosorbent assays, radioimmunoassays and quantitative western analysis, can be useful in the diagnostic methods of the invention. Such assays rely on one or more antibodies, for example, anti-α2-MG, anti-HA, anti-TIMP-1 or anti-YKL-40 antibodies. As used herein, the term "antibody" is used in its broadest sense to include polyclonal and monoclonal antibodies, as well as polypeptide fragments of antibodies that retain binding activity for α2-MG, HA, TIMP-1, YKL-40 or the relevant fibrotic marker antigen of at least about $1\times10^5$ M$^{-1}$. One skilled in the art understands that antibody fragments such as anti-α2-MG, anti-HA, anti-TIMP-1 and anti-YKL-40 antibody fragments and including Fab, F(ab')$_2$ and Fv fragments can retain binding activity for the relevant fibrotic marker antigen and, thus, are included within the definition of the term antibody as used herein. Methods of preparing monoclonal and polyclonal antibodies are routine in the art, as described, for example, in Harlow and Lane, supra, 1988.

The term antibody, as used herein, also encompasses non-naturally occurring antibodies and fragments containing, at a minimum, one $V_H$ and one $V_L$ domain, such as chimeric antibodies, humanized antibodies and single chain Fv fragments (scFv) that specifically bind α2-MG, HA, TIMP-1, YKL-40 or the relevant fibrotic marker antigen. Such non-naturally occurring antibodies can be constructed using solid phase peptide synthesis, produced recombinantly or obtained, for example, by screening combinatorial libraries consisting of variable heavy chains and variable light chains as described by Borrebaeck (Ed.), *Antibody Engineering* (Second edition) New York: Oxford University Press (1995).

A variety of useful anti-α2-MG, anti-HA, anti-TIMP-1 and anti-YKL-40 monoclonal and polyclonal antibodies are well known in the art and, in many cases, are commercially available. For example, a nephelometry assay for α2-macroglobulin is available from Beckman Coulter (kit #449430), and affinity purified goat anti-human α2-MG and peroxidase-labeled goat anti-human α2-MG antibodies suitable for ELISA and western blotting are available, for example, from Cedarlane Laboratories Limited (CL20010AP and CL20010APHP) and Affinity Biologicals Incorporated (GAA2M-AP and GAA2M-APHRP). Similarly, affinity purified sheep anti-HA antiserum can be obtained from Biotrend (#5029-9990).

Anti-human TIMP-1 antibodies also are readily available from a variety of commercial sources. For example, the anti-human TIMP-1 monoclonal antibody 147-6D11 is suitable for ELISA or western blotting analysis and can be obtained from Medicorp, Inc. (Montreal, Canada), and the anti-human TIMP-1 monoclonal antibody MAB970 is available from R&D Systems, Inc., for use, for example, in western blotting or sandwich ELISA assays. MAB970 can be combined, for example, with biotinylated anti-human TIMP-1 antibody (BAF970) from R&D Systems, Inc., for detection of TIMP-1 by sandwich ELISA. In addition, rabbit anti-human TIMP-1 polyclonal antiserum and mouse anti-human monoclonal antibodies suitable, for example, for western blotting with enhanced chemiluminescence detection can be obtained from Research Diagnostics Inc. (RDI-TIMP1abr and RDI-TIMP1-C1).

Assays for Activity

As discussed above, assays based on the activity of a fibrotic marker also can be useful for detecting α2-MG, HA or TIMP-1 or for determining a level of α2-MG, HA or TIMP-1 or another fibrotic marker and, therefore, are useful in the methods of the invention. As an example, a variety of assays for α2-MG activity can be useful for detecting α2-MG or determining a level of α2-MG in a sample in a method of the invention. Because α2-MG-bound proteases display inhibited proteolytic activity but retain the ability to hydrolyze amide and ester bonds of small substrates, α2-MG can be detected, or a level determined, by assaying for inhibition of trypsin, subtilisin, chymotrypsin, plasmin, elastase, thermolysin, or papain activity or the activity of another target protease without inhibition of amidolytic activity. Substrates such as labeled casein or labeled fibrin can be useful for assaying for inhibition of target protease activity. Furthermore, based on its broad protease substrate specificity, a level of α2-MG can be determined by assaying for inhibition of the activity of two or more target proteases using, for example, $^{14}$C-casein and $^{125}$I-fibrin (Armstrong et al., supra, 1999). α2-MG also can be detected or a level of α2-MG determined based on the ability of α2-MG to shield a bound protease from an antibody or a high molecular weight inhibitor. Following reaction of a sample with, for example, trypsin and then trypsin inhibitor, residual trypsin activity is assayed with a low molecular mass substrate such as the amide BApNA (Ganrot, supra, 1966; Armstrong et al., supra, 1985). Trypsin activity following treatment with trypsin inhibitor is indicative of α2-MG. These and other well known assays for α2-MG activity can be useful in the methods of the invention.

Similarly, assays for TIMP-1 activity are well known in the art. In particular, one assays for the ability to inhibit protease activity of a matrix metalloproteinase, for example, using reverse gelatin zymography. Reverse gelatin zymography is performed by including a gelatinase such as gelatinase A in a gel mix with the gelatin substrate. Conditioned media, such as conditioned media from baby hamster kidney cells can be used as a convenient source of gelatinase. Plasma samples are electrophoresed, and the resulting pattern analyzed, for example, with scanning digitization using a Hewlett Packard scanner. TIMP-1 activity is observed as a reduction of gelatin degradation. See, for example, Kossakowska et al., supra, 1998. The skilled person recognizes that these and other routine assays for TIMP-1 activity can be useful in the methods of the invention.

Additional Markers

It is clear that the methods of the invention can be practiced, if desired, by detecting the three markers α2-MG, HA and TIMP-1 without assaying for any additional markers or evaluating any other clinical or echographic characteristics. In addition, these three assays can be used as a panel in combination with one or more additional fibrotic marker assays or evaluation of one or more clinical or echographic variables. In specific embodiments, the invention provides a method of diagnosing the presence or severity of liver fibrosis in an individual by detecting α2-MG, HA and TIMP-1 in a sample and also detecting at least one of the following markers: PIIINP, laminin, tenascin, collagen type IV, collagen type VI, YKL-40, MMP-3, MMP-2, MMP-9/TIMP-1 complex, sFas ligand, TGF-β1, IL-10, apoA1, apoA2 or ApoB. In one embodiment, a method of the invention for diagnosing the presence or severity of liver fibrosis includes the steps of detecting α2-MG, HA, TIMP-1 and YKL-40 in a sample. In a further embodiment, a method of the invention is limited to detecting α2-MG, HA, TIMP-1 and YKL-40, and no additional fibrotic markers are detected.

In view of the above, it is clear that assays for one or more additional biochemical or serological markers of fibrosis or evaluation of one or more clinical or echographic variables associated with fibrosis can be combined with detection of α2-MG, HA, and TIMP-1 to diagnose the presence or severity of liver fibrosis. Examples of additional biochemical and serological markers include, yet are not limited to, PIIINP, laminin, tenascin, collagen type IV, collagen type VI, YKL-40, MMP-3, MMP-2, MMP-9/TIMP-1 complex, sFas ligand, TGF-β1, IL-10, apoA1, apoA2 and apoB. Additional biochemical and serological markers useful in the invention include, without limitation, fibronectin, pseudocholinesterase, manganese superoxide dismutase, N-acetyl-β-glucosaminidase (β-NAG), glutathione peroxidase, connective tissue growth factor (CTGF); platelet derived growth factor (PDGF), PDGF receptor, inducible nitric oxide synthetase, nitrotyrosine, bilirubin, ferritin and α-fetoprotein, γ-glutamyl transpeptidase (GGT), aspartate aminotransferase (AST), alanine aminotransferase (ALT), AST/ALT ratio, albumin, γ-globulins, βγ-block, prothrombin index, Child-Pugh score, PGA index (prothrombin time, GGT concentration and apoA1 concentration), PGAA index (PGA score with α2-macroglobulin level), hemoglobin, mean corpuscular volume, lymphocyte count, cholesterol, urea, creatinine, sodium and platelet count.

A clinical or echographic variable also can be a fibrotic "marker" useful in the methods of the invention. Thus, analysis of one or more clinical or echographic variables can be combined with detection of α2-MG, HA and TIMP-1 to diagnose the presence or severity of liver fibrosis, or another fibrotic disorder as described hereinabove. As examples, such a clinical variable can be patient age or gender or the presence of palmar erythema, Dupuytren's contracture, finger clubbing, spider nevi, firm liver, splenomegaly or collateral circulation. Echographic variables useful in a method of the invention include, for example, liver length (right kidney), irregular liver surface, liver heterogeneity, spleen length, ascites or collateral circulation. See, for example, Oberti et al., *Gastroenterol.* 113:1609–1616 (1997). It is understood that the analysis of these and other well known clinical or echographic variables can be useful in a method of the invention. Furthermore, a method of the invention encompasses determination of the clinical or echographic variable, for example, liver palpation, or can rely on one or more historic, or previously determined clinical or echographic variables.

Assays for detection of biochemical or serological markers useful in the invention are well known in the art and in many cases commercially available. Such assays include, but are not limited to, amplification based methods such as RT-PCR and other methods for quantitative analysis of RNA levels; immunoassays such as radioimmunoassays, enzyme-linked assays, two-antibody sandwich assays and quantitative western analysis; and assays for biological activity such as enzyme activity. Assays for PIIINP, laminin, tenascin, collagen type IV, collagen type VI, YKL-40, MMP-3, MMP-2, MMP-9/TIMP-1 complex, sFas ligand, TGF-β1, IL-10, apoA1, apoA2 and apoB are commercially available from various sources as summarized in Table 1.

TABLE 1

COMMERCIAL SOURCES FOR FIBROTIC MARKER ASSAYS

| Marker | Company | Assay | Catalog number |
|---|---|---|---|
| PIIINP | Orion Diagnostica (Espoo, Finland) | RIA | 05903 |
| laminin | Chemicon Intl. (Temecula, CA) | ELISA | ECM310 |
| tenascin | Chemicon Intl. (Temecula, CA) | ELISA | ECM320 |
| collagen IV | Iatron Laboratories (Tokyo, Japan) | RIA | KCAD1 |
| YKL-40 | Metra Biosystems (Mountain View, CA) | ELISA | 8020 |
| MMP-3 | Amersham Pharmacia (Piscataway, NJ) | ELISA | RPN 2613 |
| MMP-2 | Amersham Pharmacia (Piscataway, NJ) | ELISA | RPN 2617 |

TABLE 1-continued

COMMERCIAL SOURCES FOR FIBROTIC MARKER ASSAYS

| Marker | Company | Assay | Catalog number |
|---|---|---|---|
| MMP-9/TIMP-1 complex | SBA Sciences (Turku, Finland) | ELISA | MP2215 |
| sFas ligand | Bender MedSystems Diagnostics (Vienna, Austria) | ELISA | BMS260/2 |
| TGF-β1 | R&D Systems (Minneapolis, MN) | ELISA | DB100 |
| IL-10 | R&D Systems (Minneapolis, MN) | ELISA | HS100B |
| apoA1 | AlerChek, Inc. (Portland, ME) | ELISA | A70101 |
| apoA2 | AlerChek, Inc. (Portland, ME) | ELISA | A70102 |
| apoB | Sigma Diagnostics (St. Louis, MO) | IT* | 357-A |

*designates immunoturbidimetric

Assays for additional biochemical or serological markers that can be combined with detection of α2-MG, HA and TIMP-1 in a method of the invention also are well known in the art. Fibronectin, for example, can be conveniently assayed by turbidimetric assay available from Roche Diagnostics (Mannheim, Germany). Pseudocholinesterase (PCHE) can be assayed using standard methodology available from Boehringer. Levels of N-acetyl-β-glucosaminidase (β-NAG) can be determined by assaying for enzymatic activity using a kit available from Cortecs diagnostics. Manganese superoxide dismutase (Mn-SOD) levels can be conveniently determined by ELISA using a kit available, for example, from Bender MedSystem. Glutathione peroxidase levels can be determined by assaying for enzymatic activity using, for example, a kit available from Randox Laboratories Ltd. (Oceanside, Calif.).

Total or direct bilirubin, GGT, AST and ALT levels can be determined using an autoanalyser such as Hitachi 917 Automate (Mannheim, Germany) with Roche Diagnostics reagents. Albumin levels can be determined, for example, by the bromocresol green method as described in Doumas et al., *Clin. Chim Acta* 31:87–96 (1971), and ferritin and α-fetoprotein levels can be conveniently determined using, for example, an immunoassay available from Boehringer. In addition, levels of $\alpha_1$ globulin, $\alpha_2$ globulin, β globulin and γ-globulin can be determined, for example, by serum protein electrophoresis in an automatic system (Hydrasys and Hyrys, Sebia; Issy-Les-Moulineaux, France). Methods of determining prothrombin activity also are well known in the art and include the clotting method available from Organon Technika (West Orange, N.J.). PGA index can be determined as described in Poynard et al., *Gastroenterol.* 100:1397–1402 (1991), and PGAA index also can be determined by well known methods as described in Naveau et al., *Dig. Dis. Sci.* 39:2426–2432 (1994)).

Platelet counts, lymphocyte counts, mean corpuscular volume and related variables can be determined by a variety of methodologies using, for example, a Bayer-Technicon H2 analyser (Bayer-Technicon Instruments; Tarrytown, N.Y.). Cholesterol levels can be determined by standard methodologies available, for example, from Boehringer. Thus, it is clear to the skilled person that a variety of methodologies, including but not limited to the above, are well known in the art and can be useful in the diagnostic methods of the invention.

α2-MG/HA/YKL-40 Panel

The present invention also provides a method of diagnosing the presence or severity of liver fibrosis in an individual by detecting α2-MG in a sample; detecting HA in a sample; detecting YKL-40 in a sample; and diagnosing the presence or severity of liver fibrosis in the individual based on the presence or level of α2-MG, HA and YKL-40. A method of the invention can be useful, for example, or differentiating no or mild (F0–F1) liver fibrosis from moderate to severe (F2–F4) liver fibrosis.

In one embodiment, the invention provides a method of diagnosing the presence or severity of liver fibrosis in an individual by determining the level of α2-MG protein in a sample from the individual; determining the level of HA in a sample from the individual; determining the level of YKL-40 protein in a sample from the individual; and diagnosing the presence or severity of liver fibrosis in the individual based on the levels of α2-MG protein, HA and YKL-40 protein. If desired, the levels of α2-MG protein, HA and YKL-40 protein each can be determined using an enzyme-linked assay.

Thus, in particular embodiments, the present invention provides diagnostic methods which rely, in part, on determining a level of the fibrotic marker YKL-40 in a sample. YKL-40, also known as human cartilage glycoprotein 39 (HC gp-39), is named for a molecular weight of 40 kDa and the amino-terminal sequence of the protein, tyrosine-lysine-leucine (YKL). This glycoprotein, a mammalian member of the chitinase family (18-glycosylhydrolases), is a lectin that binds heparin and chitin and is produced by chondrocytes, synovial cells, activated macrophages, neutrophils and MG-63 osteosarcoma cells (Hakala et al., *J. Biol. Chem.* 268:25803–15810 (1993); Nyirkos and Golds, *Biochem. J.* 268:265–268 (1990); Renkema et al., *Eur. J. Biochem.* 251:504–509 (1998); Volck et al., *Proc. Assoc. Am. Physicians* 110:351–360 (1998); and Johansen et al., *J. Bone Miner. Res.* 7:501–511 (1992)). The pattern of YKL-40 expression in normal and diseased tissue indicates that this glycoprotein can function in extracellular matrix remodelling or tissue inflammation (Nyirkos and Golds, supra, 1990; Renkema et al., supra, 1998; and Verheijden et al., *Arthritis Rheum.* 40:1115–1125 (1997)). Furthermore, YKL-40 mRNA is expressed in liver, and initial studies have shown that YKL-40 expression is elevated in patients with chronic liver disease and that increased serum YKL-40 can be associated with fibrosis and fibrogenesis (Johansen et al., *Scand. J. Gastroenterol.* 32:582–590 (1997); and Johansen, *J. Hepatol.* 32:911–920 (2000)).

Methods of determining a level of YKL-40 in samples such as serum and synovial fluid are well known in the art. For example, a radioimmunoassay for YKL-40 based on a rabbit antibody raised against YKL-40 is described in Johansen et al., *Br. J. Rheumatology* 32:949–955 (1993). In addition, a sandwich enzyme immunoassay in a microliter stripwell format is commercially available from Metra Biosystems. In the Metra Biosystems assay, the Fab fragment of a biotin-conjugated monoclonal anti-YKL-40 antibody binds to streptavidin on the strip and captures YKL-40 in a sample. Alkaline phosphatase-conjugated polyclonal anti-YKL-40 antiserum binds the captured YKL-40 antigen, and alkaline phosphatase activity is detected with p-nitrophenyl phosphate substrate as an indication of YKL-40 concentration. It is understood that the methods of the invention can be practiced with these or other routine assays for detecting or determining a level of YKL-40 RNA or protein.

The following examples are intended to illustrate but not limit the present invention.

EXAMPLE I

Marker Panels for Non-Invasive Diagnosis of Liver Fibrosis

This example demonstrates that several serological markers can be combined together as a panel which is useful in differentiating fibrosis stages F2, F3 and F4 from stages F0 and F1 in HCV-infected patients.

Serum samples from 194 HCV patients positive for hepatitis C virus by RNA and immuno-analysis and having elevated alanine aminotransferase (ALT) levels were chosen at random from an existing serum library. Each of the patients had had a liver biopsy as part of their care. Patient samples were chosen to allow comparison of other routine blood markers and physical examination results attendant to routine medical care, including HCV viral load.

The inclusion criteria for the study were that the patient 1) have a confirmed hepatitis C infection at the time of liver biopsy and serum draw; 2) have undergone a liver biopsy as part of their medical care independent of the study; and 3) have previously given informed consent. Patients who did not give informed consent or who were incarcerated were excluded from the study.

Fibrosis scores (Metavir stage) for the 194 patients were established by histopathologic examination of a needle biopsy specimen prior to therapy according to the criteria set forth in The French Metavir Cooperative Study Group, *Hepatol.* 20:15–20 (1994). All Metavir fibrosis scores were established by the same pathologist. For all analyses, Metavir scores of F0 and F1 were grouped together as "no/mild" fibrosis, while scores of F2, F3 and F4 were grouped together as "moderate/severe" fibrosis. The fibrosis prevalence in the 194 patient group was determined to be 60% was based on the proportion of F2–F4 scores in the group as shown in

TABLE 2

COMPOSITION OF THE 194 HCV PATIENT STUDY POPULATION BY FIBROSIS STAGE

| Fibrosis stage | Number | Total F0–F1 or F2–F4 |
|---|---|---|
| F0 | 38 | F0–F1 = 78 |
| F1 | 40 | |
| F2 | 40 | F2–F4 = 116 |
| F3 | 39 | |
| F4 | 37 | |
| Total | 194 | Prevalence = 59.8% |

As shown in the table above, the panel of HCV patient samples included 37 samples with very high fibrosis stage (F4); 39 samples from patients with very low or zero fibrosis stage (F0); and 158 samples from patients with fibrosis stage F1, F2 or F3.

Serum samples were assayed for the presence of several putative fibrosis markers, including laminin, YKL-40, HA, TIMP-1, PIIINP, type IV collagen and α2-MG. Assays were performed using commercial kits according to manufacturers' instructions (see Table 3). The results obtained for the 194 samples analyzed for laminin, YKL-40, HA, TIMP-1, PIIINP, collagen type IV and α2-MG are shown in Table 4.

TABLE 3

COMMERCIALLY AVAILABLE KITS FOR DETECTION OF FIBROSIS MARKERS

| Marker | Manufacturer | Assay type | Catalogue number |
|---|---|---|---|
| Laminin | Chemicon Intl. (Temecula, CA) | ELISA | ECM310 |
| YKL-40 | Metra Biosystems (Mountain View, CA) | ELISA | 8020 |
| HA | Corgenix (Westminster, CO) | ELISA | 029001 |
| TIMP-1 | Amersham Pharmacia (Piscataway, NJ) | ELISA | RPN 2611 |
| PIIINP | Orion Diagnostica (Espoo, Finland) | RIA | 05903 |
| collagen IV | Iatron Laboratories (Tokyo, Japan) | RIA | KCAD1 |
| α2-MG | Beckman Coulter | Nephelometry | 449430 |

TABLE 4

RAW DATA FROM 194 HCV PATIENTS ANALYZED FOR LEVELS OF LAMININ, YKL-40, HA, TIMP-1, PIIINP, COLLAGEN TYPE IV AND α2-MG

| Sample ID | Patient | Laminin (ng/ml) | YKL-40 (ng/ml) | HA (ng/ml) | TIMP-1 (ng/ml) | PIIINP (ng/ml) | Coll IV (ng/ml) | α2-MG (mg/ml) |
|---|---|---|---|---|---|---|---|---|
| 100010 | B-A | 175.244 | 81.608 | 15.730 | 1308.802 | 2.288 | 1.737 | 3.03 |
| 100038 | P-B | 151.888 | 67.220 | 9.288 | 917.104 | 2.049 | 2.617 | 2.01 |
| 100044 | C-B | 187.811 | 60.757 | 44.127 | 1610.690 | 3.883 | 3.408 | 5.03 |
| 100059 | T-B | 232.082 | 51.002 | 22.583 | 1077.343 | 2.297 | 1.901 | 2.29 |
| 100069 | N-C | 285.269 | 131.726 | 73.851 | 2381.222 | 8.034 | 2.954 | 4.05 |
| 100077 | H-C | 268.685 | 47.709 | 18.066 | 1122.818 | 2.260 | 3.159 | 1.75 |
| 100090 | B-C | 263.426 | 26.370 | 47.339 | 1380.182 | 3.526 | 2.561 | 3.30 |
| 100127 | D-D | 279.580 | 166.113 | 105.505 | 1180.879 | 3.343 | 2.804 | 3.54 |
| 100167 | G-F | 274.533 | 482.708 | 341.132 | 2523.637 | 9.745 | 5.110 | 3.98 |
| 100175 | B-G | 266.903 | 95.808 | 27.721 | 1178.105 | 4.345 | 3.911 | 2.67 |
| 100178 | M-G | 211.613 | 159.040 | 25.669 | 1176.718 | 2.357 | 3.795 | 1.93 |
| 100182 | T-G | 246.686 | 55.391 | 8.889 | 1308.815 | 2.924 | 2.468 | 2.86 |
| 100198 | A-G | 226.372 | 48.441 | 13.901 | 1126.962 | 2.595 | 0.819 | 3.03 |
| 100209 | J-G | 288.524 | 83.925 | 5.051 | 1081.470 | 5.173 | 0.801 | 2.73 |
| 100229 | S-H | 253.561 | 110.020 | 46.568 | 1391.433 | 4.905 | 4.410 | 3.12 |
| 100238 | T-J | 229.781 | 38.076 | 29.516 | 1190.567 | 2.626 | 3.141 | 2.68 |
| 100245 | D-K | 279.768 | 270.250 | 171.481 | 2310.561 | 5.876 | 4.713 | 4.01 |
| 100247 | C-K | 244.559 | 131.482 | 10.219 | 1405.454 | 2.297 | 1.089 | 2.50 |
| 100250 | J-K | 262.136 | 101.729 | 54.821 | 1155.963 | 4.192 | 2.655 | 4.04 |
| 100252 | J-K | 260.998 | 61.366 | 57.275 | 1560.856 | 3.498 | 7.040 | 3.24 |
| 100253 | E-K | 292.189 | 173.917 | 168.768 | 1652.033 | 9.252 | 7.336 | 3.59 |
| 100254 | W-K | 288.551 | 477.560 | 102.775 | 1580.756 | 5.300 | 4.188 | 4.01 |
| 100271 | M-L | 278.201 | 89.900 | 69.651 | 1140.761 | 4.092 | 4.066 | 2.94 |
| 100276 | V-L | 257.309 | 176.112 | 12.196 | 1088.369 | 1.985 | 4.147 | 3.57 |
| 100284 | M-L | 224.339 | 130.263 | 31.822 | 1104.885 | 3.653 | 2.542 | 3.14 |
| 100290 | D-L | 199.542 | 541.552 | 50.429 | 1550.943 | 4.399 | 6.368 | 3.40 |
| 100294 | TRL | 281.501 | 217.328 | 200.436 | 2340.630 | 11.006 | 7.016 | 4.20 |
| 100301 | P-M | 285.543 | 430.475 | 29.772 | 1884.061 | 4.453 | 3.524 | 4.26 |
| 100313 | J-M | 301.751 | 188.062 | 45.539 | 1852.125 | 3.610 | 4.773 | 4.22 |
| 100323 | M-M | 223.002 | 626.140 | 144.334 | 2382.232 | 8.873 | 8.042 | 4.09 |
| 100334 | K-R | 173.320 | 63.317 | 38.516 | 1290.231 | 4.327 | 4.753 | 2.46 |
| 100339 | S-M | 184.085 | 36.125 | 12.049 | 1268.153 | 1.865 | 2.211 | 2.39 |
| 100340 | K-M | 206.582 | 57.496 | 22.015 | 974.475 | 2.315 | 0.819 | 2.80 |
| 100341 | T-M | 257.580 | 76.834 | 91.748 | 1492.882 | 3.976 | 4.793 | 3.00 |
| 100343 | D-M | 334.202 | 140.629 | 49.322 | 1098.199 | 4.092 | 2.412 | 3.12 |
| 100357 | P-M | 419.291 | 27.368 | 14.971 | 784.932 | 4.225 | 0.801 | 2.01 |
| 100374 | K-N | 300.366 | 28.231 | 36.608 | 1697.678 | 5.478 | 6.690 | 3.16 |
| 100379 | T-O | 233.496 | 75.711 | 26.906 | 1437.939 | 2.086 | 2.437 | 3.70 |
| 100382 | C-P | 206.796 | 44.461 | 6.034 | 989.007 | 2.214 | 4.409 | 2.14 |
| 100397 | R-R | 223.006 | 66.474 | 13.912 | 981.736 | 4.091 | 3.814 | 3.53 |
| 100410 | R-S | 224.775 | 36.605 | 37.499 | 1152.258 | 4.592 | 6.466 | 3.43 |
| 100438 | D-Q | 228.008 | 149.349 | 75.452 | 1682.636 | 7.734 | 7.039 | 3.89 |
| 100451 | H-R | 248.528 | 526.840 | 226.386 | 1961.029 | 10.505 | 7.113 | 3.36 |
| 100453 | A-R | 225.862 | 65.956 | 33.169 | 1421.632 | 2.786 | 3.465 | 3.79 |
| 100454 | O-R | 220.481 | 56.892 | 32.531 | 1125.960 | 3.003 | 7.014 | 3.68 |
| 100456 | S-S | 241.591 | 30.745 | 46.274 | 1337.355 | 5.182 | 2.411 | 2.81 |
| 100466 | S-S | 210.562 | 48.605 | 34.443 | 1482.475 | 4.286 | 4.754 | 3.27 |
| 100470 | D-S | 229.912 | 162.039 | 55.053 | 1684.159 | 6.806 | 3.640 | 3.10 |
| 100485 | C-T | 229.811 | 113.523 | 38.389 | 1247.547 | 3.901 | 3.291 | 4.11 |
| 100486 | M-T | 265.326 | 281.257 | 706.557 | 2716.589 | 15.362 | 11.975 | 2.82 |
| 100505 | L-W | 229.363 | 33.843 | 23.305 | 1149.367 | 3.397 | 2.889 | 3.29 |

TABLE 4-continued

RAW DATA FROM 194 HCV PATIENTS ANALYZED FOR
LEVELS OF LAMININ, YKL-40, HA, TIMP-1,
PIIINP, COLLAGEN TYPE IV AND α2-MG

| Sample ID | Patient | Laminin (ng/ml) | YKL-40 (ng/ml) | HA (ng/ml) | TIMP-1 (ng/ml) | PIIINP (ng/ml) | Coll IV (ng/ml) | α2-MG (mg/ml) |
|---|---|---|---|---|---|---|---|---|
| 100519 | R-W | 204.646 | 68.632 | 10.431 | 845.571 | 3.852 | 6.815 | 2.52 |
| 100547 | S-G | 223.959 | 75.711 | 8.257 | 1000.623 | 4.286 | 3.090 | 2.92 |
| 100638 | J-P | 265.819 | 264.250 | 68.361 | 2095.698 | 15.945 | 7.418 | 4.67 |
| 100640 | M-V | 170.293 | 43.770 | 17.728 | 1200.584 | 4.755 | 5.561 | 3.50 |
| 100006 | L-A | 135.628 | 75.349 | 79.430 | 1354.782 | 6.612 | 3.477 | 3.14 |
| 100009 | R-A | 157.239 | 72.429 | 21.947 | 932.635 | 2.080 | 3.050 | 1.96 |
| 100011 | A-B | 136.197 | 251.237 | 149.932 | 2004.294 | 7.600 | 4.853 | 3.57 |
| 100016 | E-A | 161.133 | 272.434 | 186.536 | 1900.341 | 9.341 | 9.071 | 3.08 |
| 100021 | E-AV | 184.000 | 537.630 | 102.420 | 2456.883 | 4.863 | 6.157 | 3.97 |
| 100023 | C-B | 126.346 | 194.523 | 47.976 | 1540.914 | 7.000 | 4.488 | 3.21 |
| 100027 | D-B | 133.660 | 75.820 | 33.912 | 1519.528 | 2.966 | 3.286 | 3.51 |
| 100030 | R-B | 140.584 | 50.007 | 153.135 | 1219.549 | 3.237 | 5.200 | 1.89 |
| 100035 | K-B | 124.645 | 37.383 | 60.934 | 1214.060 | 3.582 | 3.620 | 2.41 |
| 100036 | G-B | 152.864 | 87.596 | 369.681 | 1305.790 | 3.163 | 4.391 | 2.71 |
| 100041 | M-B | 168.422 | 42.376 | 143.372 | 1502.562 | 6.667 | 3.692 | 3.10 |
| 100042 | M-B | 138.754 | 211.387 | 266.568 | 2899.870 | 8.233 | 8.559 | 3.98 |
| 100043 | C-B | 111.743 | 30.883 | 17.447 | 1168.327 | 5.488 | 2.343 | 2.76 |
| 100045 | V-B | 164.940 | 241.063 | 221.249 | 2010.088 | 9.097 | 4.512 | 3.76 |
| 100051 | K-B | 154.743 | 222.409 | 131.122 | 1600.554 | 4.863 | 4.075 | 3.43 |
| 100055 | D-B | 146.817 | 110.018 | 84.447 | 1827.668 | 3.188 | 4.439 | 5.72 |
| 100065 | G-B | 134.349 | 72.429 | 112.148 | 1455.905 | 3.353 | 3.002 | 4.02 |
| 100071 | R-C | 135.011 | 74.407 | 30.352 | 1485.573 | 2.820 | 3.120 | 3.29 |
| 100073 | G-C | 146.785 | 63.761 | 43.312 | 1530.873 | 3.027 | 2.040 | <0.75 |
| 100074 | L-C | 151.514 | 80.248 | 49.917 | 1647.700 | 5.036 | 3.286 | 3.11 |
| 100078 | R-C | 163.144 | 213.365 | 45.839 | 1399.880 | 3.393 | 2.297 | 2.61 |
| 100081 | A-C | 147.915 | 45.862 | 56.686 | 1346.315 | 4.056 | 4.707 | 2.37 |
| 100084 | G-C | 144.665 | 43.130 | 116.238 | 1736.670 | 5.337 | 6.702 | <0.75 |
| 100091 | P-C | 171.782 | 215.249 | 33.321 | 1999.807 | 5.096 | 3.835 | 3.75 |
| 100093 | M-C | 133.786 | 35.499 | 105.726 | 1499.707 | 5.983 | 5.876 | 2.85 |
| 100099 | S-C | 174.239 | 49.159 | 28.163 | 1392.574 | 4.381 | 5.876 | 3.18 |
| 100100 | D-C | 181.284 | 68.095 | 82.324 | 1613.489 | 5.552 | 5.547 | 3.71 |
| 100103 | J-C | 151.396 | 74.849 | 55.720 | 1666.282 | 4.771 | 3.955 | 3.57 |
| 100104 | C-C | 128.182 | 38.890 | 13.719 | 1100.784 | 3.798 | 5.324 | 2.21 |
| 100106 | S-C | 170.685 | 41.811 | 37.449 | 1280.697 | 5.096 | 4.464 | 2.52 |
| 100107 | J-C | 103.835 | 27.397 | 32.334 | 1416.481 | 2.910 | 3.740 | 2.57 |
| 100108 | J-C | 148.294 | 145.629 | 52.822 | 1884.389 | 4.484 | 3.597 | 4.62 |
| 100115 | S-DLT | 134.784 | 108.134 | 96.415 | 1597.696 | 8.860 | 5.225 | 3.48 |
| 100121 | R-D | 149.335 | 74.878 | 34.109 | 1759.752 | 5.912 | 3.716 | 4.36 |
| 100124 | R-D | 134.766 | 130.367 | 35.486 | 1569.219 | 2.489 | 4.877 | 1.21 |
| 100125 | B-D | 170.790 | 67.078 | 97.770 | 2245.776 | 7.261 | 5.876 | 3.63 |
| 100126 | D-D | 134.313 | 117.116 | 65.560 | 1970.476 | 2.775 | 3.788 | 3.04 |
| 100129 | E-D | 159.707 | 60.388 | 28.962 | 1651.995 | 5.195 | 4.902 | 3.41 |
| 100131 | J-D | 155.166 | 119.774 | 31.852 | 1579.186 | 3.015 | 3.405 | 2.73 |
| 100133 | M-D | 146.280 | 24.371 | 75.729 | 2098.560 | 3.225 | 3.788 | 1.74 |
| 100135 | H-E | 167.472 | 41.600 | 66.767 | 1369.735 | 3.200 | 3.429 | 4.20 |
| 100137 | D-E | 158.406 | 25.104 | 68.740 | 1346.906 | 3.828 | 3.405 | 2.69 |
| 100139 | S-E | 139.877 | 38.484 | 42.708 | 1388.605 | 4.215 | 2.814 | 4.05 |
| 100140 | L-E | 158.942 | 30.695 | 181.056 | 1585.482 | 7.476 | 4.977 | 3.32 |
| 100141 | W-E | 136.761 | 185.300 | 179.774 | 2045.873 | 9.097 | 9.872 | 2.89 |
| 100142 | R-E | 119.383 | 62.037 | 16.170 | 888.744 | 3.286 | 2.673 | 2.07 |
| 100143 | D-E | 131.717 | 33.779 | 29.179 | 1072.170 | 2.978 | 3.144 | 1.91 |
| 100147 | D-E | 132.426 | 77.159 | 35.912 | 1285.138 | 3.515 | 2.696 | 2.12 |
| 100150 | D-E | 120.207 | 19.056 | 155.043 | 1488.729 | 2.298 | 4.196 | 3.66 |
| 100151 | D-F | 125.885 | 35.735 | 51.625 | 1243.711 | 3.447 | 3.525 | 3.05 |
| 100155 | C-H | 146.728 | 29.137 | 54.330 | 1242.340 | 4.733 | 3.573 | 3.15 |
| 100159 | M-H | 136.303 | 31.336 | 106.675 | 1567.716 | 4.151 | 3.525 | 3.51 |
| 100161 | JF-F | 155.052 | 1710.890 | 572.598 | 1966.460 | 6.226 | 4.634 | 4.27 |
| 100163 | M-F | 153.221 | 785.420 | 211.173 | 2167.501 | 8.269 | 5.698 | 3.57 |
| 100175a | B-G | 148.403 | 55.347 | 130.093 | 1282.502 | 5.296 | 4.537 | 2.79 |
| 100181 | M-G | 137.986 | 69.735 | 31.119 | 1384.651 | 2.813 | 3.097 | 1.89 |
| 100183 | D-G | 168.842 | 181.909 | 58.358 | 1499.596 | 3.101 | 3.405 | 3.86 |
| 100186 | M-G | 184.148 | 2258.120 | 347.854 | 5271.196 | 11.670 | 7.756 | 3.82 |
| 100200 | R-G | 148.660 | 158.906 | 143.510 | 1939.499 | 5.530 | 6.080 | 4.02 |
| 100208 | R-G | 156.210 | 94.021 | 36.624 | 1379.174 | 5.339 | 4.366 | <0.75 |
| 100221 | ND-H | 117.196 | 38.393 | 88.913 | 1375.112 | 2.610 | 5.274 | 3.76 |
| 100222 | J-H | 106.131 | 34.544 | 31.603 | 1054.973 | 2.580 | 2.955 | 3.40 |
| 100229a | S-H | 125.123 | 53.139 | 73.989 | 1567.731 | 3.828 | 3.788 | 2.78 |
| 100237 | J-J | 140.718 | 397.625 | 578.952 | 1824.407 | 11.836 | 6.675 | 2.46 |
| 100268 | C-L | 155.864 | 76.151 | 86.977 | 2060.140 | 10.963 | 6.310 | 3.66 |
| 100270 | T-L | 176.060 | 24.738 | 38.749 | 1579.990 | 2.549 | 2.625 | 3.35 |
| 100278 | S-L | 153.789 | 48.840 | 52.524 | 1367.051 | 3.039 | 3.167 | 1.91 |
| 100279 | L-LG | 163.352 | 139.202 | 34.492 | 1223.652 | 2.921 | 4.099 | 2.37 |

TABLE 4-continued

RAW DATA FROM 194 HCV PATIENTS ANALYZED FOR
LEVELS OF LAMININ, YKL-40, HA, TIMP-1,
PIIINP, COLLAGEN TYPE IV AND α2-MG

| Sample ID | Patient | Laminin (ng/ml) | YKL-40 (ng/ml) | HA (ng/ml) | TIMP-1 (ng/ml) | PIIINP (ng/ml) | Coll IV (ng/ml) | α2-MG (mg/ml) |
|---|---|---|---|---|---|---|---|---|
| 100287 | R-L | 164.414 | 636.110 | 232.253 | 3285.078 | 14.450 | 9.448 | 4.19 |
| 100291 | MS-L | 152.863 | 197.500 | 42.925 | 2144.445 | 2.180 | 1.993 | 3.78 |
| 100293 | D-L | 147.479 | 104.509 | 27.209 | 1559.538 | 3.151 | 2.696 | 1.83 |
| 100302 | A-M | 201.715 | 1021.070 | 159.330 | 3317.515 | 12.498 | 8.383 | 4.83 |
| 100306 | JT-M | 125.203 | 115.289 | 83.960 | 1722.987 | 3.842 | 2.413 | 4.16 |
| 100307 | D-M | 128.095 | 23.612 | 10.882 | 1378.118 | 3.339 | 3.382 | 1.42 |
| 100313a | J-McA | 164.201 | 192.417 | 76.599 | 1966.287 | 3.828 | 5.523 | 3.89 |
| 100315 | K-MF | 153.427 | 113.449 | 112.430 | 2118.580 | 3.515 | 4.561 | 4.46 |
| 100317 | M-McM | 165.245 | 94.693 | 144.632 | 1611.495 | 4.588 | 3.215 | 1.84 |
| 100320 | D-M | 159.724 | 782.150 | 106.161 | 1581.345 | 13.215 | 5.597 | 2.33 |
| 100322 | R-M | 120.098 | 39.914 | 51.444 | 1443.789 | 2.809 | 3.644 | 3.21 |
| 100327 | K-R | 168.143 | 194.521 | 101.231 | 1738.827 | 4.295 | 3.835 | 4.35 |
| 100336 | ES-M | 165.374 | 135.711 | 36.329 | 1556.071 | 2.932 | 2.508 | 3.49 |
| 100347 | E-M | 173.070 | 69.889 | 16.945 | 1710.951 | 4.808 | 3.859 | 3.29 |
| 100348 | A-M | 207.186 | 75.06 | 301.583 | 1334.475 | 3.299 | 4.585 | 3.36 |
| 100350 | J-M | 154.867 | 4.418 | 22.250 | 1388.371 | 4.087 | 3.238 | 1.60 |
| 100358 | A-M | 140.022 | 15.549 | 88.786 | 1247.147 | 4.502 | 4.682 | 1.57 |
| 100365 | A-M | 96.324 | 26.329 | 43.344 | 1170.887 | 5.381 | 2.040 | 2.12 |
| 100367 | B-M | 161.274 | 30.273 | 46.174 | 1469.088 | 3.089 | 2.790 | 3.59 |
| 100388 | A-P | 230.782 | 275.681 | 938.015 | 4245.175 | 20.496 | 9.669 | 5.98 |
| 100395 | D-R | 125.908 | 24.226 | 15.309 | 1299.599 | 2.478 | 4.415 | 3.52 |
| 100397a | R-R | 179.186 | 56.479 | 100.853 | 1455.947 | 9.769 | 4.172 | 3.62 |
| 100398 | C-R | 151.391 | 29.397 | 11.833 | 1100.156 | 2.652 | 2.932 | 2.28 |
| 100403 | L-P | 179.146 | 321.607 | 350.713 | 2061.218 | 8.938 | 4.977 | 2.28 |
| 100404 | ML-P | 179.163 | 1060.240 | 141.902 | 2248.495 | 5.959 | 4.123 | 4.07 |
| 100414 | S-S | 184.451 | 70.941 | 40.126 | 1048.761 | 2.549 | 3.026 | 3.18 |
| 100424 | A-P | 158.538 | 62.439 | 167.519 | 1320.841 | 5.509 | 5.448 | 3.88 |
| 100443 | J-R | 112.348 | 40.703 | 21.470 | 1045.054 | 2.663 | 5.647 | 4.34 |
| 100450 | M-R | 186.892 | 200.744 | 203.399 | 1287.107 | 2.586 | 4.040 | 3.77 |
| 100472 | T-S | 127.877 | 119.759 | 21.867 | 797.753 | 2.787 | 3.962 | 1.97 |
| 100474 | J-S | 118.319 | 55.427 | 19.699 | 939.914 | 2.287 | 3.524 | 3.15 |
| 100482 | J-T | 125.011 | 33.428 | 39.749 | 1099.832 | 5.159 | 4.386 | 2.56 |
| 100483 | J-T | 136.978 | 18.006 | 33.467 | 1003.831 | 2.586 | 4.485 | 2.06 |
| 100488 | M-T | 178.106 | 51.908 | 123.723 | 1345.743 | 4.464 | 6.053 | 3.84 |
| 100495 | J-V | 180.283 | 219.322 | 93.680 | 1734.925 | 8.387 | 4.064 | 3.82 |
| 100502 | D-V | 114.380 | 153.296 | 22.649 | 1136.728 | 2.774 | 4.757 | 4.47 |
| 100503 | J-W | 149.928 | 453.095 | 92.918 | 1422.332 | 5.581 | 4.114 | 3.15 |
| 100513 | M-W | 117.649 | 53.027 | 100.853 | 1335.730 | 5.092 | 4.757 | 3.74 |
| 100528 | D-W | 189.040 | 37.248 | 26.158 | 1103.495 | 4.642 | 3.215 | 2.90 |
| 100530 | M-W | 106.100 | 40.234 | 20.490 | 924.291 | 3.297 | 3.988 | 2.29 |
| 100534 | D-A | 135.702 | 37.357 | 91.410 | 1421.072 | 3.374 | 3.135 | 3.26 |
| 100539 | M-DB | 167.910 | 474.960 | 104.470 | 2158.238 | 4.957 | 5.566 | 3.99 |
| 100540 | A-B | 135.980 | 54.815 | 183.589 | 1881.935 | 3.068 | 4.485 | 3.34 |
| 100546 | D-F | 113.363 | 75.942 | 47.682 | 1207.833 | 2.633 | 3.055 | 1.57 |
| 100557 | T-L | 121.746 | 58.286 | 27.704 | 1297.060 | 3.842 | 2.060 | 1.83 |
| 100560 | C-N | 194.265 | 142.696 | 91.041 | 2338.303 | 6.332 | 3.267 | 4.25 |
| 100564 | D-R | 169.241 | 250.713 | 65.865 | 2407.901 | 5.502 | 4.534 | 3.52 |
| 100569 | J-DC | 160.145 | 64.634 | 43.744 | 1349.485 | 5.962 | 3.421 | 3.78 |
| 100572 | K-K | 162.517 | 260.632 | 209.581 | 1729.746 | 9.292 | 6.191 | 2.70 |
| 100585 | K-Z | 171.277 | 162.336 | 126.433 | 2030.404 | 8.907 | 4.881 | 4.71 |
| 100594 | R-M | 114.193 | 216.295 | 42.261 | 1678.540 | 3.545 | 3.602 | 3.26 |
| 100603 | M-S | 114.071 | 61.460 | 34.332 | 1693.071 | 4.464 | 4.188 | 2.92 |
| 100611 | P-F | 178.856 | 269.956 | 92.721 | 896.077 | 3.960 | 3.524 | 3.96 |
| 100614 | J-McA | 204.794 | 245.159 | 322.970 | 3470.966 | 11.393 | 6.814 | 5.32 |
| 100617 | C-W | 159.292 | 51.343 | 38.850 | 1504.544 | 5.859 | 4.974 | 3.60 |
| 100630 | E-AV | 140.072 | 34.778 | 59.454 | 1091.420 | 1.969 | 3.161 | 3.34 |
| 100637 | R-B | 179.987 | 59.477 | 137.723 | 2077.095 | 4.726 | 3.002 | 4.24 |
| 101013 | T-H | 177.189 | 507.415 | 237.499 | 1556.336 | 9.381 | 8.910 | 3.36 |
| 101118 | G-S | 163.553 | 282.057 | 150.713 | 2348.845 | 6.231 | 7.161 | 3.93 |
| 101137 | S-S | 175.291 | 2049.970 | 715.601 | 3318.137 | 11.450 | 8.458 | 3.71 |
| 101257 | M-F | 155.324 | 40.730 | 49.441 | 1082.686 | 3.240 | 3.421 | 1.71 |
| 101275 | J-C | 121.598 | 143.292 | 45.227 | 1454.509 | 1.915 | 2.788 | 4.69 |
| 101284 | R-F | 123.312 | 16.825 | 42.048 | 1072.891 | 4.386 | 3.679 | 1.64 |
| 101321 | H-P | 180.159 | 180.091 | 367.681 | 2235.931 | 11.450 | 10.045 | 3.37 |
| 101322 | A-P | 133.640 | 269.262 | 244.520 | 2015.508 | 9.119 | 8.458 | 4.01 |
| 101335 | L-S | 164.947 | 64.238 | 208.719 | 2545.531 | 11.018 | 6.930 | 3.90 |
| 101336 | L-S | 156.847 | 741.300 | 72.664 | 1387.281 | 6.097 | 4.683 | 3.73 |
| 101351 | P-F | 128.701 | 12.461 | 99.050 | 1557.519 | 5.486 | 4.161 | 4.01 |
| 101441 | R-H | 104.993 | 176.909 | 354.512 | 1338.637 | 5.271 | 6.445 | 3.50 |
| 101478 | G-S | 142.642 | 63.543 | 149.266 | 1296.972 | 3.859 | 4.411 | 2.64 |
| 101565 | D-A | 132.117 | 74.355 | 187.250 | 1206.734 | 5.962 | 4.782 | 2.92 |

Clinical performance parameters were analyzed for the combinations of markers best able to differentiate the presence of significant fibrosis (F2–F4) from no/mild fibrosis (F0–F1) using various statistical algorithms. The statistical algorithms analyzed included univariate analysis, receiver operating characteristic curves (ROC), logistic regression, discriminant function analysis, and factorial design optimization.

The results of ROC analysis are shown in Table 5. The area under the curve (AUC) values represent relative diagnostic value of a single marker at the indicated cut-off. As can be seen by the decreasing AUC values, HA was shown to have the best diagnostic value when used alone at the indicated cut-off, followed by PIIINP, TIMP-1, α2-MG and collagen type IV.

TABLE 5

ROC ANALYSIS

|  | AUC | Sensitivity | Specificity | Cutoff |
|---|---|---|---|---|
| HA | 0.821 | 90.0% | 62.0% | 35.5 ng/ml |
| PIIINP | 0.777 | 90.8% | 39.2% | 3.0 ng/ml |
| TIMP-1 | 0.773 | 90.8% | 43.0% | 1190.6 ng/ml |
| α2-macroglobulin | 0.722 | 90.5% | 34.6% | 2.4 mg/ml |
| Collagen Type IV-7S | 0.726 | 90.8% | 24.1% | 2.79 ng/ml |
| YKL-40 | 0.696 | 90.8% | 19.0% | 34.5 ng/ml |
| Laminin | 0.524 | 90.7% | 16.5% | 125.2 ng/ml |

Clinical performance parameters for various combinations of fibrosis markers are shown in Table 6. The best subsets, including single markers as well as combinations of two to four markers and algorithms for discriminating F0–F1 from F2–F4, were generated by logistic regression. The markers included PIIINP, α2-MG, laminin and type IV collagen. As shown in Table 5, the diagnostic performance parameters (sensitivity, specificity, PPV and NPV) were similar for the two, three and four-marker combinations identified by logistic regression in the study population, which had a fibrosis prevalence of about 60% (see lines 2–4 and 6–9).

As shown in Table 6, line 5, stepwise discriminant function analysis (SAS) resulted in identification of the 3-marker subset (PIIINP, α2-MG and laminin). The clinical performance of this combination was similar to the marker combinations identified using logistic regression.

Design of experiments software (DOE KISS, Build 8, Air Academy Associates) was used to simultaneously optimize the cutoffs of multiple variables to obtain the best performance of the panel of tests in predicting fibrosis. Using DOE KISS, a computer-aided central composite design for a combination of markers was generated; this design matrix consisted of a series of combinations of cutoffs for each of the markers in the combination. The results from these experiments (sensitivity, specificity and accuracy) for differentiating F0–F1 from F2–F4 fibrosis were recorded in the design sheet in DOE. Regression analysis was performed for each of the parameters (sensitivity, specificity and accuracy) to give cutoff values for each of the variables in the combination to achieve maximum performance for that parameter.

The five markers with best diagnostic performance in an ROC analysis (highest AUC) were HA, PIIINP, TIMP-1, α2-MG and type IV collagen (see Table 5). Cutoffs for each of the markers in this 5-marker panel were optimized for maximum accuracy. The results shown in Table 6, line 10, indicate that, at the optimum accuracy (69.6%), the specificity was too low to be useful (32.9%) while the sensitivity was high (94.8%). Similar results were obtained when the markers were optimized for sensitivity or specificity. Regression analysis showed that TIMP-1 did not have a significant effect on the accuracy, sensitivity or specificity of this 5-marker panel.

TABLE 6

PERFORMANCE OF VARIOUS MARKER PANELS

|  | Markers | Method/ Model | Sens. | Spec. | Prevalence 59.3% PPV | NPV | Acc. | Prevalence 20% PPV | NPV | Acc. |
|---|---|---|---|---|---|---|---|---|---|---|
| 1 | HA | N/A cut-off 60 ug/ml | 64.96% | 82.05% | 84.44% | 60.95% |  | 47.50% | 90.35% | 78.63% |
| 2 | PIIINP | Logistic Best subset of 1 | 74.36% | 58.97% | 73.11% | 60.53% |  | 31.18% | 90.20% | 62.05% |
| 3 | PIIINP, AMG | Logistic Best subset of 2 | 80.53% | 63.63% | 76.86% | 68.54% |  | 31.18% | 90.20% | 62.05% |
| 4 | PIIINP, AMG, Laminin | Logistic Best subset of 3 | 78.76% | 67.53% | 78.44% | 67.95% |  | 37.75% | 92.71% | 69.78% |
| 5 | PIIINP, AMG, Laminin | Discriminant Stepwise selection | 78.76% | 67.53% | 78.44% | 67.95% |  | 37.75% | 92.71% | 69.78% |
| 6 | PIIINP, AMG, Laminin, Coll IV | Logistic Best subset of 4 | 78.76% | 64.94% | 77.11% | 67.09% |  | 35.96% | 92.44% | 67.70% |
| 7 | PIIINP, AMG, lminin, YKL-40 | Logistic Second best subset of 4 | 77.87% | 67.53% | 78.25% | 67.05% |  | 37.48% | 92.43% | 69.60% |
| 8 | PIIINP, AMG, Coll IV, YKL-40 | Logistic Third best subset of 4 | 78.76% | 70.13% | 79.82% | 68.76% |  | 39.73% | 92.96% | 71.86% |
| 9 | PIIINP, AMG, TIMP-1 | Logistic "Forced" selection | 78.76% | 64.94% | 77.11% | 67.09% |  | 35.96% | 92.44% | 67.70% |
| 10 | HA, PIIINP, AMG Coll IV, TIMP-1 | DOE (for acc.) N/A | 94.78% | 32.91% | 67.28% | 81.25% | 69.59% | 26.1% | 96.2% | 45.3% |
| 11 | HA, PIIINP, Coll IV, AMG | DOE (for acc.) N/A | 79.13% | 75.95% | 82.73% | 71.43% | 77.84% | 45.13% | 93.57% | 76.59% |

TABLE 6-continued

PERFORMANCE OF VARIOUS MARKER PANELS

| | | | | | Prevalence 59.3% | | | Prevalence 20% | | |
|---|---|---|---|---|---|---|---|---|---|---|
| Markers | Method/Model | Sens. | Spec. | PPV | NPV | Acc. | PPV | NPV | Acc. |
| 12 HA, CollIV, AMG | DOE (for acc.) N/A | 95.65% | 29.11% | 66.27% | 82.14% | 68.56% | 25.2% | 96.4% | 42.4% |
| 13 HA, PIIINP, AMG | DOE (for acc.) N/A | 78.26% | 75.95% | 82.57% | 70.59% | 77.32% | 44.86% | 93.32% | 76.41% |
| 14 HA, AMG (B) | DOE (for acc.) N/A | 84.35% | 73.42% | 82.20% | 76.32% | 79.90% | 44.24% | 94.94% | 75.60% |
| 15 TIMP-1, HA, AMG | DOE (for acc.) | 83.48% | 75.95% | 83.48% | 75.95% | 80.41% | 46.46% | 94.84% | 77.46% |
| 16 YKL-40, HA, AMG | DOE (for acc.) | 82.61% | 75.95% | 83.33% | 75.00% | 79.90% | 46.20% | 94.59% | 77.28% |
| 17 HA, reflex with Coll IV and AMG | Logistic Positives reflexed | 86.32% | 70.51% | 81.45% | 77.46% | 80.00% | 42.26% | 95.38% | 73.68% |

A similar 4-marker panel was analyzed by DOE as shown in Table 6, line 11. With TIMP-1 excluded, the four-marker panel was optimized for accuracy (77.8%) to give a sensitivity and specificity of 79.1% and 79.5%, respectively. These results demonstrate that the four-marker panel of HA, PIIINP, α2-MG and collagen IV has more value in differentiating F0–F1 fibrosis from F2–F4 fibrosis than a five-marker panel made up of HA, PIIINP, α2-MG, collagen IV and TIMP-1.

Several three-marker subsets of the four-marker panel also were analyzed by DOE. Line 12 shows the results obtained for the combination of HA, collagen and α2-MG with the results optimized for accuracy. This three-marker panel gave a very low specificity of less than 30%. In contrast, when a three-marker panel made up of HA, PIIINP and α2-MG was optimized for accuracy, performance was similar to the four-marker panel (compare lines 13 and 11 of Table 6).

A similar analysis of the two-marker panel of HA and α2-MG gave the results shown in line 14 of Table 6. This combination gave an improvement in specificity over the three-marker panel of HA, PIIINP and α2-MG (84.4% compared to 78.3%).

TIMP-1, which was observed to be a good discriminator of fibrosis in the univariate analysis, was added to the two-marker panel. As shown in line 15, the performance of the HA, α2-MG and TIMP-1 three-marker panel was similar to that obtained with the two-marker panel, and the sensitivity was improved as compared to the three-marker HA/PIIINP/α2-MG panel (83.5% sensitivity compared to 78.3%). Furthermore, in preliminary regression analysis, TIMP-1 contributed significantly to discrimination of fibrosis in a study population with a high prevalence of severe fibrosis.

Another three-marker panel, made up of HA, α2-MG and YKL-40, also was optimized for accuracy in differentiating F0–F1 from F2–F4 fibrosis. As shown in Table 6, line 16, this three marker panel had a performance similar to the α2-MG/HA/TIMP-1 panel.

In sum, these results indicate that a α2-MG/HA/TIMP-1 or α2-MG/HA/YKL-40 panel can be useful in differentiating F0–F1 from F2–F4 fibrosis.

EXAMPLE II

Dual Optimization Strategy for Analysis of the α2-MG/HA/TIMP Three-Marker Panel

This example describes the use of multiple cut-offs for α2-MG-, HA- and TIMP-1 to achieve a relatively high degree of accuracy in a subset of a total patient population assayed.

Using the three-marker panel α2-MG/HA/TIMP-1 with cutoffs for α2-MG, HA- and TIMP-1 set at 35 ng/ml, 2 mg/ml, and 1000 ng/ml, respectively, samples were determined to be positive when all three of their variables were above the cut-off values, and were therefore negative when one or more of the α2-MG, HA or TIMP-1 levels were below the assigned cut-off value. As shown in Table 7, in the 194 patient population, there were a total of 72 negative results, 15 of which were false negatives, giving a negative predictive value (NPV) of 79% at the study prevalence of about 60% fibrosis %. At a prevalence of 30%, which is typical of the prevalence in a hepatology clinic, the negative predictive value is over 92%, which is useful in ruling out the presence of F2–F4 fibrosis (likelihood ratio 0.22).

TABLE 7

PERFORMANCE OF α2-MG/HA/TIMP-1 PANEL WITH DUAL OPTIMIZATION STRATEGY IN POPULATIONS WITH VARIOUS DISEASE PREVALENCES

| | Prevalence 0.598 | | | Prevalence 0.300 | | | Prevalence 0.200 | | | Prevalence 0.100 | | |
|---|---|---|---|---|---|---|---|---|---|---|---|---|
| | Fib + | Fib − | | Fib + | Fib − | | Fib + | Fib − | | Fib + | Fib − | |
| | Optimization for sensitivity to rule out fibrosis | | | | | | | | | | | |
| | $X1 = 2.0$ mg/ml for α2-MG $Y1 = 35.00$ ng/ml for HA $Z1 = 1000.00$ ng/ml for TIMP-1 | | | | | | | | | | | |
| Test + | 101 | 21 | 122 | 261 | 188 | 450 | 174 | 215 | 390 | 87 | 242 | 329 |
| Test − | 15 | 57 | 72 | 39 | 512 | 550 | 26 | 585 | 610 | 13 | 658 | 671 |
| | 116 | 78 | 194 | 300 | 700 | 1000 | 200 | 800 | 1000 | 100 | 900 | 1000 |

TABLE 7-continued

PERFORMANCE OF α2-MG/HA/TIMP-1 PANEL WITH DUAL OPTIMIZATION
STRATEGY IN POPULATIONS WITH VARIOUS DISEASE PREVALENCES

| | | | | | | | | | | | | |
|---|---|---|---|---|---|---|---|---|---|---|---|---|
| Sens. | 87.07% | LR + | 3.23 | 87.07% | LR + | 3.23 | 87.07% | LR + | 3.23 | 87.07% | LR + | 3.23 |
| Spec. | 73.08% | LR − | 0.18 | 73.08% | LR − | 0.18 | 73.08% | LR − | 0.18 | 73.08% | LR − | 0.18 |
| PPV | 82.79% | | | 58.09% | | | 44.71% | | | 26.43% | | |
| NPV | 79.17% | | | 92.95% | | | 95.76% | | | 98.07% | | |
| Accuracy | 81.44% | | | 77.27% | | | 75.88% | | | 74.48% | | |

Optimization for specificity to rule in fibrosis
X1 = 2.0 mg/ml for α2-MG  Y1 = 60.00 ng/ml for HA  Z1 = 1575.00 for TIMP-1 ng/ml

| | | | | | | | | | | | | |
|---|---|---|---|---|---|---|---|---|---|---|---|---|
| Test + | 53 | 1 | 54 | 137 | 9 | 146 | 91 | 10 | 102 | 46 | 12 | 57 |
| Test − | 48 | 20 | 68 | 124 | 179 | 304 | 83 | 205 | 288 | 41 | 231 | 272 |
| Equiv | 101 | 21 | 122 | 261 | 188 | 450 | 174 | 215 | 390 | 87 | 242 | 329 |
| Sens. | 52.48% | LR + | 11.02 | 52.48% | LR + | 11.02 | 52.48% | LR + | 11.02 | 52.48% | LR + | 11.02 |
| Spec. | 95.24% | LR − | 0.50 | 95.24% | LR − | 0.50 | 95.24% | LR − | 0.50 | 95.24% | LR − | 0.50 |
| PPV | 98.15% | | | 93.86% | | | 89.91% | | | 79.84% | | |
| NPV | 29.41% | | | 59.11% | | | 71.25% | | | 84.80% | | |
| Accuracy | 59.84% | | | 70.40% | | | 76.12% | | | 83.93% | | |

Final performance after dual optimization

| | | | | | | | | | | | | |
|---|---|---|---|---|---|---|---|---|---|---|---|---|
| | 53 | 1 | 54 | 137 | 9 | 146 | 91 | 10 | 102 | 46 | 12 | 57 |
| | 63 | 77 | 140 | 163 | 691 | 854 | 109 | 790 | 898 | 54 | 888 | 943 |
| | 116 | 78 | 194 | 300 | 700 | 1000 | 200 | 800 | 1000 | 100 | 900 | 1000 |
| Sens. | 45.69% | LR + | 35.64 | 45.69% | LR + | 35.64 | 45.69% | LR + | 35.64 | 45.69% | LR + | 35.64 |
| Spec. | 98.72% | LR − | 0.55 | 98.72% | LR − | 0.55 | 98.72% | LR − | 0.55 | 98.72% | LR − | 0.55 |
| PPV | 98.15% | | | 93.86% | | | 89.91% | | | 79.84% | | |
| NPV | 55.00% | | | 80.92% | | | 87.91% | | | 94.24% | | |
| Accuracy | 67.01% | | | 82.81% | | | 88.11% | | | 93.42% | | |

| | | | | | | | |
|---|---|---|---|---|---|---|---|
| Population | 194 | | Population | 1000 | Population | 1000 | Population | 1000 |
| Prevalence | 0.598 | | Prevalence | 0.300 | Prevalence | 0.200 | Prevalence | 0.100 |
| False Negative | 15 | | False Negative | 39 | False Negative | 26 | False Negative | 13 |
| False Positive | 1 | | False Positive | 9 | False Positive | 10 | False Positive | 12 |
| Total Incorrect | 16 | | Total Incorrect | 48 | Total Incorrect | 36 | Total Incorrect | 24 |
| Total Correct | 110 | 87.3% | Total Correct | 649 | Total Correct | 676 | Total Correct | 703 |

2nd Round

| | | | | | | | | |
|---|---|---|---|---|---|---|---|---|
| Fib + Equivocal | 48 | | Fib + Equivocal | 124 | Fib + Equivocal | 83 | Fib + Equivocal | 41 |
| Fib − Equivocal | 20 | | Fib − Equivocal | 179 | Fib − Equivocal | 205 | Fib − Equivocal | 231 |
| Total Equivocal | 68 | 35.1% | Total Equivocal | 304 | Total Equivocal | 288 | Total Equivocal | 272 |

Final performance after dual optimization without equivocals

| | Prevalence 0.598 | | | Prevalence 0.300 | | | Prevalence 0.200 | | | Prevalence 0.100 | | |
|---|---|---|---|---|---|---|---|---|---|---|---|---|
| | Fib + | Fib − | | Fib + | Fib − | | Fib + | Fib − | | Fib + | Fib − | |
| Test + | 53 | 1 | 54 | 137 | 9 | 146 | 91 | 10 | 102 | 46 | 12 | 57 |
| Test − | 15 | 57 | 72 | 39 | 512 | 550 | 26 | 585 | 610 | 13 | 658 | 671 |
| | 68 | 58 | 126 | 176 | 521 | 696 | 117 | 595 | 712 | 59 | 669 | 728 |
| Sens. | 77.94% | LR + | 45.21 | 77.94% | LR + | 45.21 | 77.94% | LR + | 45.21 | 77.94% | LR + | 45.21 |
| Spec. | 98.28% | LR − | 0.22 | 98.28% | LR − | 0.22 | 98.28% | LR − | 0.22 | 98.28% | LR − | 0.22 |
| PPV | 98.15% | | | 93.86% | | | 89.91% | | | 79.84% | | |
| NPV | 79.17% | | | 92.95% | | | 95.76% | | | 98.07% | | |
| Accuracy | 87.30% | | | 93.14% | | | 94.93% | | | 96.64% | | |

| | % of pop. | | % of pop. | | % of pop. | | % of pop. | |
|---|---|---|---|---|---|---|---|---|
| Test + | 27.8% | | Test + | 14.6% | Test + | 10.2% | Test + | 5.7% |
| Test − | 37.1% | | Test − | 55.0% | Test − | 61.0% | Test − | 67.1% |
| Equiv | 35.1% | | Equiv | 30.4% | Equiv | 28.8% | Equiv | 27.2% |

Furthermore, of the 122 test positives using the 35 ng/ml, 2 mg/ml, and 1000 ng/ml cut-offs, 21 of the test positives were false, giving a positive predictive value (PPV) of 82.8%. However, at a more typical prevalence of 30% fibrosis, the positive predictive value falls to about 58% (see Table 7). Thus, in a population with a typical prevalence, a positive result would not have sufficient predictive value to be useful as a diagnostic.

In order to increase the positive predictive value for at least a subset of the total patient population, samples positive by the primary analysis were further evaluated for positivity for the three markers using a second set of cut-off values which were higher than the first set. By evaluating those samples positive after a primary analysis at higher cutoffs, the severe fibrosis samples within this group can be determined to be positive with a relatively high predictive value. Those samples that test negative by the secondary evaluation are considered "indeterminate" in that their fibrosis status cannot be determined with good predictive value.

Table 7 shows performance of the α2-MG/HA/TIMP-1 panel assay with the dual optimization strategy. The primary cut-offs were set at 2.0 mg/ml, 35 ng/ml and 1000 ng/ml to achieve a relatively high sensitivity in the primary analysis. Any samples having all three of their α2-MG, HA and TIMP-1 levels above the assigned cut-off values were indicated to be positive. The 122 test positives obtained by the primary analysis were re-evaluated using 2.0 mg/ml, 60 ng/ml and 1575 ng/ml as the α2-MG, HA and TIMP-1 cut-offs and the criteria that the samples must have α2-MG, HA and TIMP-1 values above the assigned cut-off values to be positive.

Using the second set of cut-off values, 54 of the 122 patients were determined to be positive, only 1 of which was a false positive. The positive predictive value was 98.2% at 59.8% fibrosis prevalence, and was 93.9% at the more typical 30% fibrosis prevalence. In sum, of the 194 patients, 72 were classified as negative and 54 were classified as positive, while 68 samples had indeterminate results and could not be definitively classified. Furthermore, when the indeterminate samples are excluded, the three-marker assay has a positive predictive value of more than 93% and a negative predictive value of close to 93% in a typical population having a 30% fibrosis prevalence.

Table 8 shows a comparison of the performance of the α2-MG/HA/TIMP-1 three-marker panel with the six marker panel described in Poynard et al., *Lancet* 357:1069 (2001).

TABLE 8

COMPARISON OF PERFORMANCE OF α2-MG/HA/TIMP-1 PANEL WITH 6 MARKER PANEL OF POYNARD ET AL.

| | Prometheus | | | | Poynard et al. | | |
|---|---|---|---|---|---|---|---|
| | Biopsy | | | | Biopsy | | |
| | Fib + | Fib − | | | Fib + | Fib − | |
| Test + | 53 | 1 | 54 | Test + (>.08) | 45 | 5 | 50 |
| Test − | 15 | 57 | 72 | Test − (<0.20) | 13 | 106 | 119 |
| Equivocal | 48 | 20 | 68 | Equivocal | 80 | 90 | 170 |
| Total Pop. | 116 | 78 | 194 | Total Pop. | 138 | 201 | 339 |
| Prevalence | .05979 | | | Prevalence | 0.4071 | | |
| Sensitivity | 0.7794 | | | Sensitivity | 0.7759 | | |
| Specificity | 0.9828 | | | Specificity | 0.9550 | | |
| PPV | 0.9815 | | | PPV | 0.900 | | |
| NPV | 0.7917 | | | NPV | 0.8908 | | |
| Accuracy | 0.8730 | | | Accuracy | 0.8935 | | |
| % Equivoc | .03505 | 68/194 | | % Equivoc | .0515 | 170/339 | |
| False Pos | 1 | of 54 test + | 1.85% | False Pos | 5 | of 50 test + | 10.00% |
| False Neg | 15 | of 72 test − | 20.83% | False Neg | 13 | of 119 test − | 10.92% |
| Test + | 186 | 8 | 194 | Test + (>.08) | 133 | 15 | 147 |
| Test − | 53 | 433 | 486 | Test − (<0.20) | 38 | 313 | 351 |
| Equivocal | 168 | 152 | 320 | Equivocal | 236 | 265 | 501 |
| | 407 | 593 | 1000 | Total Pop. | 407 | 593 | 1000 |
| Prevalence | 0.4071 | | | Prevalence | 0.4071 | | |
| Sensitivity | 0.7794 | | | Sensitivity | 0.7759 | | |
| Specificity | 0.9828 | | | Specificity | 0.9550 | | |
| PPV | .9607 | | | PPV | 0.9000 | | |
| NPV | .8917 | | | NPV | 0.8907 | | |
| Accuracy | .09113 | | | Accuracy | 0.8935 | | |
| % test pos | 19.4% | | | % test pos | 14.7% | | |
| % test neg | 48.6% | | | % test neg | 35.1% | | |
| % Equivoc | 32.0 | | | % Equivoc | 50.1% | | |
| False Pos | 8 | of 194 test + | 3.93% | False Pos | 15 | of 147 test + | 10.00% |
| False Neg | 53 | of 486 test − | 10.83% | False Neg | 38 | of 35 test − | 10.93% |

\* alpha2-macroglobulin, alpha2-globulin, total bilirubin, gama-globulin, apo A1 and GGT These results indicate that the α2-MG/HA/TIMP-1 three-marker panel can be useful in differentiating F0–F1 fibrosis from F2–F4 fibrosis with very good accuracy. These results further indicate that a combination fibrosis marker assay can be useful in determining the fibrosis status of a portion of the patients tested with very good accuracy, while the remaining patients are candidates for biopsy.

EXAMPLE III

Assays for α2-Macroglobulin, Hyaluronic Acid and Tissue Inhibitor of Metalloproteinases-1

A. Quantitation of Human α2-Macroglobulin (α2-MG)

Serum levels of human α2-macroglobulin were quantitated using the Beckman Array® 360 System as follows to determine α2-MG levels in the range of 0.75–270 mg/ml.

The Beckman Array® 360 system was used for determination of α2-MG concentrations. This system utilizes a nephelometer which measures the rate of light-scatter formation resulting from an immunoprecipitation reaction between α2-MG antigen in a sample with antibody to human α2-MG. After passing a beam of light through the solution in a flow cell, the intensity of light scattered by the formed macromolecular particles of insoluble complexes suspended in solution is detected and measured by the nephelometer. The increase in light scatter resulting from the antigen-antibody reaction is converted to a peak rate signal proportional to the α2-MG concentration in the sample. The resulting formation of complexes and the consequent change in the intensity of scattered light occurs at a rate that increases gradually at first, then rapidly, and finally proceeds through a peak rate of change for the component being analyzed.

Serum samples were drawn from fasting individuals and generally physically separated from cells within 2 hours from the time of collection as set forth in NCCLS publication H 18-A. Samples not assayed within 72 hours were stored frozen at −15□C to −20□C. Frozen samples were at most thawed one time. Grossly hemolyzed, highly lipemic or turbid specimens were rejected for further analysis.

Reagents were removed from storage at 4□C and used immediately. Buffers and Diluents were mixed thoroughly by inversion prior to being added to the instrument. Set-up, priming and calibration were performed according to the manufacturer's instructions with samples diluted 1:36. Relatively concentrated samples such as undiluted samples or 1:6 dilutions were generally avoided. Grossly lipemic sample were diluted 1:2 with diluent before assaying. Dust particles or other particulate matter, which can result in extraneous light-scattering signals, in the reaction solution were avoided. Prior to assaying samples, any air bubbles or foam in the sample cups and reagent bottle were removed by using a disposable transfer pipette or pipette tip to aspirate the bubbles. DTT was avoided in the work area.

Samples were analyzed for α2-MG concentration as follows. The Reagent Wheel (left wheel) on the instrument was loaded with AMG antiserum in space #2. Dilution segments were loaded with 150 μL of control or sample in the wells on the larger side of the fan shaped segments. Segments and initial dilution control/sample cups were marked for identification. Bubbles were avoided while controls and serum samples were loaded.

Vigil™ Protein Control Levels 1 and 3 (3 drops) was placed in cups 1 and 3, respectively. Biorad Liquichek™ Immunology Control Level 2 (150 μL) was placed in cup 2. Patient samples (150 μL) were added to sequential cups. Segments were placed on right wheel beginning at position #1. Evaporation covers were placed over Reagent and Sample Wheels.

On the Master Screen menu, the RESULTS RECALL (F3) was selected before (F4) CLR CUR RUN. After returning to the MASTER SCREEN, the SAMPLE PROGRAM (F1) was selected. ENTER was selected when Reagent wheel #1 appeared and at each cup number. The control ID or sample Acc.# was entered. Test "2" was selected, and SAVE CUP (F1) was selected for each cup. START was selected to begin the analysis. At the end of the run, (Y) was selected in response to CLEAR CURRENT RUN & START NEXT RUN.

Results were reported by the Beckman Array® 360 in mg/dl using whole numbers in the Pros System. Samples were diluted routinely by the instrument 1:36. Samples greater than 750 mg/dl were assayed at a 1:216 dilution by the instrument. Samples having a concentration less than 75 mg/dl at a 1:36 dilution are reported as <75 mg/dl. At initial dilutions the Beckman analytical range was 75–750 mg/dl, while the extended range was 75–27,000 mg/dl. The range for normal individuals as verified at Prometheus Laboratories was 103–274 mg/dl.

Quality control was performed as follows. Three levels of controls were used: low, medium and high. Controls were within 2 standard deviations, except that runs were accepted with two controls within 2 standard deviations and the third control between 2 and 3 standard deviations. The controls used were Beckman Vigil I and III and Biorad Level II. Controls were assayed with each sample run.

The assay is calibrated every 14 days, and also when changes in reagent lots occur or when a major change has occurred in the instrument. Linearity is confirmed every 6 months with appropriate linearity material. This is done to ensure consistent performance over time and to comply with State and National standards.

Assay calibration verification is performed every 6 months to ensure consistency over time. A minimum of five verification samples including minimum, mid-point, and maximum concentrations are evaluated every 6 months. The coefficient of variation (% CV) of the verification sample results must be less than 15% in order to report out patient sample results.

B. Quantitation of Hyaluronic Acid (HA)

Serum levels of HA were determined using the Hyaluronic Acid (HA) Quantitative test kit (Catalog #029001) from Corgenix essentially as follows.

Serum samples were stored at −70° C. Multiple freeze/thaw cycles were avoided, with a maximum of 4 freeze/thaw cycles per sample. The kits were stored at 2–8° C.

Prior to use, the kit and patient samples were equilibrated to room temperature (18–28° C.). The pouch of coated strips also was equilibrated to room temperature before opening. Wash solution (0.01 M PBS, pH 7.35+/−0.1) was prepared by diluting the 33× PBS wash concentrate with distilled water and adjusting the pH of the final solution to pH 7.35+/−0.1.

All blanks, standards, controls and samples were assayed in duplicate. A water blank for calibration of the spectrophotometer was included with each plate and remained empty until addition of 200 μl water immediately prior to reading. Reaction buffer without serum sample was used-for the reagent blank, which represented the 0 ng/ml HA reference solution, and was treated the same as patient samples and reference solutions in subsequent assay steps. Three known patient samples (low, middle and high) were run with each assay. In addition, 50 ng/ml HA, 100 ng/ml HA, 200 ng/ml HA, 500 ng/ml HA and 800 ng/ml HA reference solutions supplied with each kit were assayed as described further below.

HA reference solutions and patient samples were diluted 1:11 by addition of 25 µl reference solution or sample to 250 µl of reaction buffer and mixed by gentle vortexing. The diluted reference, samples and controls were added (100 µl) to each well. The water blank remained empty. The plate was covered and incubated for 60 minutes at room temperature. After the incubation was complete, the contents of the wells were removed by aspiration. Plates were washed four times with 1× wash solution while avoiding the plates drying out between washes. The plate was blotted vigorously on paper towels to remove residual buffer after the last wash.

HRP-conjugated HA binding protein solution (100 µl) was added to all wells except the water blank before covering the plate and incubating for 30 minutes at room temperature. After the incubation was complete, the plate was washed four times as described above. Substrate solution (100 µl 3,3',5,5'-tetramethylbenzidine and hydrogen peroxide, stabilized) was then added to each well except for the water blank. The covered plate was then incubated for 30 minutes at room temperature. The plate was kept in the dark.

The $OD_{650}$ of the 800 ng/ml HA standard was determined. For an OD less than 0.500, the substrate incubation was continued and the OD monitored to determine if the OD had reached 0.500. For an OD greater than 0.500 or after one hour of substrate incubation even if the OD had not reached 0.500, the reactions were terminated by addition of 100 µl of Stopping Solution (0.36 N sulfuric acid) to each well except the water blank. The stop solution was added in the same order and at approximately the same rate as addition of the substrate solution. Before reading the optical densities, 200 µl distilled water was added to the water blank. The OD of each well was read at 450 nm (650 nm reference) within one hour after "zeroing" the plate reader against the water blank.

The following criteria were used to determine if the assay was reliable. The mean OD value of the reagent blank (zero standard) was less than 0.10. Readings greater than 0.10 were considered indicative of possible substrate or reagent contamination, and results were not reported under these conditions. The mean OD value of the 500 ng/ml HA reference was 0.800 or greater. Controls for the three known patient samples were within the following ranges: Low control: 78.6 to 117.2 ng/ml. Mid control: 148.5 to 214.1 ng/ml. High control: 297.8 to 460.7 ng/ml. Samples with HA concentrations greater than 800 ng/ml were further diluted and assayed a second time to obtain a more accurate result.

The known patient controls and samples were determined from a standard 4-parameter curve generated using Softmax and reported in ng/ml. The patient values were not reported if the concentration exceeded the concentration of the highest standard. For patient values greater than the concentration of the highest standard at a 1:11 dilution, samples were assayed at a 1:55 dilution and, if necessary, at higher dilution.

The HA ELISA assay is evaluated every six months to ensure consistent performance over time. A minimum of five samples with previously known HA values are evaluated in a blinded fashion to the operator. For the assay performance to be acceptable, results for negative samples must be negative, and results for positive samples must be positive and yield results within 15% of the previously obtained values. If greater than 20% of the validation samples fail the performance criteria, troubleshooting is implemented, and the assay is not used to report patient data until acceptable assay performance are reestablished.

C. Quantitation of Tissue Inhibitor of Metalloproteinases-1 (TIMP-1)

Serum levels of TIMP-1 were determined using the Biotrak™ test kit (Catalog# RPN2611) from Amersham Pharmacia Biotech (Piscataway, N.J.) essentially as follows.

Kit contents were thawed and equilibrated to 20–25° C. Serum samples were stored frozen at −70° C. Repeated freeze-thaw cycles of the samples were minimized, with a maximum of six freeze-thaw cycles.

Assay reagents were prepared as follows and stored at 2–8° C. for at most 7 days. Assay buffer 1 (0.1 M phosphate buffer, pH 7.5, with 0.9% (w/v) sodium chloride, 0.1% (w/v) BSA and 0.1% Tween-20) was prepared by adding distilled water to the assay buffer concentrate and adjusting the final volume to 100 ml.

Anti-TIMP-1 horseradish peroxidase conjugate was prepared in assay buffer 1 essentially as follows. To the stock bottle containing lyophilized conjugate, 11 ml diluted assay buffer 1 was added; the contents were mixed gently until completely dissolved while avoiding vigorous agitation and foaming. Wash buffer (0.1 M phosphate buffer, pH 7.5, containing 0.05% Tween-20) was prepared by adding distilled water to the wash buffer concentrate and bringing the final volume to 500 ml, followed by thorough mixing.

The 100 ng/ml TIMP-1 stock solution was prepared as follows and stored at 2–8° C. The lyophilized TIMP-1 standard was reconstituted in 0.1 M phosphate buffer, pH 7.5, containing 0.9% (w/v) sodium chloride, 0.1% (w/v) bovine serum albumin and 0.1% Tween-20 to make a standard TIMP-1 stock solution of 100 ng/ml. The contents were mixed gently until completely dissolved without vigorous agitation or foaming. Additional standards (1.565, 3.13, 6.25, 12.5, 25 and 50 ng/ml) for a standard curve were prepared fresh before each assay by two-fold serial dilution of the 100 ng/ml stock solution into assay buffer 1 in 1.2 ml dilution tubes. A zero standard (blank) was also prepared.

The pouch containing the microtiter plate was opened after equilibration to room temperature. All samples and standards were assayed in duplicate, and standards for a standard curve were present on each plate. On each plate, seven standards, two controls and a maximum of different 39 samples were present in duplicate.

Samples were diluted 1:120 in tubes by mixing 595 µl assay buffer 1 with 5 µl serum. The dilutions were mixed by vortexing. Using a multichannel pipettor, 100 µl of blank, standards and diluted samples were added to individual wells on a microtiter plate. The plate was covered with the lid provided and incubated at room temperature for exactly two hours. Following the two hour incubation, the contents of the wells were aspirated, and each well was washed four times with wash buffer, with complete filling and aspiration of the wells after each wash. After the final wash, the plates were blotted on paper towels to remove residual wash buffer.

Peroxidase conjugate (100 µl) was added to each well using a multichannel pipettor, and the covered plate incubated at room temperature for exactly two hours. After the incubation, the wells were aspirated and washed as before. Immediately upon conclusion of the incubation, 100 µl of room temperature equilibrated TMB substrate (3,3',5,5'-tetramethylbenzidine/ hydrogen peroxide in 20% (v/v) dimethylformamide) was added to each well. The plates were covered and incubated for exactly 30 minutes at room temperature. In some cases, the reactions were monitored at 630 nm. The reactions were stopped by addition of 100 ul 1 M sulfuric acid to all wells. Absorbance was determined at 450 nm within 30 minutes.

Control and patient samples values were determined using a standard curve (4-parameter curve fit) generated using Softmax. Concentration values from the standard curve were multiplied by the dilution factor (120) to obtain actual concentrations, reported in ng/ml. Quality of the assay was confirmed using known serum samples. The low control was in the range of 668.1 to 979.9 ng/ml. The high control was in the range of 2677.9 to 3300.2 ng/ml. Patient values generally did not exceed the concentration in ng/ml of the highest standard. Where the patient value was greater than the concentration of the highest standard at a 1:120 dilution, the result was reported as greater than 120 times the concentration of the highest standard.

The TIMP-1 ELISA assay is validated every six months to ensure consistent performance over time. A minimum of five samples with previously known values are evaluated in a blinded fashion to the operator. Results for negative samples must be negative. Results for positive samples must be positive and must yield results within 15% of the previously obtained values. Where greater than 20% of the validation samples fail the performance criteria, troubleshooting is implemented. Further patient data are not reported until acceptable assay performance is reestablished.

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention. Accordingly, the invention is limited only by the claims.

We claim:

1. A method of diagnosing the presence or severity of liver fibrosis in an individual, comprising the steps of:
   (a) detecting α2-macroglobulin (α2-MG) in a sample from said individual;
   (b) detecting hyaluronic acid (HA) in a sample from said individual;
   (c) detecting tissue inhibitor of metalloproteinases-1 (TIMP-1) in a sample from said individual; and
   (d) diagnosing the presence or severity of liver fibrosis in said individual based on the presence or level of α2-MG, HA and TIMP-1.

2. The method of claim 1, comprising detecting at most three markers of fibrosis.

3. The method of claim 1, further comprising detecting in a sample from said individual at least one marker selected from the group consisting of: PIIINP, laminin, tenascin, collagen type IV, collagen type VI, YKL-40, MMP-3, MMP-2, MMP-9/TIMP-1 complex, sFas ligand, TGF-β1, IL-10, apoA1, apoA2, and apoB.

4. The method of claim 3, wherein said marker is YKL-40.

5. The method of claim 1, further comprising detecting in a sample from said individual two or more markers selected from the group consisting of PIIINP, laminin, tenascin, collagen type IV, collagen type VI, YKL-40, MMP-3, MMP-2, MMP-9/TIMP-1 complex, sFas ligand, TGF-β1, IL-10, apoA1, apoA2 and apoB.

6. The method of claim 1, wherein said individual has viral hepatitis.

7. The method of claim 6, wherein said individual is infected with hepatitis C virus.

8. The method of claim 6, wherein said individual is infected with hepatitis B virus.

9. The method of claim 1, wherein said individual has autoimmune liver disease.

10. The method of claim 1, wherein said individual has alcoholic liver disease.

11. The method of claim 1, wherein said individual has a fatty liver disease.

12. The method of claim 1, wherein said individual has drug-induced liver disease.

13. The method of claim 1, wherein step (a) comprises determining the level of α2-MG protein in said sample.

14. The method of claim 13, wherein the level of α2-MG protein is determined using one or more anti-α2-MG antibodies.

15. The method of claim 1, wherein step (a) comprises determining a level of α2-MG activity.

16. The method of claim 1, wherein step (b) comprises determining the level of HA in said sample.

17. The method of claim 16, wherein the level of HA is determined using one or more HA-binding proteins.

18. The method of claim 16, wherein the level of HA is determined using one or more anti-HA antibodies.

19. The method of claim 1, wherein step (c) comprises determining the level of TIMP-1 protein in said sample.

20. The method of claim 19, wherein the level of TIMP-1 protein is determined using one or more anti-TIMP-1 antibodies.

21. The method of claim 1, wherein step (c) comprises determining a level of TIMP-1 activity.

22. The method of claim 1,
wherein step (a) comprises determining the level of α2-MG protein,
wherein step (b) comprises determining the level of HA, and
wherein step (c) comprises determining the level of TIMP-1 protein.

23. The method of claim 22, wherein the level of α2-MG protein, HA and TIMP-1 protein each is determined using an enzyme-linked assay.

24. The method of claim 1, wherein a single sample is obtained from said individual.

25. The method of claim 24, wherein said sample is selected from the group consisting of blood, serum, plasma, urine, saliva and liver tissue.

26. The method of claim 25, wherein said sample is a serum sample.

27. The method of claim 1, comprising differentiating F0–F1 fibrosis from F2–F4 fibrosis.

28. A method of differentiating F0–F1 fibrosis from F2–F4 fibrosis in an individual, comprising the steps of:
(a) contacting an appropriate dilution of a sample from said individual with anti-α2-MG antibody under conditions suitable to form a first complex of α2-MG and anti-α2-MG antibody;
(b) washing said first complex to remove unbound molecules;
(c) determining the amount of α2-MG-containing first complex;
(d) contacting an appropriate dilution of a sample from said individual with a HA-binding protein (HABP) under conditions suitable to form a second complex of HA and HABP;
(e) washing said second complex to remove unbound molecules;
(f) determining the amount of HA-containing second complex;
(g) contacting an appropriate dilution of a sample from said individual with anti-TIMP-1 antibody under conditions suitable to form a third complex of TIMP-1 and anti-TIMP-1 antibody;
(h) washing said third complex to remove unbound molecules;
(i) determining the amount of TIMP-1-containing third complex; and
(j) differentiating F0–F1 fibrosis from F2–F4 fibrosis in said individual based on the amounts of α2-MG, HA and TIMP-1-containing complexes.

29. A method of monitoring the efficacy of anti-fibrotic therapy in a patient, comprising the steps of:
(a) detecting α2-macroglobulin (α2-MG) in a sample from a patient administered an anti-fibrotic therapy;
(b) detecting hyaluronic acid (HA) in a sample from said patient;
(c) detecting tissue inhibitor of metalloproteinases-1 (TIMP-1) in a sample from said patient; and
(d) determining the presence or severity of liver fibrosis in said patient based on the presence or level of α2-MG, HA and TIMP-1, thereby monitoring the efficacy of anti-fibrotic therapy.

30. The method of claim 29, further comprising comparing the presence or severity of liver fibrosis determined in step (d) to the presence or severity of liver fibrosis in said patient at an earlier time.

31. The method of claim 29, comprising detecting at most three markers of fibrosis.

32. The method of claim 29, further comprising detecting in a sample from said patient at least one marker selected from the group consisting of: PIIINP, laminin, tenascin, collagen type IV, collagen type VI, YKL-40, MMP-3, MMP-2, MMP-9/TIMP-1 complex, sFas ligand, TGF-β1, IL-10, apoA1, apoA2, and apoB.

33. The method of claim 29, wherein step (a) comprises determining the level of α2-MG protein in said sample.

34. The method of claim 33, wherein the level of .alpha.2-MG protein is determined using one or more anti-α2-MG antibodies.

35. The method of claim 29, wherein step (b) comprises determining the level of HA in said sample.

36. The method of claim 35, wherein the level of HA is determined using one or more HA-binding proteins.

37. The method of claim 29, wherein step (c) comprises determining the level of TIMP-1 protein in said sample.

38. The method of claim 37, wherein the level of TIMP-1 protein is determined using one or more anti-TIMP-1 antibodies.

39. A method of differentiating F0–F1 fibrosis from F2–F4 fibrosis in an individual, comprising the steps of:
(a) determining an α2-MG level in a sample from said individual;
(b) determining a HA level in a sample from said individual;
(c) determining a TIMP-1 level in a sample from said individual; and
(d) diagnosing said individual as having F0–F1 fibrosis when said α2-MG level is below an α2-MG cut-off value X1, said HA level is below a HA cut-off value Y1 or said TIMP-1 level is below a TIMP-1 cut-off value Z1, diagnosing said individual as having F2–F4 fibrosis when said α2-MG level is above an α2-MG cut-off value X2, said HA level is above a HA cut-off value Y2 and said TIMP-1 level is above a TIMP-1 cut-off value Z2, and diagnosing said individual as having an indeterminate status when said α2-MG level is above X1, said HA level is above Y1, and said TIMP-1 level is above Z1 but said α2-MG level is below X2, said HA level is below Y2 or said TIMP-1 level is below Z2.

40. The method of claim 39, wherein said individual has a disorder selected from the group consisting of viral hepatitis, autoimmune liver disease, alcoholic liver disease, fatty liver disease and drug-induced liver disease.

41. The method of claim 40, wherein said individual is infected with hepatitis C virus.

42. The method of claim 39, wherein said samples are independently selected from the group consisting of blood, serum, plasma, urine, saliva and liver tissue.

43. The method of claim 42, wherein said α2-MG level, HA level and TIMP-1 level each is determined in a serum sample.

44. The method of claim 43,
wherein X1 is a value between 1.8 and 2.2 mg/ml;
wherein Y1 is a value between 31 and 39 ng/ml;
wherein Z1 is a value between 900 and 1100 ng/ml;
wherein X2 is a value between 1.8 and 2.2 mg/ml;
wherein Y2 is a value between 54 and 66 ng/ml; and
wherein Z2 is a value between 1415 and 1735 ng/ml.

45. The method of claim 44,
wherein X1=2.0 mg/ml;
wherein Y1=35 ng/ml;
wherein Z1 =1000 ng/ml;
wherein X2=2.0 mg/ml;
wherein Y2=60 ng/ml; and
wherein Z2=1575 ng/ml.

46. The method of claim 44,
wherein X1=2.0 mg/ml;
wherein Y1=37 ng/ml;
wherein Z1=1100 ng/ml;
wherein X2=2.0 mg/ml;
wherein Y2=60 ng/ml; and
wherein Z2=1575 ng/ml.

47. The method of claim 39, wherein in a population having up to 30% liver fibrosis prevalence, X1, Y1, Z1, X2, Y2, and Z2 are independently selected to differentiate F0–F1 fibrosis from F2–F4 fibrosis in said individual with at least about 80% accuracy in at least 65% of the population assayed.

48. The method of claim 39, wherein in a population having up to 30% liver fibrosis prevalence, X1, Y1, Z1, X2, Y2, and Z2 are independently selected to differentiate F0–F1 fibrosis from F2–F4 fibrosis in said individual with at least about 90% accuracy in at least 65% of the population assayed.

49. The method of claim 39, wherein in a population having up to 30% liver fibrosis prevalence, X1, Y1, Z1, X2, Y2, and Z2 are independently selected to differentiate F0–F1 fibrosis from F2–F4 fibrosis in said individual with a positive predictive value of at least 90% or a negative predictive value of at least 90% in at least 65% of the population assayed.

50. The method of claim 39, wherein in a population having up to 10% liver fibrosis prevalence, X1, Y1, Z1, X2, Y2, and Z2 are independently selected to differentiate F0–F1 fibrosis from F2–F4 fibrosis in said individual with at least about 90% accuracy in at least 70% of the population assayed.

51. A method of diagnosing the presence or severity of liver fibrosis in an individual, comprising the steps of:
(a) comparing a level of a first fibrotic marker α2-MG in said individual to a cut-off value X1 to determine whether said individual is positive for α2-MG;
(b) comparing a level of a second fibrotic marker HA in said individual to a cut-off value Y1 to determine whether said individual is positive for HA;
(c) comparing a level of a third fibrotic marker TIMP-1 in said individual to a cut-off value Z1 to determine whether said individual is positive for TIMP-1; and
(d) diagnosing the presence or severity of liver fibrosis in said individual based on positivity or negativity for α2-MG, HA, and TIMP-1.
wherein in a population having about 40% liver fibrosis prevalence, X1, Y1 and Z1 are independently selected to diagnose the presence or severity of liver fibrosis in said individual with more than 91% accuracy in about 70% of the population assayed.

52. The method of claim 51, wherein the levels of at least three fibrotic markers are compared.

53. The method of claim 51, wherein the levels of three fibrotic markers are compared.

54. The method of claim 51, wherein the levels of at least four fibrotic markers are compared.

55. The method of claim 51, wherein the levels of at least five fibrotic markers are compared.

56. The method of claim 51, wherein said diagnosis differentiates F0–F1 fibrosis from F2–F4 fibrosis.

57. A method of diagnosing the presence or severity of liver fibrosis in an individual, comprising the steps of:
(a) comparing a level of a first fibrotic marker α2-MG in said individual to a cut-off value X1 to determine whether said individual is positive for α2-MG;
(b) comparing a level of a second fibrotic marker HA in said individual to a cut-off value Y1 to determine whether said individual is positive for HA;
(c) comparing a level of a third fibrotic marker TIMP-1 in said individual to a cut-off value Z1 to determine whether said individual is positive for TIMP-1; and
(d) diagnosing the presence or severity of liver fibrosis in said individual based on positivity or negativity for α2-MG, HA, and TIMP-1,
wherein said cut-off values X1, Y1, and Z1 are independently selected to achieve an optimized clinical parameter selected from the group consisting of sensitivity, specificity, negative predictive value, positive predictive value, and accuracy.

58. The method of claim 57, wherein said cut-off values are optimized using design of experiments (DOE) analysis.

59. The method of claim 57, wherein the levels of at least three fibrotic markers are compared.

60. The method of claim 57, wherein the levels of three fibrotic markers are compared.

61. The method of claim 57, wherein said diagnosis differentiates F0–F1 fibrosis from F2–F4 fibrosis.

62. A method of diagnosing the presence or severity of liver fibrosis in an individual, comprising the steps of:
(a) comparing a level of a first fibrotic marker α2-MG in said individual to a cut-off value X1 to determine whether said individual is positive for α2-MG, wherein said individual is positive for α2-MG when said level of α2-MG is above X1;

(b) comparing a level of a second fibrotic marker HA in said individual to a cut-off value Y1 to determine whether said individual is positive for HA, wherein said individual is positive for HA when said level of HA is above Y1;

(c) comparing a level of a third fibrotic marker TIMP-1 in said individual to a cut-off value Z1 to determine whether said individual is positive for TIMP-1, wherein said individual is positive for TIMP-1 when said level of TIMP-1 is above Z1, wherein any individual positive for $\alpha 2$-MG, HA, and TIMP-1 as compared to X1, Y1, and Z1, respectively, is further evaluated for positivity for $\alpha 2$-MG, HA, and TIMP-1 using a second set of cut-off values X2, Y2, and Z2 comprising:

(d) comparing the level of $\alpha 2$-MG in said individual to X2, wherein said individual is positive for $\alpha 2$-MG when said level of $\alpha 2$-MG is above X2;

(e) comparing the level of HA in said individual to Y2, wherein said individual is positive for HA when said level of HA is above Y2;

(f) comparing the level of TIMP-1 in said individual to Z2, wherein said individual is positive for TIMP-1 when said level of TIMP-1 is above Z2; and (g) diagnosing the presence or severity of liver fibrosis in said individual based on positivity or negativity for $\alpha 2$-MG, HA, and TIMP-1, wherein said cut-off values X2, Y2, and Z2 are greater than or equal to X1, Y1, and Z1, respectively, wherein said individual is diagnosed as having liver fibrosis when said individual is positive for $\alpha 2$-MG, HA, and TIMP-1 as compared to X2, Y2, and Z2, respectively, and wherein said individual is diagnosed as having an indeterminate status when said individual is negative for $\alpha 2$-MG, HA, or TIMP-1 as compared to X2, Y2, and Z2, respectively.

63. The method of claim 62, wherein said cut-off values are optimized using design of experiments (DOE) analysis.

* * * * *

SEQUENCE LISTING

<160> NUMBER OF SEQ ID NOS: 4

<210> SEQ ID NO 1
<211> LENGTH: 2041
<212> TYPE: DNA
<213> ORGANISM: Homo sapiens
<220> FEATURE:
<221> NAME/KEY: CDS
<222> LOCATION: (1)...(1932)

<400> SEQUENCE: 1

```
ccc gcc ttc cta gct gtc cca gtg gag aag gaa caa gcg cct cac tgc      48
Pro Ala Phe Leu Ala Val Pro Val Glu Lys Glu Gln Ala Pro His Cys
 1               5                  10                  15 atc tgt gca aac ggg cgg caa act gtg tcc tgg gca gta acc cca aag      96
Ile Cys Ala Asn Gly Arg Gln Thr Val Ser Trp Ala Val Thr Pro Lys
             20                  25                  30 tca tta gga aat gtg aat ttc act gtg agc gca gag gca cta gag tct     144
Ser Leu Gly Asn Val Asn Phe Thr Val Ser Ala Glu Ala Leu Glu Ser
         35                  40                  45 caa gag ctg tgt ggg act gag gtg cct tca gtt cct gaa cac gga agg     192
Gln Glu Leu Cys Gly Thr Glu Val Pro Ser Val Pro Glu His Gly Arg
     50                  55                  60 aaa gac aca gtc atc aag cct ctg ttg gtt gaa cct gaa gga cta gag     240
Lys Asp Thr Val Ile Lys Pro Leu Leu Val Glu Pro Glu Gly Leu Glu
 65                  70                  75                  80 aag gaa aca aca ttc aac tcc cta ctt tgt cca tca ggt ggt gag gtt     288
Lys Glu Thr Thr Phe Asn Ser Leu Leu Cys Pro Ser Gly Gly Glu Val
                 85                  90                  95 tct gaa gaa tta tcc ctg aaa ctg cca cca aat gtg gta gaa gaa tct     336
Ser Glu Glu Leu Ser Leu Lys Leu Pro Pro Asn Val Val Glu Glu Ser
            100                 105                 110 gcc cga gct tct gtc tca gtt ttg gga gac ata tta ggc tct gcc atg     384
Ala Arg Ala Ser Val Ser Val Leu Gly Asp Ile Leu Gly Ser Ala Met
        115                 120                 125 caa aac aca caa aat ctt ctc cag atg ccc tat ggc tgt gga gag cag     432
Gln Asn Thr Gln Asn Leu Leu Gln Met Pro Tyr Gly Cys Gly Glu Gln
    130                 135                 140 aat atg gtc ctc ttt gct cct aac atc tat gta ctg gat tat cta aat     480
Asn Met Val Leu Phe Ala Pro Asn Ile Tyr Val Leu Asp Tyr Leu Asn
145                 150                 155                 160
```

```
                                                    -continued gaa aca cag cag ctt act cca gag atc aag tcc aag gcc att ggc tat        528
Glu Thr Gln Gln Leu Thr Pro Glu Ile Lys Ser Lys Ala Ile Gly Tyr
            165                 170                 175 ctc aac act ggt tac cag aga cag ttg aac tac aaa cac tat gat ggc        576
Leu Asn Thr Gly Tyr Gln Arg Gln Leu Asn Tyr Lys His Tyr Asp Gly
        180                 185                 190 tcc tac agc acc ttt ggg gag cga tat ggc agg aac cag ggc aac acc        624
Ser Tyr Ser Thr Phe Gly Glu Arg Tyr Gly Arg Asn Gln Gly Asn Thr
    195                 200                 205 tgg ctc aca gcc ttt gtt ctg aag act ttt gcc caa gct cga gcc tac        672
Trp Leu Thr Ala Phe Val Leu Lys Thr Phe Ala Gln Ala Arg Ala Tyr
210                 215                 220 atc ttc atc gat gaa gca cac att acc caa gcc ctc ata tgg ctc tcc        720
Ile Phe Ile Asp Glu Ala His Ile Thr Gln Ala Leu Ile Trp Leu Ser
225                 230                 235                 240 cag agg cag aag gac aat ggc tgt ttc agg agc tct ggg tca ctg ctc        768
Gln Arg Gln Lys Asp Asn Gly Cys Phe Arg Ser Ser Gly Ser Leu Leu
            245                 250                 255 aac aat gcc ata aag gga gga gta gaa gat gaa gtg acc ctc tcc gcc        816
Asn Asn Ala Ile Lys Gly Gly Val Glu Asp Glu Val Thr Leu Ser Ala
        260                 265                 270 tat atc acc atc gcc ctt ctg gag att cct ctc aca gtc act cac cct        864
Tyr Ile Thr Ile Ala Leu Leu Glu Ile Pro Leu Thr Val Thr His Pro
    275                 280                 285 gtt gtc cgc aat gcc ctg ttt tgc ctg gag tca gcc tgg aag aca gca        912
Val Val Arg Asn Ala Leu Phe Cys Leu Glu Ser Ala Trp Lys Thr Ala
290                 295                 300 caa gaa ggg gac cat ggc agc cat gta tat acc aaa gac ctg ctg gcc        960
Gln Glu Gly Asp His Gly Ser His Val Tyr Thr Lys Asp Leu Leu Ala
305                 310                 315                 320 tat gct ttt gcc ctg gca ggt aac cag gac aag agg aag gaa gta ctc       1008
Tyr Ala Phe Ala Leu Ala Gly Asn Gln Asp Lys Arg Lys Glu Val Leu
            325                 330                 335 aag tca ctt aat gag gaa gct gtg aag aaa gac aac tct gtc cat tgg       1056
Lys Ser Leu Asn Glu Glu Ala Val Lys Lys Asp Asn Ser Val His Trp
        340                 345                 350 gag cgc cct cag aaa ccc aag gca cca gtg ggg gat ttt tac gaa ccc       1104
Glu Arg Pro Gln Lys Pro Lys Ala Pro Val Gly Asp Phe Tyr Glu Pro
    355                 360                 365 cag gct ccc tct gct gag gtg gag atg aca tcc tat gtg ctc ctc gct       1152
Gln Ala Pro Ser Ala Glu Val Glu Met Thr Ser Tyr Val Leu Leu Ala
370                 375                 380 tat ctc acg gcc cag cca gcc cca acc tcg gag gac ctg acc tct gca       1200
Tyr Leu Thr Ala Gln Pro Ala Pro Thr Ser Glu Asp Leu Thr Ser Ala
385                 390                 395                 400 acc aac atc gtg aag tgg atc acg aag cag cag aat gcc cag ggc ggt       1248
Thr Asn Ile Val Lys Trp Ile Thr Lys Gln Gln Asn Ala Gln Gly Gly
            405                 410                 415 ttc tcc tcc acc cag gac aca gtg gtg gct ctc cat gct ctg tcc aaa       1296
Phe Ser Ser Thr Gln Asp Thr Val Val Ala Leu His Ala Leu Ser Lys
        420                 425                 430 tat gga gca gcc aca ttt acc agg act ggg aag gct gca cag gtg act       1344
Tyr Gly Ala Ala Thr Phe Thr Arg Thr Gly Lys Ala Ala Gln Val Thr
    435                 440                 445 atc cag tct tca ggg aca ttt tcc agc aaa ttc caa gtg gac aac aac       1392
Ile Gln Ser Ser Gly Thr Phe Ser Ser Lys Phe Gln Val Asp Asn Asn
450                 455                 460 aac cgc ctg tta ctg cag cag gtc tca ttg cca gag ctg cct ggg gaa       1440
Asn Arg Leu Leu Leu Gln Gln Val Ser Leu Pro Glu Leu Pro Gly Glu
465                 470                 475                 480
```

```
tac agc atg aaa gtg aca gga gaa gga tgt gtc tac ctc cag aca tcc      1488
Tyr Ser Met Lys Val Thr Gly Glu Gly Cys Val Tyr Leu Gln Thr Ser
                485                 490                 495 ttg aaa tac aat att ctc cca gaa aag gaa gag ttc ccc ttt gct tta      1536
Leu Lys Tyr Asn Ile Leu Pro Glu Lys Glu Glu Phe Pro Phe Ala Leu
            500                 505                 510 gga gtg cag act ctg cct caa act tgt gat gaa ccc aaa gcc cac acc      1584
Gly Val Gln Thr Leu Pro Gln Thr Cys Asp Glu Pro Lys Ala His Thr
        515                 520                 525 agc ttc caa atc tcc cta agt gtc agt tac aca ggg agc cgc tct gcc      1632
Ser Phe Gln Ile Ser Leu Ser Val Ser Tyr Thr Gly Ser Arg Ser Ala
    530                 535                 540 tcc aac atg gcg atc gtt gat gtg aag atg gtc tct ggc ttc att ccc      1680
Ser Asn Met Ala Ile Val Asp Val Lys Met Val Ser Gly Phe Ile Pro
545                 550                 555                 560 ctg aag cca aca gtg aaa atg ctt gaa aga tct aac cat gtg agc cgg      1728
Leu Lys Pro Thr Val Lys Met Leu Glu Arg Ser Asn His Val Ser Arg
                565                 570                 575 aca gaa gtc agc agc aac cat gtc ttg att tac ctt gat aag gtg tca      1776
Thr Glu Val Ser Ser Asn His Val Leu Ile Tyr Leu Asp Lys Val Ser
            580                 585                 590 aat cag aca ctg agc ttg ttc ttc acg gtt ctg caa gat gtc cca gta      1824
Asn Gln Thr Leu Ser Leu Phe Phe Thr Val Leu Gln Asp Val Pro Val
        595                 600                 605 aga gat ctg aaa cca gcc ata gtg aaa gtc tat gat tac tac gag acg      1872
Arg Asp Leu Lys Pro Ala Ile Val Lys Val Tyr Asp Tyr Tyr Glu Thr
    610                 615                 620 gat gag ttt gca att gct gag tac aat gct cct tgc agc aaa gat ctt      1920
Asp Glu Phe Ala Ile Ala Glu Tyr Asn Ala Pro Cys Ser Lys Asp Leu
625                 630                 635                 640 gga aat gct tga agaccacaag gctgaaaagt gctttgctgg agtcctgttc          1972
Gly Asn Ala * tcagagctcc acagaagaca cgtgtttttg tatctttaaa gacttgatga ataaacactt    2032
tttctggtc                                                            2041

<210> SEQ ID NO 2
<211> LENGTH: 643
<212> TYPE: PRT
<213> ORGANISM: Homo sapiens

<400> SEQUENCE: 2

Pro Ala Phe Leu Ala Val Pro Val Glu Lys Glu Gln Ala Pro His Cys
 1               5                  10                  15

Ile Cys Ala Asn Gly Arg Gln Thr Val Ser Trp Ala Val Thr Pro Lys
            20                  25                  30

Ser Leu Gly Asn Val Asn Phe Thr Val Ser Ala Glu Ala Leu Glu Ser
        35                  40                  45

Gln Glu Leu Cys Gly Thr Glu Val Pro Ser Val Pro Glu His Gly Arg
    50                  55                  60

Lys Asp Thr Val Ile Lys Pro Leu Leu Val Glu Pro Glu Gly Leu Glu
65                  70                  75                  80

Lys Glu Thr Thr Phe Asn Ser Leu Leu Cys Pro Ser Gly Gly Glu Val
                85                  90                  95

Ser Glu Glu Leu Ser Leu Lys Leu Pro Pro Asn Val Val Glu Glu Ser
            100                 105                 110

Ala Arg Ala Ser Val Ser Val Leu Gly Asp Ile Leu Gly Ser Ala Met
        115                 120                 125
```

```
Gln Asn Thr Gln Asn Leu Leu Gln Met Pro Tyr Gly Cys Gly Glu Gln
130                 135                 140

Asn Met Val Leu Phe Ala Pro Asn Ile Tyr Val Leu Asp Tyr Leu Asn
145                 150                 155                 160

Glu Thr Gln Gln Leu Thr Pro Glu Ile Lys Ser Lys Ala Ile Gly Tyr
                165                 170                 175

Leu Asn Thr Gly Tyr Gln Arg Gln Leu Asn Tyr Lys His Tyr Asp Gly
            180                 185                 190

Ser Tyr Ser Thr Phe Gly Glu Arg Tyr Gly Arg Asn Gln Gly Asn Thr
        195                 200                 205

Trp Leu Thr Ala Phe Val Leu Lys Thr Phe Ala Gln Ala Arg Ala Tyr
    210                 215                 220

Ile Phe Ile Asp Glu Ala His Ile Thr Gln Ala Leu Ile Trp Leu Ser
225                 230                 235                 240

Gln Arg Gln Lys Asp Asn Gly Cys Phe Arg Ser Ser Gly Ser Leu Leu
                245                 250                 255

Asn Asn Ala Ile Lys Gly Gly Val Glu Asp Glu Val Thr Leu Ser Ala
            260                 265                 270

Tyr Ile Thr Ile Ala Leu Leu Glu Ile Pro Leu Thr Val Thr His Pro
        275                 280                 285

Val Val Arg Asn Ala Leu Phe Cys Leu Glu Ser Ala Trp Lys Thr Ala
    290                 295                 300

Gln Glu Gly Asp His Gly Ser His Val Tyr Thr Lys Asp Leu Leu Ala
305                 310                 315                 320

Tyr Ala Phe Ala Leu Ala Gly Asn Gln Asp Lys Arg Lys Glu Val Leu
                325                 330                 335

Lys Ser Leu Asn Glu Glu Ala Val Lys Lys Asp Asn Ser Val His Trp
            340                 345                 350

Glu Arg Pro Gln Lys Pro Lys Ala Pro Val Gly Asp Phe Tyr Glu Pro
        355                 360                 365

Gln Ala Pro Ser Ala Glu Val Glu Met Thr Ser Tyr Val Leu Leu Ala
    370                 375                 380

Tyr Leu Thr Ala Gln Pro Ala Pro Thr Ser Glu Asp Leu Thr Ser Ala
385                 390                 395                 400

Thr Asn Ile Val Lys Trp Ile Thr Lys Gln Gln Asn Ala Gln Gly Gly
                405                 410                 415

Phe Ser Ser Thr Gln Asp Thr Val Val Ala Leu His Ala Leu Ser Lys
            420                 425                 430

Tyr Gly Ala Ala Thr Phe Thr Arg Thr Gly Lys Ala Ala Gln Val Thr
        435                 440                 445

Ile Gln Ser Ser Gly Thr Phe Ser Ser Lys Phe Gln Val Asp Asn Asn
    450                 455                 460

Asn Arg Leu Leu Leu Gln Gln Val Ser Leu Pro Glu Leu Pro Gly Glu
465                 470                 475                 480

Tyr Ser Met Lys Val Thr Gly Glu Gly Cys Val Tyr Leu Gln Thr Ser
                485                 490                 495

Leu Lys Tyr Asn Ile Leu Pro Glu Lys Glu Glu Phe Pro Phe Ala Leu
            500                 505                 510

Gly Val Gln Thr Leu Pro Gln Thr Cys Asp Glu Pro Lys Ala His Thr
        515                 520                 525

Ser Phe Gln Ile Ser Leu Ser Val Ser Tyr Thr Gly Ser Arg Ser Ala
    530                 535                 540
```

```
Ser Asn Met Ala Ile Val Asp Val Lys Met Val Ser Gly Phe Ile Pro
545                 550                 555                 560

Leu Lys Pro Thr Val Lys Met Leu Glu Arg Ser Asn His Val Ser Arg
                565                 570                 575

Thr Glu Val Ser Ser Asn His Val Leu Ile Tyr Leu Asp Lys Val Ser
            580                 585                 590

Asn Gln Thr Leu Ser Leu Phe Phe Thr Val Leu Gln Asp Val Pro Val
        595                 600                 605

Arg Asp Leu Lys Pro Ala Ile Val Lys Val Tyr Asp Tyr Tyr Glu Thr
    610                 615                 620

Asp Glu Phe Ala Ile Ala Glu Tyr Asn Ala Pro Cys Ser Lys Asp Leu
625                 630                 635                 640

Gly Asn Ala

<210> SEQ ID NO 3
<211> LENGTH: 782
<212> TYPE: DNA
<213> ORGANISM: Homo sapiens
<220> FEATURE:
<221> NAME/KEY: CDS
<222> LOCATION: (63)...(686)

<400> SEQUENCE: 3 agggccetta gcgtgccgca tcgccgagat ccagcgccca gagagacacc agagaaccca      60 cc atg gcc ccc ttt gag ccc ctg gct tct ggc atc ctg ttg ttg ctg       107
   Met Ala Pro Phe Glu Pro Leu Ala Ser Gly Ile Leu Leu Leu Leu
     1               5                  10                  15 tgg ctg ata gcc ccc agc agg gcc tgc acc tgt gtc cca ccc cac cca       155
Trp Leu Ile Ala Pro Ser Arg Ala Cys Thr Cys Val Pro Pro His Pro
                20                  25                  30 cag acg gcc ttc tgc aat tcc gac ctc gtc atc agg gcc aag ttc gtg       203
Gln Thr Ala Phe Cys Asn Ser Asp Leu Val Ile Arg Ala Lys Phe Val
            35                  40                  45 ggg aca cca gaa gtc aac cag acc acc tta tac cag cgt tat gag atc       251
Gly Thr Pro Glu Val Asn Gln Thr Thr Leu Tyr Gln Arg Tyr Glu Ile
        50                  55                  60 aag atg acc aag atg tat aaa ggg ttc caa gcc tta ggg gat gcc gct       299
Lys Met Thr Lys Met Tyr Lys Gly Phe Gln Ala Leu Gly Asp Ala Ala
 65                  70                  75 gac atc cgg ttc gtc tac acc ccc gcc atg gag agt gtc tgc gga tac       347
Asp Ile Arg Phe Val Tyr Thr Pro Ala Met Glu Ser Val Cys Gly Tyr
 80                  85                  90                  95 ttc cac agg tcc cac aac cgc agc gag gag ttt ctc att gct gga aaa       395
Phe His Arg Ser His Asn Arg Ser Glu Glu Phe Leu Ile Ala Gly Lys
                100                 105                 110 ctg cag gat gga ctc ttg cac atc act acc tgc agt ttc gtg gct ccc       443
Leu Gln Asp Gly Leu Leu His Ile Thr Thr Cys Ser Phe Val Ala Pro
            115                 120                 125 tgg aac agc ctg agc tta gct cag cgc cgg ggc ttc acc aag acc tac       491
Trp Asn Ser Leu Ser Leu Ala Gln Arg Arg Gly Phe Thr Lys Thr Tyr
        130                 135                 140 act gtt ggc tgt gag gaa tgc aca gtg ttt ccc tgt tta tcc atc ccc       539
Thr Val Gly Cys Glu Glu Cys Thr Val Phe Pro Cys Leu Ser Ile Pro
145                 150                 155 tgc aaa ctg cag agt ggc act cat tgc ttg tgg acg gac cag ctc ctc       587
Cys Lys Leu Gln Ser Gly Thr His Cys Leu Trp Thr Asp Gln Leu Leu
160                 165                 170                 175
```

-continued

```
caa ggc tct gaa aag ggc ttc cag tcc cgt cac ctt gcc tgc ctg cct      635
Gln Gly Ser Glu Lys Gly Phe Gln Ser Arg His Leu Ala Cys Leu Pro
            180                 185                 190 cgg gag cca ggg ctg tgc acc tgg cag tcc ctg cgg tcc cag ata gcc      683
Arg Glu Pro Gly Leu Cys Thr Trp Gln Ser Leu Arg Ser Gln Ile Ala
            195                 200                 205 tga atcctgcccg gagtggaact gaagcctgca cagtgtccac cctgttccca           736
* ctcccatctt tcttccggac aatgaaataa agagttacca cccagc                   782

<210> SEQ ID NO 4
<211> LENGTH: 207
<212> TYPE: PRT
<213> ORGANISM: Homo sapiens

<400> SEQUENCE: 4

Met Ala Pro Phe Glu Pro Leu Ala Ser Gly Ile Leu Leu Leu Leu Trp
 1               5                  10                  15

Leu Ile Ala Pro Ser Arg Ala Cys Thr Cys Val Pro Pro His Pro Gln
            20                  25                  30

Thr Ala Phe Cys Asn Ser Asp Leu Val Ile Arg Ala Lys Phe Val Gly
        35                  40                  45

Thr Pro Glu Val Asn Gln Thr Thr Leu Tyr Gln Arg Tyr Glu Ile Lys
    50                  55                  60

Met Thr Lys Met Tyr Lys Gly Phe Gln Ala Leu Gly Asp Ala Ala Asp
65                  70                  75                  80

Ile Arg Phe Val Tyr Thr Pro Ala Met Glu Ser Val Cys Gly Tyr Phe
                85                  90                  95

His Arg Ser His Asn Arg Ser Glu Glu Phe Leu Ile Ala Gly Lys Leu
            100                 105                 110

Gln Asp Gly Leu Leu His Ile Thr Thr Cys Ser Phe Val Ala Pro Trp
        115                 120                 125

Asn Ser Leu Ser Leu Ala Gln Arg Arg Gly Phe Thr Lys Thr Tyr Thr
130                 135                 140

Val Gly Cys Glu Glu Cys Thr Val Phe Pro Cys Leu Ser Ile Pro Cys
145                 150                 155                 160

Lys Leu Gln Ser Gly Thr His Cys Leu Trp Thr Asp Gln Leu Leu Gln
                165                 170                 175

Gly Ser Glu Lys Gly Phe Gln Ser Arg His Leu Ala Cys Leu Pro Arg
            180                 185                 190

Glu Pro Gly Leu Cys Thr Trp Gln Ser Leu Arg Ser Gln Ile Ala
        195                 200                 205
```